US011951179B2

(12) United States Patent
DeRosa et al.

(10) Patent No.: US 11,951,179 B2
(45) Date of Patent: Apr. 9, 2024

(54) LIPID NANOPARTICLE COMPOSITIONS AND METHODS FOR MRNA DELIVERY

(71) Applicant: Translate Bio, Inc., Waltham, MA (US)

(72) Inventors: Frank DeRosa, Cambridge, MA (US); Braydon Charles Guild, Cambridge, MA (US); Michael Heartlein, Cambridge, MA (US)

(73) Assignee: Translate Bio, Inc., Cambridge, MA (US)

( * ) Notice: Subject to any disclaimer, the term of this patent is extended or adjusted under 35 U.S.C. 154(b) by 0 days.

(21) Appl. No.: 18/295,150

(22) Filed: Apr. 3, 2023

(65) Prior Publication Data

US 2023/0285592 A1 Sep. 14, 2023

Related U.S. Application Data

(62) Division of application No. 17/832,202, filed on Jun. 3, 2022, which is a division of application No. 17/558,310, filed on Dec. 21, 2021, now Pat. No. 11,730,825, which is a division of application No. 17/509,674, filed on Oct. 25, 2021, now Pat. No. 11,291,734, which is a division of application No. 17/341,016, filed on Jun. 7, 2021, now Pat. No. 11,185,595, which is a division of application No. 17/099,462, filed on Nov. 16, 2020, now Pat. No. 11,052,159, which is a division of application No. 16/931,231, filed on Jul. 16, 2020, now Pat. No. 10,888,626, which is a division of application No. 16/681,565, filed on Nov. 12, 2019, now abandoned, which is a division of application No. 16/502,672, filed on Jul. 3, 2019, now Pat. No. 10,507,249, which is a division of application No. 16/286,400, filed on Feb. 26, 2019, now Pat. No. 10,350,303, which is a division of application No. 16/233,031, filed on Dec. 26, 2018, now Pat. No. 10,413,618, which is a division of application No. 15/482,117, filed on Apr. 7, 2017, now Pat. No. 10,238,754, which is a division of application No. 14/124,608, filed as application No. PCT/US2012/041724 on Jun. 8, 2012, now abandoned.

(60) Provisional application No. 61/494,881, filed on Jun. 8, 2011.

(51) Int. Cl.

| | |
|---|---|
| ***C12Q 1/00*** | (2006.01) |
| ***A61K 9/00*** | (2006.01) |
| ***A61K 9/127*** | (2006.01) |
| ***A61K 9/51*** | (2006.01) |
| ***A61K 31/7105*** | (2006.01) |
| ***A61K 31/713*** | (2006.01) |
| ***A61K 38/18*** | (2006.01) |
| ***A61K 38/47*** | (2006.01) |
| ***A61K 38/48*** | (2006.01) |
| ***A61K 38/57*** | (2006.01) |
| ***A61K 48/00*** | (2006.01) |
| ***C07K 14/505*** | (2006.01) |
| ***C07K 14/81*** | (2006.01) |
| ***C12N 9/40*** | (2006.01) |
| ***C12N 9/64*** | (2006.01) |
| ***C12N 15/52*** | (2006.01) |
| ***C12N 15/85*** | (2006.01) |

(52) U.S. Cl.

CPC ........ *A61K 48/0008* (2013.01); *A61K 9/0019* (2013.01); *A61K 9/0073* (2013.01); *A61K 9/1271* (2013.01); *A61K 9/1272* (2013.01); *A61K 9/5123* (2013.01); *A61K 31/713* (2013.01); *A61K 38/1816* (2013.01); *A61K 38/47* (2013.01); *A61K 38/4846* (2013.01); *A61K 38/57* (2013.01); *A61K 48/0075* (2013.01); *A61K 48/0091* (2013.01); *C07K 14/505* (2013.01); *C07K 14/8125* (2013.01); *C12N 9/2465* (2013.01); *C12N 9/644* (2013.01); *C12N 15/52* (2013.01); *C12N 15/85* (2013.01); *C12Y 302/01022* (2013.01); *C12Y 304/21022* (2013.01); *A61K 48/00* (2013.01)

(58) Field of Classification Search

None

See application file for complete search history.

(56) References Cited

U.S. PATENT DOCUMENTS

| | | | |
|---|---|---|---|
| 2,647,121 | A | 7/1953 | Jacoby |
| 2,717,909 | A | 9/1955 | Kosmin |
| 2,819,718 | A | 1/1958 | Goldman |
| 2,844,629 | A | 7/1958 | William et al. |
| 3,614,955 | A | 10/1971 | Mirowski |
| 3,656,185 | A | 4/1972 | Carpentier |
| 3,805,301 | A | 4/1974 | Liebig |
| 3,945,052 | A | 3/1976 | Liebig |
| 3,995,623 | A | 12/1976 | Blake et al. |
| 4,013,507 | A | 3/1977 | Rembaum |
| 4,072,146 | A | 2/1978 | Howes |
| 4,096,860 | A | 6/1978 | McLaughlin |
| 4,099,528 | A | 7/1978 | Sorenson et al. |
| 4,106,129 | A | 8/1978 | Carpentier et al. |
| 4,134,402 | A | 1/1979 | Mahurkar |
| 4,140,126 | A | 2/1979 | Choudhury |
| 4,180,068 | A | 12/1979 | Jacobsen et al. |

(Continued)

FOREIGN PATENT DOCUMENTS

| | | |
|---|---|---|
| AU | 2014259532 B2 | 9/2016 |
| CA | 2518132 A1 | 3/2006 |

(Continued)

OTHER PUBLICATIONS

Lucas, et al. (2002) "IL-12 Plasmid Delivery by in Vivo Electroporation for the Successful Treatment of Established Subcutaneous B16.F10 Melanoma", Molecular Therapy, 5(6): 668-75. (Year: 2002).*

(Continued)

*Primary Examiner* — Robert M Kelly

(74) *Attorney, Agent, or Firm* — McNeill Baur PLLC

(57) ABSTRACT

Disclosed herein are compositions and methods for modulating the production of a protein in a target cell. The compositions and methods disclosed herein are capable of ameliorating diseases associated with protein or enzyme deficiencies.

19 Claims, 28 Drawing Sheets

Specification includes a Sequence Listing.

(56) References Cited

U.S. PATENT DOCUMENTS 4,182,833 A 1/1980 Hicks
4,227,533 A 10/1980 Godfrey
4,284,459 A 8/1981 Patel et al.
4,308,085 A 12/1981 Horhold et al.
4,323,525 A 4/1982 Bornat
4,335,723 A 6/1982 Patel
4,339,369 A 7/1982 Hicks et al.
4,355,426 A 10/1982 MacGregor
4,375,817 A 3/1983 Engle et al.
4,385,631 A 5/1983 Uthmann
4,401,472 A 8/1983 Gerber
4,406,656 A 9/1983 Hattler et al.
4,475,972 A 10/1984 Wong
4,530,113 A 7/1985 Matterson
4,550,447 A 11/1985 Seiler, Jr. et al.
4,562,596 A 1/1986 Kornberg
4,568,329 A 2/1986 Mahurkar
4,571,241 A 2/1986 Christopher
4,601,718 A 7/1986 Possis et al.
4,647,416 A 3/1987 Seiler, Jr. et al.
4,662,382 A 5/1987 Sluetz et al.
4,701,162 A 10/1987 Rosenberg
4,710,169 A 12/1987 Christopher
4,720,517 A 1/1988 Ravichandran et al.
4,737,323 A 4/1988 Martin et al.
4,762,915 A 8/1988 Kung et al.
4,782,836 A 11/1988 Alt
4,856,521 A 8/1989 Irnich
4,860,751 A 8/1989 Callaghan
4,878,908 A 11/1989 Martin et al.
4,892,540 A 1/1990 Vallana
4,897,355 A 1/1990 Eppstein et al.
4,920,016 A 4/1990 Allen et al.
4,946,683 A 8/1990 Forssen
4,946,857 A 8/1990 Kanehira et al.
4,960,409 A 10/1990 Catalano
4,966,945 A 10/1990 Drawert et al.
5,024,671 A 6/1991 Tu et al.
5,025,005 A 6/1991 Nomura et al.
5,047,540 A 9/1991 Kamata et al.
5,101,824 A 4/1992 Lekholm
5,104,399 A 4/1992 Lazarus
5,116,360 A 5/1992 Pinchuk et al.
5,138,067 A 8/1992 Kamata et al.
5,151,105 A 9/1992 Kwan-Gett
5,171,678 A 12/1992 Behr et al.
5,176,661 A 1/1993 Evard et al.
5,185,154 A 2/1993 Lasic et al.
5,194,654 A 3/1993 Hostetler et al.
5,200,395 A 4/1993 Eto et al.
5,206,027 A 4/1993 Kitaguchi
5,223,263 A 6/1993 Hostetler et al.
5,261,419 A 11/1993 Osypka
5,264,618 A 11/1993 Felgner et al.
5,279,833 A 1/1994 Rose
5,282,824 A 2/1994 Gianturco
5,284,491 A 2/1994 Sutton et al.
5,300,022 A 4/1994 Klapper et al.
5,314,430 A 5/1994 Bardy
5,330,768 A 7/1994 Park et al.
5,334,761 A 8/1994 Gebeyehu et al.
5,395,619 A 3/1995 Zalipsky et al.
5,405,363 A 4/1995 Kroll et al.
5,405,379 A 4/1995 Lane
5,455,352 A 10/1995 Huellmann et al.
5,464,924 A 11/1995 Silvis et al.
5,503,852 A 4/1996 Steiner et al.
5,528,023 A 6/1996 Butturini et al.
5,552,155 A 9/1996 Bailey et al.
5,556,580 A 9/1996 Suddith
5,580,859 A 12/1996 Felgner et al.
5,595,756 A 1/1997 Bally et al.
5,607,385 A 3/1997 Francischelli et al.
5,609,624 A 3/1997 Kalis
5,610,283 A 3/1997 Buechler
5,614,548 A 3/1997 Piantadosi et al.
5,626,869 A 5/1997 Nyqvist et al.
5,631,018 A 5/1997 Zalipsky et al.
5,677,124 A 10/1997 DuBois et al.
5,693,088 A 12/1997 Lazarus
5,697,953 A 12/1997 Kroll et al.
5,700,437 A 12/1997 Fujii et al.
5,705,188 A 1/1998 Junichi et al.
5,705,385 A 1/1998 Bally et al.
5,736,573 A 4/1998 Galat
5,744,335 A 4/1998 Wolff et al.
5,772,694 A 6/1998 Bokros et al.
5,776,165 A 7/1998 Ripart
5,776,747 A 7/1998 Schinstine et al.
5,783,383 A 7/1998 Kondo et al.
5,783,566 A 7/1998 Ann
5,844,107 A 12/1998 Hanson et al.
5,874,105 A 2/1999 Watkins et al.
5,885,613 A 3/1999 Holland et al.
5,910,168 A 6/1999 Myers et al.
5,916,208 A 6/1999 Luther et al.
5,965,434 A 10/1999 Wolff et al.
5,976,567 A 11/1999 Wheeler et al.
5,976,569 A 11/1999 Milstein
5,981,501 A 11/1999 Wheeler et al.
6,055,454 A 4/2000 Heemels
6,060,308 A 5/2000 Parrington
6,067,471 A 5/2000 Warren
6,077,835 A 6/2000 Hanson et al.
6,090,384 A 7/2000 Ra et al.
6,093,392 A 7/2000 High et al.
6,096,070 A 8/2000 Ragheb et al.
6,096,075 A 8/2000 Bokros et al.
6,120,799 A 9/2000 McDonald et al.
6,147,055 A 11/2000 Hobart et al.
6,152,955 A 11/2000 KenKnight et al.
6,165,763 A 12/2000 Brown et al.
6,169,923 B1 1/2001 Kroll
6,176,877 B1 1/2001 Buchanan et al.
6,183,774 B1 2/2001 Aust et al.
6,204,297 B1 3/2001 Tracy et al.
6,210,892 B1 4/2001 Bennett et al.
6,214,804 B1 4/2001 Felgner et al.
6,271,208 B1 8/2001 Bischoff
6,271,209 B1 8/2001 Smith et al.
6,287,591 B1 9/2001 Semple et al.
6,299,604 B1 10/2001 Ragheb et al.
6,335,199 B1 1/2002 Bischoff et al.
6,358,278 B1 3/2002 Brendzel et al.
6,370,434 B1 4/2002 Zhang et al.
6,371,983 B1 4/2002 Lane
6,387,397 B1 5/2002 Chen et al.
6,417,326 B1 7/2002 Cullis et al.
6,485,726 B1 11/2002 Blumberg et al.
6,509,319 B1 1/2003 Raad et al.
6,534,484 B1 3/2003 Wheeler et al.
6,586,410 B1 7/2003 Wheeler et al.
6,670,178 B1 12/2003 Selden et al.
6,696,424 B1 2/2004 Wheeler
6,733,777 B2 5/2004 Erbacher et al.
6,734,171 B1 5/2004 Saravolac et al.
6,743,823 B1 6/2004 Summar et al.
6,756,055 B2 6/2004 McDonald et al.
6,790,838 B2 9/2004 Alison et al.
6,815,432 B2 11/2004 Wheeler et al.
6,821,530 B2 11/2004 Koob et al.
6,835,395 B1 12/2004 Semple et al.
6,858,224 B2 2/2005 Wheeler et al.
6,858,225 B2 2/2005 Semple et al.
6,887,665 B2 5/2005 Trulson et al.
6,890,554 B2 5/2005 Jessee et al.
6,974,589 B1 12/2005 Huang et al.
6,998,115 B2 2/2006 Langer et al.
7,002,042 B2 2/2006 Gao
7,022,214 B2 4/2006 Olech
7,067,697 B2 6/2006 Gao
7,084,303 B2 8/2006 Watanabe et al.
7,341,738 B2 3/2008 Semple et al.
7,381,422 B2 6/2008 Enas et al.

(56) References Cited

U.S. PATENT DOCUMENTS 7,410,795 B2 8/2008 Hermanson et al.
7,422,902 B1 9/2008 Wheeler et al.
7,427,394 B2 9/2008 Anderson et al.
7,507,859 B2 3/2009 Grinstaff et al.
7,521,187 B2 4/2009 Geall
7,537,768 B2 5/2009 Luke et al.
7,556,684 B2 7/2009 Bury et al.
7,745,651 B2 6/2010 Heyes et al.
7,785,603 B2 8/2010 Luke et al.
7,803,397 B2 9/2010 Heyes et al.
7,888,067 B2 2/2011 Lin et al.
7,888,112 B2 2/2011 Hermanson et al.
7,901,708 B2 3/2011 MacLachlan et al.
7,972,435 B2 7/2011 Bury et al.
8,021,686 B2 9/2011 Semple et al.
8,071,082 B2 12/2011 Zugates et al.
8,101,741 B2 1/2012 MacLachlan et al.
8,106,022 B2 1/2012 Manoharan et al.
8,128,938 B1 3/2012 Luke et al.
8,158,601 B2 4/2012 Chen et al.
8,188,263 B2 5/2012 MacLachlan et al.
RE43,612 E 8/2012 Anderson et al.
8,236,943 B2 8/2012 Lee et al.
8,278,036 B2 10/2012 Kariko et al.
8,278,093 B2 10/2012 Hermanson et al.
8,287,849 B2 10/2012 Langer et al.
8,329,070 B2 12/2012 MacLachlan et al.
8,435,557 B2 5/2013 Enas et al.
8,450,298 B2 5/2013 Mahon et al.
8,450,467 B2 5/2013 Manoharan et al.
8,513,403 B2 8/2013 MacLachlan et al.
8,557,231 B2 10/2013 Langer et al.
8,562,966 B2 10/2013 Zugates et al.
8,569,256 B2 10/2013 Heyes et al.
8,647,864 B2 2/2014 Polo et al.
8,652,512 B2 2/2014 Schmehl et al.
8,673,317 B2 3/2014 Hermanson et al.
8,691,966 B2 4/2014 Kariko et al.
8,710,200 B2 4/2014 Schrum et al.
8,715,999 B2 5/2014 Heinz et al.
8,748,089 B2 6/2014 Kariko et al.
8,802,644 B2 8/2014 Chen et al.
8,808,681 B2 8/2014 Anderson et al.
8,808,982 B2 8/2014 Dahl et al.
8,821,890 B2 9/2014 Luke et al.
8,822,663 B2 9/2014 Schrum et al.
8,828,956 B2 9/2014 Manoharan et al.
8,835,108 B2 9/2014 Kariko et al.
8,846,348 B2 9/2014 Jendrisak et al.
8,853,377 B2 10/2014 Guild et al.
8,859,229 B2 10/2014 Rabinovich et al.
8,883,202 B2 11/2014 Manoharan et al.
8,936,942 B2 1/2015 Heyes et al.
8,969,353 B2 3/2015 Mahon et al.
8,999,351 B2 4/2015 Manoharan et al.
8,999,950 B2 4/2015 MacLachlan et al.
9,005,930 B2 4/2015 Jendrisak et al.
9,012,219 B2 4/2015 Kariko et al.
9,012,498 B2 4/2015 Manoharan et al.
9,018,187 B2 4/2015 Heyes et al.
9,040,256 B2 5/2015 Grunenwald et al.
9,051,567 B2 6/2015 Fitzgerald et al.
9,061,021 B2 6/2015 Guild et al.
9,061,059 B2 6/2015 Chakraborty et al.
9,074,208 B2 7/2015 MacLachlan et al.
9,080,211 B2 7/2015 Grunenwald et al.
9,085,801 B2 7/2015 Grunenwald et al.
9,089,604 B2 7/2015 Chakraborty et al.
9,095,552 B2 8/2015 Chakraborty et al.
9,107,886 B2 8/2015 Chakraborty et al.
9,114,113 B2 8/2015 Chakraborty et al.
9,180,162 B2 11/2015 Hermanson et al.
9,181,319 B2 11/2015 Schrum et al.
9,181,321 B2 11/2015 Heartlein et al.
9,186,325 B2 11/2015 Manoharan et al.
9,186,372 B2 11/2015 de Fougerolles et al.
9,187,748 B2 11/2015 Geisbert et al.
9,192,651 B2 11/2015 Chakraborty et al.
9,220,682 B2 12/2015 Manoharan et al.
9,220,755 B2 12/2015 Chakraborty et al.
9,220,792 B2 12/2015 Chakraborty et al.
9,233,141 B2 1/2016 Chakraborty et al.
9,254,265 B2 2/2016 Geall et al.
9,254,311 B2 2/2016 Bancel et al.
9,295,646 B2 3/2016 Brito et al.
9,295,689 B2 3/2016 de Fougerolles et al.
9,301,923 B2 4/2016 Baryza et al.
9,301,993 B2 4/2016 Chakraborty et al.
9,303,079 B2 4/2016 Chakraborty et al.
9,334,328 B2 5/2016 Schrum et al.
9,345,780 B2 5/2016 Manoharan et al.
9,352,042 B2 5/2016 Heyes et al.
9,352,048 B2 5/2016 Manoharan et al.
9,364,435 B2 6/2016 Yaworski et al.
9,394,234 B2 7/2016 Chen et al.
9,404,127 B2 8/2016 Yaworski et al.
9,428,535 B2 8/2016 de Fougerolles et al.
9,428,751 B2 8/2016 MacDonald et al.
9,464,124 B2 10/2016 Bancel et al.
9,492,386 B2 11/2016 MacLachlan et al.
9,504,651 B2 11/2016 MacLachlan et al.
9,504,734 B2 11/2016 Bancel et al.
9,518,272 B2 12/2016 Yaworksi et al.
9,572,874 B2 2/2017 Fotin-Mleczek et al.
9,572,896 B2 2/2017 Bancel et al.
9,572,897 B2 2/2017 Bancel et al.
9,587,003 B2 3/2017 Bancel et al.
9,616,084 B2 4/2017 Mutzke
9,623,095 B2 4/2017 Kallen et al.
9,636,301 B2 5/2017 Weber
9,636,410 B2 5/2017 Brito et al.
9,655,845 B2 5/2017 Brito et al.
9,657,295 B2 5/2017 Schrum et al.
9,669,089 B2 6/2017 Thess et al.
9,675,668 B2 6/2017 Bancel et al.
9,682,139 B2 6/2017 Manoharan et al.
9,683,233 B2 6/2017 Thess
9,688,729 B2 6/2017 Kramps et al.
9,770,463 B2 9/2017 Geall et al.
9,801,897 B2 10/2017 Geall et al.
9,877,919 B2 1/2018 DeRosa et al.
10,064,959 B2 9/2018 Schrum et al.
10,183,074 B2 1/2019 Brito et al.
10,238,733 B2 3/2019 Brito et al.
10,238,754 B2 3/2019 Guild et al.
10,307,374 B2 6/2019 Brito et al.
10,350,303 B1 7/2019 Guild et al.
10,413,618 B2 9/2019 Guild et al.
10,487,332 B2 11/2019 Geall et al.
10,493,167 B2 12/2019 de Fougerolles et al.
10,507,249 B2 12/2019 Guild et al.
10,532,067 B2 1/2020 Geall et al.
10,577,403 B2 3/2020 De Fougerolles et al.
10,583,203 B2 3/2020 De Fougerolles et al.
10,703,789 B2 7/2020 De Fougerolles et al.
10,772,975 B2 9/2020 Bancel et al.
10,888,626 B2 1/2021 Guild et al.
10,898,574 B2 1/2021 de Fougerolles et al.
11,026,890 B2 6/2021 Brito et al.
11,026,964 B2 6/2021 Geall et al.
11,052,159 B2 7/2021 Guild et al.
11,058,762 B2 7/2021 Geall et al.
11,135,287 B2 10/2021 Brito et al.
11,141,378 B2 10/2021 Yaworski et al.
11,167,028 B2 11/2021 Brito et al.
11,185,595 B2 11/2021 Guild et al.
11,291,635 B2 4/2022 Geall et al.
11,291,682 B2 4/2022 Geall et al.
11,291,734 B2 4/2022 Guild et al.
2002/0022721 A1 2/2002 Trulson et al.
2002/0094528 A1 7/2002 Salafsky
2002/0192651 A1 12/2002 Wheeler et al.
2002/0192721 A1 12/2002 Rizzuto et al.
2002/0193622 A1 12/2002 Watanabe et al.

(56) References Cited

U.S. PATENT DOCUMENTS

2003/0082154 A1 5/2003 Leamon
2003/0083272 A1 5/2003 Wiederholt et al.
2003/0104044 A1 6/2003 Semple et al.
2003/0215395 A1 11/2003 Yu et al.
2004/0110709 A1 6/2004 Li et al.
2004/0132683 A1 7/2004 Felgner et al.
2004/0162256 A1 8/2004 Geall et al.
2004/0224912 A1 11/2004 Dobie et al.
2004/0235982 A1 11/2004 Rabasco et al.
2005/0004058 A1 1/2005 Benoit et al.
2005/0008689 A1 1/2005 Semple et al.
2005/0032730 A1 2/2005 Von Der Mulbe et al.
2005/0054026 A1 3/2005 Atsushi et al.
2005/0059005 A1 3/2005 Tuschl et al.
2005/0059624 A1 3/2005 Hoerr et al.
2005/0065107 A1 3/2005 Hobart et al.
2005/0069590 A1 3/2005 Buehler et al.
2005/0079212 A1 4/2005 Wheeler et al.
2005/0143332 A1 6/2005 Monahan et al.
2005/0148786 A1 7/2005 Ikeda et al.
2005/0158302 A1 7/2005 Faustman et al.
2005/0244961 A1 11/2005 Short et al.
2005/0250723 A1 11/2005 Hoerr et al.
2006/0008910 A1 1/2006 MacLachlan et al.
2006/0059576 A1 3/2006 Pasinetti et al.
2006/0069225 A1 3/2006 Wintermantel et al.
2006/0083780 A1 4/2006 Heyes et al.
2006/0134221 A1 6/2006 Geall
2006/0172003 A1 8/2006 Meers et al.
2006/0204566 A1 9/2006 Smyth-Templeton et al.
2006/0216343 A1 9/2006 Panzner et al.
2006/0223939 A1 10/2006 Lange et al.
2006/0228404 A1 10/2006 Anderson et al.
2006/0241071 A1 10/2006 Grinstaff et al.
2007/0003607 A1 1/2007 Awasthi et al.
2007/0142628 A1 6/2007 Ghoshal et al.
2007/0172950 A1 7/2007 Wheeler et al.
2007/0252295 A1 11/2007 Panzner et al.
2007/0275923 A1 11/2007 Chen et al.
2007/0281336 A1 12/2007 Jendrisak et al.
2008/0145338 A1 6/2008 Anderson et al.
2008/0160048 A1 7/2008 Fuller
2008/0242626 A1 10/2008 Zugates et al.
2008/0260706 A1 10/2008 Rabinovich et al.
2008/0287387 A1 11/2008 Enas et al.
2009/0023673 A1 1/2009 Manoharan et al.
2009/0093433 A1 4/2009 Woolf et al.
2009/0163705 A1 6/2009 Manoharan et al.
2009/0181919 A1 7/2009 Geall
2009/0186805 A1 7/2009 Tabor et al.
2009/0221684 A1 9/2009 Grinstaff et al.
2009/0263407 A1 10/2009 Dande et al.
2009/0270481 A1 10/2009 MacLachlan et al.
2009/0286852 A1 11/2009 Kariko et al.
2009/0326051 A1 12/2009 Corey et al.
2010/0028943 A1 2/2010 Thomas et al.
2010/0035249 A1 2/2010 Hayashizaki et al.
2010/0036084 A1 2/2010 Langer et al.
2010/0041152 A1 2/2010 Wheeler et al.
2010/0047261 A1 2/2010 Hoerr et al.
2010/0120129 A1 5/2010 Amshey et al.
2010/0178699 A1 7/2010 Gao et al.
2010/0189729 A1 7/2010 Hoerr et al.
2010/0266631 A1 10/2010 Polo et al.
2010/0267806 A1 10/2010 Bumcrot et al.
2010/0316696 A1 12/2010 Wiggenhorn et al.
2010/0323356 A1 12/2010 Inoue et al.
2010/0331234 A1 12/2010 Mahon et al.
2011/0009641 A1 1/2011 Anderson et al.
2011/0038941 A1 2/2011 Lee et al.
2011/0064755 A1 3/2011 Geall
2011/0092739 A1 4/2011 Chen et al.
2011/0097716 A1 4/2011 Natt et al.
2011/0143397 A1 6/2011 Kariko et al.
2011/0177124 A1 7/2011 Hermanson et al.
2011/0200582 A1 8/2011 Baryza et al.
2011/0244026 A1 10/2011 Guild et al.
2011/0250237 A1 10/2011 O'Hagan et al.
2011/0256175 A1 10/2011 Hope et al.
2011/0287435 A1 11/2011 Grunenwald et al.
2011/0293703 A1 12/2011 Mahon et al.
2011/0311583 A1 12/2011 Manoharan et al.
2012/0007803 A1 1/2012 Takatsuka
2012/0009222 A1 1/2012 Nguyen et al.
2012/0065252 A1 3/2012 Schrum et al.
2012/0065358 A1 3/2012 Langer et al.
2012/0114831 A1 5/2012 Semple et al.
2012/0128760 A1 5/2012 Manoharan et al.
2012/0129910 A1 5/2012 Thompson et al.
2012/0142756 A1 6/2012 Guild et al.
2012/0195936 A1 8/2012 Rudolph et al.
2012/0237975 A1 9/2012 Schrum et al.
2012/0251560 A1 10/2012 Dahlman et al.
2012/0251618 A1 10/2012 Schrum et al.
2013/0017223 A1 1/2013 Hope et al.
2013/0158021 A1 6/2013 Dong et al.
2013/0171241 A1 7/2013 Geall et al.
2013/0177640 A1 7/2013 Geall et al.
2013/0195967 A1 8/2013 Guild et al.
2013/0259923 A1 10/2013 Chakraborty et al.
2013/0259924 A1 10/2013 Bancel et al.
2013/0266640 A1 10/2013 de Fougerolles et al.
2013/0302401 A1 11/2013 Ma et al.
2014/0010861 A1 1/2014 Bancel et al.
2014/0044772 A1 2/2014 MacLachlan et al.
2014/0094399 A1 4/2014 Langer et al.
2014/0105964 A1 4/2014 Chakraborty et al.
2014/0105965 A1 4/2014 Chakraborty et al.
2014/0147432 A1 5/2014 Chakraborty et al.
2014/0147454 A1 5/2014 Chakraborty et al.
2014/0148502 A1 5/2014 Bancel et al.
2014/0155472 A1 6/2014 Bancel et al.
2014/0155473 A1 6/2014 Bancel et al.
2014/0155474 A1 6/2014 Bancel et al.
2014/0155475 A1 6/2014 Bancel et al.
2014/0161830 A1 6/2014 Anderson et al.
2014/0162897 A1 6/2014 Grunenwald et al.
2014/0171485 A1 6/2014 Bancel et al.
2014/0179771 A1 6/2014 Bancel et al.
2014/0186382 A1 7/2014 Hermanson et al.
2014/0186432 A1 7/2014 Chakraborty et al.
2014/0193482 A1 7/2014 Chakraborty et al.
2014/0194494 A1 7/2014 Bancel et al.
2014/0199371 A1 7/2014 Chakraborty et al.
2014/0200261 A1 7/2014 Hoge et al.
2014/0200262 A1 7/2014 Chakraborty et al.
2014/0200263 A1 7/2014 Bancel et al.
2014/0200264 A1 7/2014 Bancel et al.
2014/0206752 A1 7/2014 Afeyan et al.
2014/0206753 A1 7/2014 Guild et al.
2014/0206755 A1 7/2014 Bancel et al.
2014/0206852 A1 7/2014 Bancel et al.
2014/0221248 A1 8/2014 Jendrisak et al.
2014/0221465 A1 8/2014 Bancel et al.
2014/0227300 A1 8/2014 Chin et al.
2014/0227346 A1 8/2014 Geall et al.
2014/0243399 A1 8/2014 Schrum et al.
2014/0249208 A1 9/2014 Bancel et al.
2014/0255467 A1 9/2014 Bancel et al.
2014/0255468 A1 9/2014 Bancel et al.
2014/0275227 A1 9/2014 Hoge et al.
2014/0275229 A1 9/2014 Bancel et al.
2014/0288160 A1 9/2014 Guild et al.
2014/0294937 A1 10/2014 MacLachlan et al.
2014/0294938 A1 10/2014 Guild et al.
2014/0294940 A1 10/2014 Guild et al.
2014/0329884 A1 11/2014 Dong et al.
2014/0343129 A1 11/2014 de Fougerolles et al.
2014/0363876 A1 12/2014 Jendrisak et al.
2015/0004217 A1 1/2015 Guild et al.
2015/0005372 A1 1/2015 Hoge et al.
2015/0011615 A1 1/2015 Manoharan et al.
2015/0011633 A1 1/2015 Shorr et al.
2015/0017211 A1 1/2015 de Fougerolles et al.

(56) References Cited

U.S. PATENT DOCUMENTS

| | | | |
|---|---|---|---|
| 2015/0038556 | A1 | 2/2015 | Heartlein et al. |
| 2015/0038558 | A1 | 2/2015 | Kariko et al. |
| 2015/0044277 | A1 | 2/2015 | Bancel et al. |
| 2015/0050354 | A1 | 2/2015 | Bouchon et al. |
| 2015/0051268 | A1 | 2/2015 | Bancel et al. |
| 2015/0056253 | A1 | 2/2015 | Bancel et al. |
| 2015/0064235 | A1 | 3/2015 | Bancel et al. |
| 2015/0064236 | A1 | 3/2015 | Bancel et al. |
| 2015/0064242 | A1 | 3/2015 | Heyes et al. |
| 2015/0064725 | A1 | 3/2015 | Schrum et al. |
| 2015/0086614 | A1 | 3/2015 | Bancel et al. |
| 2015/0110857 | A1 | 4/2015 | DeRosa et al. |
| 2015/0110858 | A1 | 4/2015 | DeRosa et al. |
| 2015/0110859 | A1 | 4/2015 | Heartlein et al. |
| 2015/0119444 | A1 | 4/2015 | Manoharan et al. |
| 2015/0119445 | A1 | 4/2015 | Manoharan et al. |
| 2015/0157565 | A1 | 6/2015 | Heartlein et al. |
| 2015/0166465 | A1 | 6/2015 | Chen et al. |
| 2015/0190515 | A1 | 7/2015 | Manoharan et al. |
| 2015/0191760 | A1 | 7/2015 | Jendrisak et al. |
| 2015/0265708 | A1 | 9/2015 | Manoharan et al. |
| 2015/0267192 | A1 | 9/2015 | Heartlein et al. |
| 2015/0315541 | A1 | 11/2015 | Bancel et al. |
| 2015/0315584 | A1 | 11/2015 | MacDonald et al. |
| 2015/0366997 | A1 | 12/2015 | Guild et al. |
| 2016/0095924 | A1 | 4/2016 | Hope et al. |
| 2016/0114011 | A1 | 4/2016 | Bancel et al. |
| 2016/0115477 | A1 | 4/2016 | MacLachlan et al. |
| 2016/0115483 | A1 | 4/2016 | MacLachlan et al. |
| 2016/0136236 | A1 | 5/2016 | Hoge et al. |
| 2016/0151284 | A1 | 6/2016 | Heyes et al. |
| 2016/0158385 | A1 | 6/2016 | Bancel et al. |
| 2016/0193299 | A1 | 7/2016 | de Fougerolles et al. |
| 2016/0194368 | A1 | 7/2016 | Hoge et al. |
| 2016/0194625 | A1 | 7/2016 | Hoge et al. |
| 2016/0199485 | A1 | 7/2016 | Manoharan et al. |
| 2016/0213785 | A1 | 7/2016 | Manoharan et al. |
| 2016/0237108 | A1 | 8/2016 | Fraley et al. |
| 2016/0237134 | A1 | 8/2016 | Hoge et al. |
| 2016/0250354 | A1 | 9/2016 | Manoharan et al. |
| 2016/0251681 | A1 | 9/2016 | Yaworski et al. |
| 2016/0256567 | A1 | 9/2016 | Heyes et al. |
| 2016/0256568 | A1 | 9/2016 | Heyes et al. |
| 2016/0256573 | A1 | 9/2016 | de Fougerolles et al. |
| 2016/0264971 | A1 | 9/2016 | Geisbert et al. |
| 2016/0264975 | A1 | 9/2016 | Schrum et al. |
| 2016/0274089 | A1 | 9/2016 | Ciufolini et al. |
| 2016/0304552 | A1 | 10/2016 | Roy et al. |
| 2016/0317647 | A1 | 11/2016 | Ciaramella et al. |
| 2016/0317676 | A1 | 11/2016 | Hope et al. |
| 2016/0331828 | A1 | 11/2016 | Ciaramella et al. |
| 2016/0348099 | A1 | 12/2016 | Roy et al. |
| 2016/0354490 | A1 | 12/2016 | Roy et al. |
| 2016/0354491 | A1 | 12/2016 | Roy et al. |
| 2016/0354492 | A1 | 12/2016 | Roy et al. |
| 2016/0354493 | A1 | 12/2016 | Roy et al. |
| 2016/0367687 | A1 | 12/2016 | Manoharan et al. |
| 2016/0367702 | A1 | 12/2016 | Hoge et al. |
| 2016/0375134 | A1 | 12/2016 | Bancel et al. |
| 2016/0375137 | A9 | 12/2016 | Manoharan et al. |
| 2017/0000858 | A1 | 1/2017 | Fotin-Mleczek et al. |
| 2017/0000870 | A1 | 1/2017 | Hoerr et al. |
| 2017/0000871 | A1 | 1/2017 | Probst et al. |
| 2017/0002060 | A1 | 1/2017 | Bolen et al. |
| 2017/0007702 | A1 | 1/2017 | Heyes et al. |
| 2017/0014496 | A1 | 1/2017 | Fotin-Mleczek et al. |
| 2017/0027658 | A1 | 2/2017 | Black et al. |
| 2017/0028059 | A1 | 2/2017 | Baumhof et al. |
| 2017/0029847 | A1 | 2/2017 | Thess |
| 2017/0042814 | A1 | 2/2017 | Yaworski et al. |
| 2017/0056528 | A1 | 3/2017 | De Fougerolles et al. |
| 2017/0056529 | A1 | 3/2017 | Thess et al. |
| 2017/0065675 | A1 | 3/2017 | Bancel et al. |
| 2017/0065727 | A1 | 3/2017 | Fotin-Mleczek et al. |
| 2017/0114378 | A1 | 4/2017 | Wochner et al. |
| 2017/0128549 | A1 | 5/2017 | Fotin-Mileczek et al. |
| 2017/0136131 | A1 | 5/2017 | Atanu et al. |
| 2017/0151333 | A1 | 6/2017 | Heyes et al. |
| 2017/0157268 | A1 | 6/2017 | Ansell et al. |
| 2017/0166905 | A1 | 6/2017 | Eberle et al. |
| 2017/0173128 | A1 | 6/2017 | Hoge et al. |
| 2017/0175129 | A1 | 6/2017 | Roy et al. |
| 2017/0182081 | A1 | 6/2017 | Mutzke |
| 2017/0182150 | A1 | 6/2017 | Kallen et al. |
| 2017/0190661 | A1 | 6/2017 | Payne et al. |
| 2017/0189552 | A1 | 7/2017 | Hasenpusch |
| 2018/0161451 | A1 | 1/2018 | Fotin-Mleczek et al. |
| 2019/0343862 | A1 | 11/2019 | Geall et al. |
| 2020/0113830 | A1 | 4/2020 | Geall et al. |
| 2020/0113831 | A1 | 4/2020 | Geall et al. |
| 2020/0230058 | A1 | 7/2020 | Geall et al. |
| 2021/0268013 | A1 | 9/2021 | Geall et al. |
| 2021/0290755 | A1 | 9/2021 | Geall et al. |
| 2022/0056449 | A1 | 2/2022 | Geall |

FOREIGN PATENT DOCUMENTS

| | | | |
|---|---|---|---|
| CA | 2807552 | A1 | 2/2012 |
| CN | 1399561 | | 2/2003 |
| CN | 100569877 | C | 12/2009 |
| CN | 101863544 | A | 10/2010 |
| DE | 24 30 998 | A1 | 1/1975 |
| DE | 2520814 | A1 | 11/1976 |
| DE | 3728917 | A1 | 3/1989 |
| EP | 6 73 637 | A1 | 9/1995 |
| EP | 0783297 | A1 | 7/1997 |
| EP | 0853123 | A1 | 7/1998 |
| EP | 0959092 | A1 | 11/1999 |
| EP | 2449106 | A1 | 11/1999 |
| EP | 1026253 | A2 | 8/2000 |
| EP | 3721943 | A | 1/2005 |
| EP | 1519714 | B1 | 4/2005 |
| EP | 1979364 | A2 | 10/2008 |
| EP | 2045251 | A1 | 4/2009 |
| EP | 2338478 | B1 | 6/2011 |
| EP | 2338520 | A1 | 6/2011 |
| EP | 2450031 | A1 | 5/2012 |
| EP | 2502617 | A1 | 9/2012 |
| EP | 2532649 | A1 | 12/2012 |
| EP | 2578685 | A2 | 4/2013 |
| EP | 2823809 | A1 | 1/2015 |
| EP | 3590949 | A1 | 1/2020 |
| FR | 1 378 382 | A | 11/1964 |
| FR | 2 235 112 | A1 | 1/1975 |
| GB | 1072118 | A | 6/1967 |
| GB | 1602085 | A | 11/1981 |
| JP | H07-053535 | | 2/1955 |
| JP | S48-022365 | | 3/1973 |
| JP | S49-127908 | A | 12/1974 |
| JP | S51-023537 | | 2/1976 |
| JP | 51-125144 | | 11/1976 |
| JP | S52-010847 | | 1/1977 |
| JP | 63-125144 | | 5/1988 |
| JP | 63-154788 | | 6/1988 |
| JP | H09-505593 | | 6/1997 |
| JP | H10-197978 | | 7/1998 |
| JP | 11-005786 | A | 1/1999 |
| JP | 11-080142 | | 3/1999 |
| JP | 2001-523215 | A | 11/2001 |
| JP | 2002-167368 | A | 6/2002 |
| JP | 2003-519199 | A | 6/2003 |
| JP | 4-108173 | B2 | 6/2008 |
| JP | 2008-247749 | | 10/2008 |
| JP | 2011-516586 | A | 5/2011 |
| JP | 50-24216 | B2 | 9/2012 |
| RU | 2248213 | C2 | 3/2005 |
| WO | WO-1990/11092 | A1 | 10/1990 |
| WO | WO-1993/18229 | A1 | 9/1993 |
| WO | WO-1993/18754 | A1 | 9/1993 |
| WO | WO-1995/11004 | A1 | 4/1995 |
| WO | WO-1995/14651 | A1 | 6/1995 |
| WO | WO-1995/27478 | A1 | 10/1995 |
| WO | WO-1996/18372 | A2 | 6/1996 |
| WO | WO-1996/26179 | A1 | 8/1996 |

(56) References Cited

FOREIGN PATENT DOCUMENTS

| | | | |
|---|---|---|---|
| WO | WO-1996/37211 | A1 | 11/1996 |
| WO | WO-1996/40964 | A2 | 12/1996 |
| WO | WO-1997/46223 | A1 | 12/1997 |
| WO | WO-1998/10748 | A1 | 3/1998 |
| WO | WO-1998/16202 | A2 | 4/1998 |
| WO | WO-1998/51278 | A2 | 11/1998 |
| WO | WO-1999/14346 | A2 | 3/1999 |
| WO | WO-1999/18933 | A2 | 4/1999 |
| WO | WO-2000/03044 | A1 | 1/2000 |
| WO | WO-2000/06120 | | 2/2000 |
| WO | WO-2000/62813 | A2 | 10/2000 |
| WO | WO-2000/64484 | A2 | 11/2000 |
| WO | WO-2000/69913 | A1 | 11/2000 |
| WO | WO-2001/05375 | A1 | 1/2001 |
| WO | WO-2001/07599 | A1 | 2/2001 |
| WO | WO-2001/23002 | A1 | 4/2001 |
| WO | WO-2002/00870 | A2 | 1/2002 |
| WO | WO-2002/22709 | A1 | 3/2002 |
| WO | WO-2002/31025 | A2 | 4/2002 |
| WO | WO-2002/34236 | A2 | 5/2002 |
| WO | WO-2002/42317 | A2 | 5/2002 |
| WO | WO-2003/040288 | A2 | 5/2003 |
| WO | WO-2003/070735 | A2 | 8/2003 |
| WO | WO-2004/002453 | A1 | 1/2004 |
| WO | WO-2004/043588 | A2 | 5/2004 |
| WO | WO-2004/048345 | A2 | 6/2004 |
| WO | WO-2004/058166 | | 7/2004 |
| WO | WO-2004/060059 | | 7/2004 |
| WO | WO-2004/060363 | | 7/2004 |
| WO | WO-2004/106411 | A2 | 12/2004 |
| WO | WO-2006/074546 | A1 | 1/2005 |
| WO | WO-2005/026372 | A1 | 3/2005 |
| WO | WO-2005/028619 | A2 | 3/2005 |
| WO | WO-2005/037226 | A2 | 4/2005 |
| WO | WO-2005/116270 | | 12/2005 |
| WO | WO-2005/120152 | A2 | 12/2005 |
| WO | WO-2005/121348 | A1 | 12/2005 |
| WO | WO-2006/000448 | A2 | 1/2006 |
| WO | WO-2006/016097 | A2 | 2/2006 |
| WO | WO-2006/060723 | | 6/2006 |
| WO | WO-2006/082088 | A1 | 8/2006 |
| WO | WO-2006/105043 | A2 | 10/2006 |
| WO | WO-2006/138380 | A2 | 12/2006 |
| WO | WO-2007/024708 | A2 | 3/2007 |
| WO | WO-2007/031091 | A2 | 3/2007 |
| WO | WO-2007/070705 | A1 | 6/2007 |
| WO | WO-2007/120863 | A2 | 10/2007 |
| WO | WO-2007/126386 | A1 | 11/2007 |
| WO | WO-2007/143659 | A2 | 12/2007 |
| WO | WO-2008/011561 | A2 | 1/2008 |
| WO | WO-2008/042973 | A2 | 4/2008 |
| WO | WO-2008/045548 | A2 | 4/2008 |
| WO | WO2008/052770 | A2 | 5/2008 |
| WO | WO-2008/083949 | A2 | 7/2008 |
| WO | WO-2008/113364 | A2 | 9/2008 |
| WO | WO-2009/024599 | A1 | 2/2009 |
| WO | WO-2009/046220 | A2 | 4/2009 |
| WO | WO-2009/086558 | A1 | 7/2009 |
| WO | WO-2009/098277 | A1 | 8/2009 |
| WO | WO-2009/127060 | A1 | 10/2009 |
| WO | WO-2009/127230 | A1 | 10/2009 |
| WO | WO-2010/009065 | | 1/2010 |
| WO | WO-2010/009277 | | 1/2010 |
| WO | WO-2010/037408 | A1 | 4/2010 |
| WO | WO-2010/042877 | A1 | 4/2010 |
| WO | WO-2010/045512 | A2 | 4/2010 |
| WO | WO-2010/053572 | A2 | 5/2010 |
| WO | WO-2010/054401 | A1 | 5/2010 |
| WO | WO-2010/054405 | A1 | 5/2010 |
| WO | WO-2010/056403 | A1 | 5/2010 |
| WO | WO-2010/088537 | A2 | 8/2010 |
| WO | WO-2010/099387 | A1 | 9/2010 |
| WO | WO-2010/114789 | A1 | 10/2010 |
| WO | WO-2010/119256 | A1 | 10/2010 |
| WO | WO-2010/129709 | A1 | 11/2010 |
| WO | WO-2010/144740 | A1 | 12/2010 |
| WO | WO-2010/147992 | A1 | 12/2010 |
| WO | WO-2010/148013 | A2 | 12/2010 |
| WO | WO-2011/005799 | | 1/2011 |
| WO | WO-2011/012316 | A2 | 2/2011 |
| WO | WO-2011/012746 | A2 | 2/2011 |
| WO | WO-2011/039144 | A1 | 4/2011 |
| WO | WO-2011/068810 | A1 | 6/2011 |
| WO | WO-2011/075656 | A1 | 6/2011 |
| WO | WO-2011/076807 | | 6/2011 |
| WO | WO-2011/141705 | A1 | 11/2011 |
| WO | WO-2012/006369 | | 1/2012 |
| WO | WO-2012/006372 | | 1/2012 |
| WO | WO-2012/006376 | | 1/2012 |
| WO | WO-2012/006377 | | 1/2012 |
| WO | WO-2012/006378 | | 1/2012 |
| WO | WO-2012/006380 | | 1/2012 |
| WO | WO-2012/019168 | A2 | 2/2012 |
| WO | WO-2012/019630 | A1 | 2/2012 |
| WO | WO-2012/019780 | A1 | 2/2012 |
| WO | WO-2012/027675 | A2 | 3/2012 |
| WO | WO-2012/030901 | | 3/2012 |
| WO | WO-2012/031043 | | 3/2012 |
| WO | WO-2012/031046 | | 3/2012 |
| WO | WO-2012/045075 | A1 | 4/2012 |
| WO | WO-2012/045082 | A2 | 4/2012 |
| WO | WO-2012/075040 | A2 | 6/2012 |
| WO | WO-2012/133737 | A1 | 10/2012 |
| WO | WO-2012/135025 | A2 | 10/2012 |
| WO | WO-2012/135805 | A2 | 10/2012 |
| WO | WO-2012/158736 | A1 | 11/2012 |
| WO | WO-2012/170889 | A1 | 12/2012 |
| WO | WO-2012/170930 | A1 | 12/2012 |
| WO | WO-2013/006825 | A1 | 1/2013 |
| WO | WO-2013/006834 | | 1/2013 |
| WO | WO-2013/006837 | | 1/2013 |
| WO | WO-2013/006838 | | 1/2013 |
| WO | WO-2013/006842 | | 1/2013 |
| WO | WO-2013/033563 | | 3/2013 |
| WO | WO-2013/039857 | A1 | 3/2013 |
| WO | WO-2013/039861 | A2 | 3/2013 |
| WO | WO-2013/052523 | A1 | 4/2013 |
| WO | WO-2013/063468 | A1 | 5/2013 |
| WO | WO-2013/090186 | | 6/2013 |
| WO | WO-2013/090648 | A1 | 6/2013 |
| WO | WO-2013/096709 | A2 | 6/2013 |
| WO | WO-2013/101690 | A1 | 7/2013 |
| WO | WO-2013/102203 | A1 | 7/2013 |
| WO | WO-2013/106496 | A1 | 7/2013 |
| WO | WO-2013/126803 | A1 | 8/2013 |
| WO | WO-2013/130161 | | 9/2013 |
| WO | WO-2013/149140 | A1 | 10/2013 |
| WO | WO-2013/149141 | A1 | 10/2013 |
| WO | WO-2013/151663 | A1 | 10/2013 |
| WO | WO-2013/151664 | A1 | 10/2013 |
| WO | WO-2013/151665 | A2 | 10/2013 |
| WO | WO-2013/151666 | A2 | 10/2013 |
| WO | WO-2013/151667 | A1 | 10/2013 |
| WO | WO-2013/151668 | A2 | 10/2013 |
| WO | WO-2013/151669 | A1 | 10/2013 |
| WO | WO-2013/151670 | A2 | 10/2013 |
| WO | WO-2013/151671 | A1 | 10/2013 |
| WO | WO-2013/151672 | A2 | 10/2013 |
| WO | WO-2013/151736 | A2 | 10/2013 |
| WO | WO-2013/096709 | A3 | 12/2013 |
| WO | WO-2013/182683 | A1 | 12/2013 |
| WO | WO-2013/185067 | A1 | 12/2013 |
| WO | WO-2013/185069 | A1 | 12/2013 |
| WO | WO-2013/151665 | A3 | 2/2014 |
| WO | WO-2014/028487 | A1 | 2/2014 |
| WO | WO-2014/089486 | A1 | 6/2014 |
| WO | WO-2014/093924 | A1 | 6/2014 |
| WO | WO-2014/113089 | A2 | 7/2014 |
| WO | WO-2014/144039 | A1 | 9/2014 |
| WO | WO-2014/144196 | A1 | 9/2014 |
| WO | WO-2014/144711 | A1 | 9/2014 |
| WO | WO-2014/144767 | A1 | 9/2014 |
| WO | WO-2014/152027 | A1 | 9/2014 |
| WO | WO-2014/152030 | A1 | 9/2014 |

(56) References Cited

FOREIGN PATENT DOCUMENTS

| | | | |
|---|---|---|---|
| WO | WO-2014/152031 | A1 | 9/2014 |
| WO | WO-2014/152211 | A1 | 9/2014 |
| WO | WO-2014/152513 | A1 | 9/2014 |
| WO | WO-2014/152540 | A1 | 9/2014 |
| WO | WO-2014/152659 | A1 | 9/2014 |
| WO | WO-2014/152673 | A1 | 9/2014 |
| WO | WO-2014/152774 | A1 | 9/2014 |
| WO | WO-2014/152940 | A1 | 9/2014 |
| WO | WO-2014/152966 | A1 | 9/2014 |
| WO | WO-2014/153052 | A2 | 9/2014 |
| WO | WO-2014/158795 | A1 | 10/2014 |
| WO | WO-2014/159813 | A1 | 10/2014 |
| WO | WO-2014/17956-2 | A1 | 11/2014 |
| WO | WO-2014/210356 | A1 | 12/2014 |
| WO | WO-2015/006747 | A2 | 1/2015 |
| WO | WO-2015/011633 | A1 | 1/2015 |
| WO | WO-2015/048744 | A2 | 4/2015 |
| WO | WO-2015/051169 | A2 | 4/2015 |
| WO | WO-2015/051173 | A2 | 4/2015 |
| WO | WO-2015/058069 | A1 | 4/2015 |
| WO | WO-2015/085318 | | 6/2015 |
| WO | WO-2015/089511 | | 6/2015 |
| WO | WO-2016/054421 | | 4/2016 |
| WO | WO-2016/071857 | A1 | 5/2016 |
| WO | WO-2016/077123 | A1 | 5/2016 |
| WO | WO-2016/077125 | | 5/2016 |
| WO | WO-2016/077125 | A1 | 5/2016 |
| WO | WO-2016/118724 | | 7/2016 |
| WO | WO-2016/118725 | | 7/2016 |
| WO | WO-2016/154127 | | 9/2016 |
| WO | WO-2016/164762 | | 10/2016 |
| WO | WO-2016/183366 | A2 | 11/2016 |
| WO | WO-2016/197132 | A1 | 12/2016 |
| WO | WO-2016/197133 | A1 | 12/2016 |
| WO | WO-2016/201377 | A1 | 12/2016 |
| WO | WO-2017/019891 | A2 | 2/2017 |
| WO | WO-2017/049074 | A1 | 3/2017 |
| WO | WO-2017/049286 | A1 | 3/2017 |
| WO | WO-2017049275 | A2 | 3/2017 |
| WO | WO-2017102010 | A1 | 6/2017 |
| WO | WO-2017103088 | A1 | 6/2017 |
| WO | WO-2017108087 | A1 | 6/2017 |
| WO | WO-2017109134 | A1 | 6/2017 |
| WO | WO-2017109161 | A1 | 6/2017 |
| WO | WO-2017117528 | A1 | 7/2017 |
| WO | WO-2017117530 | A1 | 7/2017 |
| WO | WO-2019207060 | A1 | 10/2019 |

OTHER PUBLICATIONS

Eijnden, et al. (2005) “IL-23 up-regulates IL-10 and induces IL-17 synthesis by polyclonally activated naïve T cells in human”, European Journal of Immunology. (Year: 2005).*

Kumar, et al. (2010) “Nuclear Import of Cytoplasmic Poly(A) Binding Protein Restricts Gene Expression via Hyperadenylation and Nuclear Retention of mRNA” Molecular and Cellular Biology, 30(21): 4996-5008. (Year: 2010).*

Balazs, et al. (2011) “Liposomes for Use in Gene Delivery”, Journal of Drug Delivery, Article ID 326497, 12 pages long.*

U.S. Appl. No. 60/083,294.

U.S. Appl. No. 61/494,714.

U.S. Appl. No. 61/494,745.

U.S. Appl. No. 61/494,881.

U.S. Appl. No. 61/494,882.

Adami R.C. et al. An amino acid-based amphoteric liposomal delivery system for systemic administration of siRNA. Molecular Therapy 19(6):1141-1151 (2011).

Akinc A. et al. A combinatorial library of lipid-like materials for delivery of RNAi therapeutics. Nature Biotechnology 26(5):561-569 (2008).

Akinc A. et al. Development of lipidoid-siRNA formulations for systemic delivery to the liver. Molecular Therapy 17(5):872-879 (2009).

Alton E.W.F.W. et al. Cationic Lipid-Mediated CFTR Gene Transfer to the Lungs and Nose of Patients with Cystic Fibrosis: a Double-Blind Placebo-Controlled Trial Lancet 353:947-954 (1999).

Anderson D.G. et al. Structure/property studies of polymeric gene delivery using a library of poly(beta-amino esters). Molecular Therapy 11(3):426-434 (2005).

Anderson D.M. et al. Stability of mRNA/Cationic Lipid Lipoplexes in Human and Rat Cerebrospinal Fluid: Methods and Evidence for Nonviral mRNA Gene Delivery to the Central Nervous System Human Gene Therapy 14:191-202 (2003).

Anderson J. Biological Responses to Materials. Annual Review of Materials Research 31:81-110 (2001).

Anderson W. French Human gene therapy Nature 392 25-30 (1998).

Andries O. et al. Comparison of the Gene Transfer Efficiency of mRNA/GL67 and pDNA/GL67 Complexes in Respiratory Cells Mol. Pharmaceut. 9: 2136-2145 (2012).

Auffray C. et al. Purification of Mouse Immunoglubulin Heavy-Chain Messenger RNAs from Total Myeloma Tumor RNA European Journal of Biochemistry 107(2):303-314 (1980).

Author Unknown Blood Proteins published by Wikipedia San Francisco CA 2 pages <http://en.wikipedia.org/wiki/Biood_proteins> downloaded May 17, 2015.

Bahlke M. A. et al. Progress towards in vivo use of siRNAs Molecular Therapy 13:644-670 (2006).

Bajaj A. et al. Synthesis and gene transfection efficacies of PEI-cholesterol-based lipopolymers. Bioconjugate Chemistry 19(8):1640-516511 (2008).

Barreau C. et al. Liposome-mediated RNA transfection should be used with caution RNA 12:1790-1793 (2006).

Behike et al. Progress towards in vivo Use of siRNAs Molecular Therapy 13:644-70 (2006).

Behr J. et al. Efficient Gene Transfer into Mammalian Primary Endocrine Cells with Lipo Polyamine-Coated DNA Proc. Nat.'l Acad. Sci. 86: 6982-6986 (1989).

Bennett J. Immune response following intraocular delivery of recombinant viral vectors Gene Therapy 10: 977-982 (2003).

Bhaduri S. et al. Procedure for the preparation of milligram quantities of adenovirus messenger ribonucleic acid J. Virol. 10(6): 1126-1129 (1972).

Bloomfield V.A. Quasi-Elastic Light Scattering Applications in Biochemistry and Biology Ann. Rev. Biophys. Bioeng. 10:421-450 (1981).

Boussif O. et al. A versatile vector for gene and oligonucleotide transfer into cells in culture and in vivo: polyethylenimine. Proceedings of the National Academy of Sciences of the USA. 92(16):7297-7301 (1995).

Braun C.S. et al. Structure/function relationships of polyamidoamine/DNA dendrimers as gene delivery vehicles. Journal of Pharmaceutical Sciences 94(2):423-436 (2005).

Breunig M. et al. Breaking up the correlation between efficacy and toxicity for nonviral gene delivery. Proceedings of the National Academy of Sciences of the U S A. 104(36):14454- 14459 (2007).

Breunig M. et al. Mechanistic investigation of poly(ethylene imine)-based siRNA delivery: disulfide bonds boost intracellular release of the cargo. Journal of Controlled Release 130(1):57-63 (2008).

Brey D.M. et al. Controlling poly(beta-amino ester) network properties through macromer branching. Acta Biomaterialia 4(2):207-217 (2008).

Brey D.M. et al. Influence of macromer molecular weight and chemistry on poly(beta-amino ester) network properties and initial cell interactions. Journal of Biomedical Materials Research Part A 85(3):731-741 (2007).

Budker V. et al. Protein/Amphipathic Polyamine Complexes Enable Highly Efficient Transfection with Minimal Toxicity BioTechniques 23: 139-147 (1997).

Burger G. et al. Sequencing complete mitochondrial and plastid genomes Nature Protocols 2: 603-614 (2007).

Burnett J.C. et al. Current progress of siRNA/shRNA therapeutics in clinical trials. Biotechnology Journal 6(9):1130-1146 (2011).

Burney et al. “Gene therapy for treatment of cystic fibrosis” The Application of Clinical Genetics vol. 5 pp. 29-36 (2012).

(56) References Cited

OTHER PUBLICATIONS

Byk G. et al. Synthesis activity and structure—activity relationship studies of novel cationic lipids for DNA transfer. Journal of Medical Chemistry 41(2):224-235 (1998).
Caplen N.J. et al. In vitro liposome-mediated DNA transfection of epithelial cell lines using the cationic liposome DC-Chol/DOPE Gene Therapy 2:603-613 (1995).
Cassiman D. Gene transfer for inborn errors of metabolism of the liver: the clinical perspective Current Pharmaceutical Design 17(24):2550-2557 (2011).
Castanotto D. et al. The promises and pitfalls of RNA-interference-based therapeutics. Nature 457(7228):426-433 (2009).
Chakraborty C. Potentiality of Small Interfering RNAs (siRNA) as Recent Therapeutic Targets for Gene-Silencing. Current Drug Targets 8(3):469-82 (2007).
Chandler R. et al. Liver-directed adeno-associated virus serotype 8 gene transfer rescues a lethal murine model of citrullinemmia type 1 Gene Therapy 20:1188-1191 (2013).
Chau Y. et al. Investigation of targeting mechanism of new dextran-peptide-methotrexate conjugates using biodistribution study in matrix-metalloproteinase-overexpressing tumor xenograft model J. Pharm. Sci. 95(3): 542-551 (2006).
Chen D. et al. Rapid discovery of potent siRNA-containing lipid nanoparticles enabled by controlled microfluidic formulation. Journal of the American Chemical Society 134(16):6948-6951 (2012).
Chen Y. and Huang L. Tumor-targeted delivery of siRNA by non-viral vector: safe and effective cancer therapy. Expert Opinion on Drug Delivery 5(12):1301-1311 (2008).
Chiou H.C. et al. Enhanced resistance to nuclease degradation of nucleic acids complexed to; asialoglycoprotein-polylysine carriers Nucleic Acids Research 22(24):5439-46 (1994).
Christensen U.B. et al. Intercalating nucleic acids containing insertions of 1-O-(1-pyrenylmethyl)glycerol: stabilisation of dsDNA and discrimination of DNA over RNA Nucl. Acids. Res. 30(22): 4918-4925 (2002).
Conese M. et al. Gene and Cell Therapy for Cystic Fibrosis: From Bench to Bedside J. Cyst. Fibros. 10 Suppl 2:S114-s128 (2011).
Cotten M. et al. Receptor-mediated transport of DNA into eukaryotic cells. Methods in Enzymology 217 (H):618-644 (1993).
Cowling V.H. Regulation of mRNA cap methylation Biochemical Journal 425:295-302 (2010).
Creusat G. et al. Proton sponge trick for pH-sensitive disassembly of polyethylenimine-based siRNA delivery systems. Bioconjugate Chemistry 21(5):994-1002 (2010).
Crooke et al. Liposomal Formulations for Nucleic Acid Delivery Antisense Drug Technology: Principles Strategies and Applications Second Edition Ch. 9 237-270 (2007).
Crooke S.T. Molecular mechanisms of action of antisense drugs. Biochimica et Biophysica Acta 1489(1):31-44. Review (1999).
Crystal R.G. Transfer of genes to humans: early lessons and obstacles to success. Science 270(5235):404-410. Review (1995).
Damen M. et al. Delivery of DNA and siRNA by novel gemini-like amphiphilic peptides. Journal of Controlled Release 145(1):33-39 (2010).
Dande P. et al. Improving RNA interference in mammalian cells by 4'-thio-modified small interfering RNA (siRNA): effect on siRNA activity and nuclease stability when used in combination with 2'-0-alkyl modifications Journal of Medicinal Chemistry 49(5):1624-1634 (2006).
Dassa et al Expression of the alternative oxidase complements cytochrome c oxidase deficiency in human cells EMBO Mol. Med. 1(1): 30-36 (2009).
Davis M. E. The first targeted delivery of siRNA in humans via a self-assembling cyclodextrin polymer-based nanoparticle: from concept to clinic. Molecular Pharmacuetics 6(3):659-668 (2009).
Davis M.E. et al. Evidence of RNAi in humans from systemically administered siRNA via Targeted nanoparticles. Nature 464(7291):1067-1070 (2010).
Debus H. et al. Delivery of Messenger RNA Using Poly(ethylene imine)-poly(ethylene glycol)-Copolymer Blends for Polyplex Formation: Biophysical Characterization and In Vitro Transfection Properties J. Control. Rel. 148:334-343 (2010).
Decher G. Fuzzy Nanoassemblies: Toward Layered Polymeric Multicomposites. Science 277: 1232-1237 (1997).
Demeshkina N. et al. Interactions of the ribosome with mRNA and tRNA Current Opinion in Structural Biology 20(3):325-332 (2010).
Denardo S.J. et al. Enhanced Therapeutic Index of Radioimmunotherapy (RIT) in Prostate Cancer Patients Comparison of Radiation Dosimetry for 14710-Tetraazacyclododecane- NN'N"N"-Tetraacetic Acid (DOTA)-Peptide versus 2IT-DOTA Monoclonal Antibody Linkage for RIT1 Clin. Cancer Res. 9: 3665s (2003).
Dern R.J. et al. Toxicity studies of pyrimethamine (daraprim). The American Journal of Tropical Medicine and Hygiene 4(2):217-220 (1955).
Deshmukh H. M and Huang L. Liposome and polylysine mediated gene therapy. New Journal of Chemistry 21:113-124 (1997).
Discher B.M. et al. Polymersomes: tough vesicles made from diblock copolymers. Science 284(5417):1143-1146 (1999).
Discher D.E. and Eisenberg A. Polymer vesicles. Science 297(5583):967-973. Review (2002).
Dokka et al. "Oxygen Radical-Mediated Pulmonary Toxicity Induced by Some Cationic Liposomes" Pharmaceutical Research Pharmaceutical Research 17(5): 521-525 (2000).
Dong Y. et al. Lipopeptide nanoparticles for potent and selective siRNA delivery in rodents and nonhuman primates Proceedings of the National Academy of Sciences 111(11): 3955-3960 (2014).
Driscoll K.E. et al. Intratracheal instillation as an exposure technique for the evaluation of respiratory tract toxicity: uses and limitations Toxicol. Sci. 55(1): 24-35 (2000).
Drummond D.C. et al. Optimizing Liposomes for Delivery of Chemotherapeutic Agents to Solid Tumors Pharmacological Reviews 51(4): 691-743 (1999).
Dwarki V. et al. Cationic liposome-mediated RNA transfection Methods in Enzymology 217:644-654 (1993).
Elbashir S.M. et al. RNA interference is mediated by 21- and 22-nucleotide RNAs. Genes & Development 15: 188-200 (2001).
Elton C. The Next Next Big Thing Boston Magazine pp. 106-118 (Mar. 2013).
Emlen W. et al. Effect of DNA size and strandedness on the in vivo clearance and organ localization of DNA Clinical & Experimental Immunology 56:185-192 (1984).
Eon-Duval A. et al. Removal of RNA impurities by tangential flow filtration in an RNase-free plasmid DNA purification process Analytical Biochemistry 316(1):66-73 (2003).
Ernst N. et al. Interaction of Liposomal and Polycationic Transfection Complexes with Pulmonary Surfactant J. Gene. Med. 1:331-340 (1999).
Estimated Number of Animal and Plant Species on Earth http://www.factmonster.com/ipka/A0934288.html 2000-2014 3 pages (Retrieved Aug. 2, 2014).
Everard et al., "Cross-talk between Akkermansia muciniphila and intestinal epithelium controls diet-induced obesity", Proceedings of the National Academy of Sciences, vol. 110, No. 22, May 28, 2013, DOI: 10.1073/pnas.1219451110 (6 pages).
Ewert K. et al. Cationic lipid-DNA complexes for gene therapy: understanding the relationship between complex structure and gene delivery pathways at the molecular level. Current Medicinal Chemistry 11(2): 133-149 (2004).
Fath S. et al. Multiparameter RNA and Codon Optimization: A Standardized Tool to Assess and Enhance Autologous Mammalian Gene Expression PLOS One 6(3):e17596 (14 pages) 2011.
Fechter P. et al. Recognition of mRNA cap structures by viral and cellular proteins Journal of General Virology 86:1239-1249 (2005).
Feigner P.L. et al. Lipofection: A Highly Efficient Lipid-Mediated DNA-Transfection Procedure Proc. Natl. Acad. 84:7413-7417 (1987).
Felgner P.L. and Ringold G.M. Cationic liposome-mediated transfection Nature 337(6205):387-388 (1989).
Fenske D.B. and Cullis P. Liposomal nanomedicines. Expert Opinion on Drug Delivery 5(1):25-44 (2008).
Fenske David B. et al. Entrapment of Small Molecules and Nucleic Acid-Based Drugs in Liposomes Methods in Enzymology 2005 pp. 7-40 Vol. 391.

(56) References Cited

OTHER PUBLICATIONS

Fernandez V. et al. Cross Flow Filtration of RNA Extracts by Hollow Fiber Membrane Acta Biotechnologica 12(1):49-56 (1992).
Ferruti P.F. and Barbucci R. Linear amino polymers: Synthesis protonation and complex formation. Advances in Polymer Science 58:55-92 (1984).
Ferruti P.F. et al. A novel modification of poly(l-lysine) leading to a soluble cationic polymer with reduced toxicity and with potential as a transfection agent. Macromolecular Chemistry and Physics 199:2565-2575 (1998).
Fire A. et al. Potent and specific genetic interference by double-stranded RNA in Caenorhabditis elegans. Nature 391(6669):806-811 (1998).
Fischer D. et al. Effect of poly(ethylene imine) molecular weight and pegylation on organ distribution and pharmacokinetics; of polyplexes with oligodeoxynucleotides in mice Drug Metabolism and Disposition 32(9):983-92 (2004).
Fumoto et al. Targeted Gene Delivery: Importance of Administration Routes Novel Gene Therapy Approaches 3-31 (2013).
Furgeson D.Y. et al. Modified linear polyethylenimine-cholesterol conjugates for DNA complexation. Bioconjugate Chemistry 14(4):840-847 (2003).
Furgeson D.Y. et al. Novel water insoluble lipoparticulates for gene delivery. Pharmaceutical Research 19(4): 382-390 (2002).
Galipon J. et al. Stress-induced 1ncRNAs evade nuclear degradation and enter the translational machinery Genes to Cells 18(5):353-368 (2013).
Gao X. et al. A novel cationic liposome reagent for efficient transfection of mammalian cells Biochemical and Biophysical Research Communications 179(1):280-285 (1991).
Garbuzenko O.B. et al. Intratracheal Versus Intravenous Liposomal Delivery of siRNA Antisense Oligonucleotides and Anticancer Drug Pharmaceutical Research 26(2):382-394 (2009).
Geraerts M. et al. Upscaling of lentiviral vector production by tangential flow filtration Journal of Gene Medicine 7(10): 1299-1310 (2005).
Godbey W.T. et al. Size matters: molecular weight affects the efficiency of poly(ethylenimine) as a gene delivery vehicle. Journal of Biomedical Materials Research 45(3):268-275 (1998).
Gonzalez H. et al. New class of polymers for the delivery of macromolecular therapeutics. Bioconjugate Chemistry 10(6):1068-1074 (1999).
Gonzalez-Aseguinolaza G. et al. Gene therapy of liver diseases: A 2011 perspective Clinics and Research in Hepatology and Gastroenterology 35(11):699-708 (2011).
Gordon N. Ornithine transcarbamylase deficiency: a urea cycle defect European Journal of Paediatric Neurology 7:115-121 (2003).
Granstein et al., "Induction of Anti-Tumor Immunity with Epidermal cells Pulsed with Tumor-Derived RNA or Intradermal Administration of RNA", J. Investigative Dermatology, vol. 114, No. 4, Apr. 2000, pp. 632-636 (5 pages).
Grayson A.C.R et al. Biophysical and structural characterization of polyethylenimine-mediated siRNA delivery in vitro. Pharmaceutical Research 23(8): 1868-1876 (2006).
Grudzien E. et al. Novel cap analogs for in vitro synthesis of mRNAs with high translational efficiency RNA Biology 10(9):1479-1487 (2004).
Grudzien E. et al. Novel cap analogs for in vitro synthesis of mRNAs with high translational efficiency Cold Spring Harbor Laboratory Press 10(9):1479-1487 (2004).
Grunlan M.A. et al. Synthesis of 19-bis[glycidyloxypropyl]penta(1'H 1'H 2'H 2'H-perfluoroalkylmethylsiloxane)s and copolymerization with piperazine. Polymer 45:2517-2523 (2004).
Gupta U. et al. A review of in vitro-in vivo investigations on dendrimers: the novel nanoscopic drug carriers. Nanomedicine: Nanotechnology Biology and Medicine 2(2):66-73 (2006).
Gust T.C. et al. RNA-containing adenovirus/polyethylenimine transfer complexes effectively transduce dendritic cells and induce antigen-specific T cell responses The Journal of Gene Medicine 6(4): 464-470 (2004).
Guttman M. et al. Chromatin signature reveals over a thousand highly conserved large non-coding RNAs in mammals Nature 458:223-227 (2009).
Haensler J. and Szoka F. Polyamidoamine cascade polymers mediate efficient transfection of cells in culture. Bioconjugate Chemistry 4(5):372-379 (1993).
Harada-Shiba M. et al. Polyion complex micelles as vectors in gene therapy—pharmacokinetics and in vivo; gene transfer Gene Therapy 9(6):407-14 (2002).
Haskins Gene Therapy for Lysosomal Storage Disorders (LDSs) in Large Animal Models ILAR J. 50(2): 112-121 (2009).
Hata A. et al. Isolation and Characterization of the Human Ornithine Transcarbamylase Gene: Structure of the 5'-End Region Journal of Biochemistry 100:717-725 (1986).
Hattatsu Nou To Brain and Development 2007 pp. 87-92 vol. 39 No.2.
Hecker J. et al. Advances in Self-Limited Gene Expression of Protective Intracellular Proteins In-Vivo in Rat Brain Using mRNA / Cationic Lipid Complexes Anesthesia and Analgesia 86(2S):346S (1994).
Heidenreich O. et al. High Activity and Stability of Hammerhead Ribozymes Containing 2'-Modified Pyrimidine Nucleosides and Phosphorothioates The Journal of Biological Chemistry 269(3):2131-2138 (1994).
Henkin et al. Inhaled Insulin—Intrapulmonary intranasal and other routes of administration: Mechanisms of action Nutrition 26: 33-39 (2010).
Hess et al. Vaccination with mRNAs encoding tumor-associated antigens and granulocyte-macrophage colony- stimulating factor efficiently primes CTL responses but is insufficient to overcome tolerance to a model tumor/self antigen Cancer Immunology Immunotherapy: CII . (2006) 55(6): 672-83.
Heyes J et al. Cationic Lipid Saturation Influences Intracellular Delivery of Encapsulated Nucleic Acids J. Controlled Release 107:276-287 (2005).
Higman M.A. et al. The mRNA (Guanine-7-)methyltransferase Domain of the Vaccinia Virus mRNA Capping Enzyme The Journal of Biological Chemistry 269(21):14974-14981 (1994).
Hill I.R.C. et al. In vitro cytotoxicity of poly(amidoamine)s: relevance to DNA delivery. Biochimica et Biophysica Acta 1427: 161-174 (1999).
Hill J.G. et al. Enantioselective Epoxidation of Allylic Alcohols: (2S3S)-3-Propyloxiranemethanol. Organic Syntheses Collection 7: 461 (1990) and 63: 66 (1985) (8 pages).
Hillery A.M. et al. Drug Delivery and Targeting for Pharmacists and Pharmaceutical Scientists Taylor and Francis (2005).
Hoerr I. et al. In Vivo Application of RNA Leads to Induction of Specific Cytotoxic T Lymphocytes and Antibodies European Journal of Immunology 30(1):1-7 (2000).
Hofland H.E.J. et al. Formation of stable cationic lipid/DNA complexes for gene transfer. Proceedings of the National Academy of Sciences of the USA 93 (14): 7305-7309 (1996).
*Homo sapiens* galactosidase alpha (GLA) mRNA NCBI Reference Sequence NM_000169.1 Modification Date: Nov. 17, 2006.
Hope M.J. et al. Cationic Lipids Phosphatidylethanolamine and the Intracellular Delivery of Polymeric Nucleic Acid-Based Drugs. Molecular Membrane Technology 15:1-14 (1998).
Hope M.J. et al. Reduction of Liposome Size and Preparation of Unilamellar Vesicles by Extrusion Techniques In: Liposome Technology 1:123-139 (1993).
Hornung V. et al. Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich A.L. et al. Structure and Expression of a Complementary DNA for the Nuclear Coded Precursor of Human Mitochondrial Ornithine Transcarbamylase Science 224(4653):1068-1074 (1984).
Horwich A.L. et al. Targeting of Pre-Ornithine Transcarbamylase to Mitochondria: Definition of Critical Regions and Residues in the Leader Peptide Cell 44:451-459 (1986).
Howard K.A. Delivery of RNA interference therapeutics using polycation-based nanoparticles. Advanced Drug Delivery Reviews 61: 710-720 (2009).

(56) References Cited

OTHER PUBLICATIONS

Huang Z. et al. Thiocholesterol-based lipids for ordered assembly of bioresponsive gene carriers Molecular Therapy 11(3):409-417 (2005).
Huttenhofer A. and Noller H. Footprinting mRNA-ribosome complexes with chemical probes The EMBO Journal 13(16):3892-3901 (1994).
Immordino et al. "Stealth liposomes: review of the basic science rationale and clinical applications existing and potential" International Journal of Nanomedicine 1(3):297-315 (2006).
Incani V. et al. Lipid and hydrophobic modification of cationic carriers on route to superior gene vectors. Soft Matter 6: 2124-2138 (2010).
International Preliminary Report on Patentability for PCT/US2010/058457 12 pages (Jun. 14, 2012).
International Search Report for PCT/US2010/58457 4 pages (May 6, 2011).
International Search Report for PCT/US2011/62459 3 pages (Apr. 11, 2012).
International Search Report for PCT/US2012/041663 4 pages (Oct. 8, 2012).
International Search Report for PCT/US2012/41724 5 pages (Oct. 25, 2012).
International Search Report for PCT/US2013/034602 2 pages (Jun. 17, 2013).
International Search Report for PCT/US2013/034604 4 pages (Jun. 17, 2013).
International Search Report for PCT/US2013/044769 4 pages (Nov. 12, 2013).
International Search Report for PCT/US2013/044771 6 pages (Nov. 1, 2013).
International Search Report for PCT/US2013/073672 6 pages (Mar. 3, 2014).
International Search Report for PCT/US2014/027422 5 pages (Jul. 31, 2014).
International Search Report for PCT/US2014/027585 3 pages (Jul. 14, 2014).
International Search Report for PCT/US2014/027587 6 pages (Jul. 24, 2014).
International Search Report for PCT/US2014/027602 6 pages (Jul. 28, 2014).
International Search Report for PCT/US2014/027717 5 pages (Jul. 16, 2014).
International Search Report for PCT/US2014/028330 5 pages (Jul. 22, 2014).
International Search Report for PCT/US2014/028441 6 pages (Jul. 22, 2014).
International Search Report for PCT/US2014/028498 5 pages (Jul. 28, 2014).
International Search Report for PCT/US2014/028849 6 pages (Jul. 17, 2015).
International Search Report for PCT/US2014/061786 6 pages (Feb. 6, 2015).
International Search Report for PCT/US2014/061793 4 pages (Feb. 6, 2015).
International Search Report for PCT/US2014/061830 5 pages (Feb. 4, 2015).
International Search Report for PCT/US2014/061841 6 pages (Feb. 24, 2015).
International Search Report for PCT/US2015/021403 4 pages (Jun. 15, 2015).
International Search Report for PCT/US2015/039004 4 pages (Oct. 6, 2015).
International Search Report for PCT/US2015/27563 5 pages (Sep. 18, 2015).
Jakobsen K. et al. Purification of MRNA Directly From Crude Plant Tissues in 15 Minutes Using Magnetic Oligo DT Microsheres Nucleic Acids Research 18(12):3669 (1990).
Jeffs L.B. et al. A scalable extrusion-free method for efficient liposomal encapsulation of plasmid DNA Pharmacol. Res. 22(3): 362-372 (2005).
Jemielity J. et al. Novel "anti-reverse" cap analogs with superior translational properties Cold Spring Harbor Laboratory Press 9(9):1108-1122 (2003).
Jia S. et al. "Eradication of osteosarcoma lung metastases following intranasal interleukin-12 gene therapy using a nonviral polyethylenimine vector" Cancer Gene Therapy 9(3): 260-266 (2002).
Jiang G. et al. Hyaluronic acid-polyethyleneimine conjugate for target specific intracellular delivery of siRNA. Biopolymers 89 (7): 635-642 (2008).
Jiang M. et al. Electrochemically controlled release of lipid/DNA complexes: a new tool for synthetic gene delivery system. Electrochemistry Communications (6): 576-582 (2004).
Jiang S. and Cao Z. Ultralow-fouling functionalizable and hydrolyzable zwitterionic materials and their derivatives for biological applications. Advanced Materials 22(9):920-932 (2010).
Jolck R.I. et al. Solid-phase synthesis of PEGylated lipopeptides using click chemistry. Bioconjugate Chemistry 21(5):807-810 (2010).
Jon S. et al. Degradable poly(amino alcohol esters) as potential DNA vectors with low cytotoxicity. Biomacromolecules 4(6): 1759-1762 (2003).
Jones G. et al. Duplex- and Triplex-Forming Properties of 4'-Thio-Modified Oligodeoxynucleotides Bioorganic & Medicinal Chemistry Letters 7(10):1275-1278 (1997).
Journal of the Japanese Society of Internal Medicine 2009 pp. 875-882 vol. 98 No.4.
Kabanov A.V. and Kabanov V.A. DNA complexes with polycations for the delivery of genetic material into cells. Bioconjugate Chemistry 6(1): 7-20 (1995).
Kamath S. et al. Surface chemistry influences implant-mediated host tissue responses. Journal of Biomedical Materials Research A 86(3):617-626 (2007).
Kariko et al., "Generating the optimal mRNA for therapy: HPLC purification eliminates immune activation and improves translation of nucleoside-modified, protein-encoding mRNA", Nucleic Acids Research, vol. 39, No. 21, 2011, DOI: 10.1093/nar/gkr695 (10 pages).
Kariko et al. Molecular Therapy (2008) 16(11): 1833-40.
Kariko K. et al. In vivo protein expression from mRNA delivered into adult rat brain Journal of Neuroscience Methods 105:77-86 (2001).
Kasuya T. et al. In Vivo Delivery of Bionanocapsules Displaying *Phaseolus vulgaris* Agglutinin-$L_4$ Isolectin to Malignant Tumors Overexpressing N-Acetylglucosaminyltransferase V Human Gene Therapy 19:887-895 (2008).
Kaur N. et al. A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur T. et al. Addressing the Challenge: Current and Future Directions in Ovarian Cancer Therapy Current Gene Therapy 9: 434-458 (2009).
Kiew L.V. et al. Effect of antisense oligodeoxynucleotides for ICAM-1 on renal ischaemia-reperfusion injury in the anaesthetised rat The Journal of Physiology 557(3):981-989 (2004).
Kim S.H. et al. Comparative evaluation of target-specific GFP gene silencing efficiencies for antisense ODN synthetic siRNA and siRNA plasmid complexed with PEI-PEG-FOL conjugate. Bioconjugate Chemistry 17(1): 241-244 (2006).
Kim T. et al. Synthesis of biodegradable cross-linked poly(beta-amino ester) for gene delivery and its modification inducing enhanced transfection efficiency and stepwise degradation. Bioconjugate Chemistry 16(5):1140-1148 (2005).
Klibanov A. et al. Amphipathic polyethyleneglycols effectively prolong the circulation time of liposomes. Federation of European Biochemical Societies 268 (1): 235-237 (1990).
Kober L. et al. Optimized Signal Peptides for the Development of High Expressing CHO Cell Lines Biotechnol. Bioeng. 110:1164-1173 (2012).
Kodama K. et al. The Features and Shortcomings for Gene Delivery of Current Non-Viral Carriers Current Medicinal Chemistry 13: 2155-2161 (2006).

(56) References Cited

OTHER PUBLICATIONS

Kore A. and Charles I. Synthesis and evaluation of 2'-O-allyl substituted dinucleotide cap analog for mRNA translation Bioorganics & Medicinal Chemistry 18:8061-8065 (2010).
Kore A. and Shanmugasundaram M. Synthesis and biological evaluation of trimethyl- substituted cap analogs Bioorganic & Medicinal Chemistry 18:880-884 (2008).
Kormann M.S.D. et al. Expression of therapeutic proteins after delivery of chemically modified mRNA in mice Nature Biotechnology 29(2):154-157 (2011).
Koynova et al., "Recent patents in 1-10 cationic lipid carriers for delivery of nucleic acids", Recent Patents On DNA & Gene Sequences, Bentham Science, United Arab Emirates, vol. 5, No. 1, Jan. 1, 2011, pp. 8-27, DOI: 10.2174/187221511794839255.
Kozak M. An analysis of 5'-noncoding sequences from 699 vertebrate messenger RNAs Nucleic Acid Research 15(20):8125-8148 (1987).
Krieg P.A. et al. In vitro RNA synthesis with SP6 Rna polymerase Methods in Enzymology 155:397-415 (1987).
Kubo et al. Mismatch Repair Protein Deficiency Is a Risk Factor for Aberrant Expression of HLA Class I Molecules: A Putative "Adaptive Immune Escape" Phenomenon Anticancer Res. 37(3): 1289-1295 (2017).
Kvasnica M. et al. Platinum(II) complexes with steroidal esters of L-methionine and L-histidine: Synthesis characterization and cytotoxic activity Bioorganic & Medicinal Chemistry 16:3704-3713 (2008).
Lam J.K.W et al. Pulmonary delivery of therapeutic siRNA Advanced Drug Delivery Reviews (2011).
Lasic D.D. et al. Gelation of liposome interior: A novel method for drug encapsulation FEBS 312(23):255-258 (1992).
Lasic D.D. Novel applications of liposomes Trends in Biotechnology 16:307-321 (1998).
Lee S. et al. Stability and cellular uptake of polymerized siRNA (poly-SiRNA)/polyethylenimine (PEI) complexes for efficient gene silencing. Journal of Controlled Release 141: 339-346 (2010).
Li L. et al. Preparation and Gene Delivery of Alkaline Amino Acids-Based Cationic Liposomes Archives of Pharmaceutical Research 31(7):924-931 (2008).
Li S. et al. In vivo gene transfer via intravenous administration of cationic lipid-protamine-DNA (LPD) complexes Gene Therapy 4:891-900 (1997).
Li S.D. et al. Nanoparticles Evading The Reticuloendothelial System: Role of The Supported Bilayer; Biochim Biophys Acta. Oct. 2009; 1788(10): 2259-2266.
Li W. et al. Lipid-based Nanoparticles for Nucleic Acid Delivery Pharmaceutical Research 24(3):438-449 (2007).
Li Yingfu et al. Kinetics of RNA Degradation by Specific Base Catalysis of Transesterification Involving the 2'-Hydroxyl Group J. Am. Chem. Soc. Feb. 1999 pp. 5364-5372 vol. 121.
Liebhaber S.A. et al. Translation inhibition by an mRNA coding region secondary structure is determined by its proximity to the AUG initiation codon Journal of Molecular Biology 226(3):609-621 (1992).
Lim Y. et al. A self-destroying polycationic polymer: biodegradable poly(4-hydroxy-I-proline ester). Journal of American Chemical Society 121: 5633-5639 (1999).
Lindgren V. et al. Human Ornithine Transcarbamylase Locus Mapped to Band Xp21.1 Near the Duchenne Muscular Dystrophy Locus Science 226(2675):698-700 (1984).
Liu X. et al. COStar: a D-star Lite-based Dynamic Search Algorithm for Codon Optimization Journal of Theoretical Biology 344:19-30 (2014).
Liu Y. et al. Designer Lipids Advance Systemic siRNA Delivery Molecular Therapy 18(4):669-670 (2010).
Liu Y. et al. Factors influencing the efficiency of cationic liposome-mediated intravenous gene delivery Nature Biotechnology 15:167-173 (1997).
Lo K-M et al. High level expression and secretion of Fc-X fusion proteins in mammalian cells Protein Engineering 11(6):495-500 (1998).
Lorenzi et al. Intranasal vaccination with messenger RNA as a new approach in gene therapy: use against tuberculosis BMC Biotechology (Oct. 20, 2010) 10:77: pp. 1-11.
Love K.T. et al. Lipid-like materials for low-dose in vivo gene silencing. Proceedings of the National Academy of Sciences of the USA 107 (5): 1864-1869 (2010).
Lu et al., "Efficient siRNA selection using hybridization thermodynamics", Nucleic Acids Research, vol. 36, No. 2, 2008, pp. 640-647, DOI: 10.1093/nar/gkm920 (8 pages).
Lu D. et al. Optimization of methods to achieve mRNA-mediated transfection of tumor cells in vitro and in vivo employing cationic liposome vectors Cancer Gene Therapy 1(4):245-52 (1994).
Lukyanov A.N. and Torchilin V.P. Micelles from lipid derivatives of water-soluble polymers as delivery systems for poorly soluble drugs. Advanced Drug Delivery Reviews 56: 1273-1289 (2004).
Luo D. and Saltzman M. Synthetic DNA delivery systems. Nature Biotechnology 18: 33-37. Review (2000).
Lynn D.M. and Langer R. Degradable Poly(ß-amino esters) :? Synthesis Characterization and Self-Assembly with Plasmid DNA. Journal of American Chemical Society 122(44): 10761-10768 (2000).
Lynn D.M. et al. Accelerated discovery of synthetic transfection vectors: parallel synthesis and screening of a degradable polymer library. Journal of American Chemical Society 123(33): 8155-8156 (2001).
Lynn D.M. et al. pH-Responsive Polymer Microspheres: Rapid Release of Encapsulated Material within the Range of Intracellular pH. Angewandte Chemie International Edition 40(9): 1707-1710 (2001).
Ma M. et al. Development of Cationic Polymer Coatings to Regulate Foreign Body Responses. Advanced Healthcare Materials 23: H189-H194. Reviews (2011).
MacLachlan I. Lipid nanoparticle-mediated delivery of messenger RNA 1st International mRNA Health Conference; Tubingen Germany (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>.
Maeda-Mamiya R. et al. In vivo gene delivery by cationic tetraamino; fullerene. Proceedings of National Academy of Sciences U S A 107(12):5339-44 (2010).
Malone R.W. et al. Cationic liposome-mediated RNA transfection PNAS 86:6077-6081 (1989).
Mammal http://en.wikipedia.org/wiki/Mammal 2007 Pearson Education NY NY Author unknown (Source: The international union for conservation of nature and natural resources) 2 pages (Retrieved Aug. 2, 2014).
Mansour H.M. et al. Nanomedicine in pulmonary delivery International Journal of Nanomedicine 4:299-319 (2009).
Margus H. et al. Cell-penetrating peptides as versatile vehicles for oligonucleotide delivery. Molecular Therapy 20 (3): 525-533 (2012).
Martell A.E. and Chaberek S. The Preparation and the Properties of Some NN'- Disubstituted-ethylenediaminedipropionic Acids. Journal of the American Chemical Society 72: 5357-5361 (1950).
Martinon et al. Induction of virus-specific cytotoxic T lymphocytes in vivo by liposome- entrapped mRNA European Journal of Immunology (1993) 23(7): 1719-22.
Mathiowitz E. and Langer R. Polyanhydride microspheres as drug carriers I. Hot-melt microencapsulation. Journal of Controlled Release 5: 13-22 (1987).
Mathiowitz E. et al. Novel microcapsules for delivery systems. Reactive Polymers 6: 275-283 (1987).
Mathiowitz E. et al. Polyanhydride microspheres as drug carriers II. Microencapsulation by solvent removal. Journal of Applied Polymer Sciences 35: 755-774 (1988).
McCracken S. et al. 5'-Capping Enzymes are Targeted to Pre-MRNA by Binding to the Phosphorylated Carboxy-Terminal Domain of RNA Polymerase II Genes and Development 22(24):3306-3318 (1997).
McIvor R. S. Therapeutic Delivery of mRNA: The Medium is the Message Molecular Therapy 19(5):822-823 (2011).

(56) References Cited

OTHER PUBLICATIONS

Melton D.A. et al. Efficient in vitro synthesis of biologically active RNA and RNA hybridization probes from; plasmids containing a bacteriophage SP6 promoter Nucleic Acids Research 12(18):7035-56 (1984).
Mendelsohn J.D. et al. Rational design of cytophilic and cytophobic polyelectrolyte multilayer thin films. Biomacromolecules 4(1): 96-106 (2003).
Merkel O.M. et al. Nonviral Pulmonary Delivery of siRNA Accounts of Chemical Research 10 pages (2011).
Merten O. et al. Large-Scale Manufacture and Characterization of a Lentiviral Vector Produced for Clinical Ex Vivo Gene Therapy Application Human Gene Therapy 22(3):343-356 (2011).
Meyer et al. "Cationic liposomes coated with polyethylene glycol as carriers for oligonucleotides" Journal of Biological Chemistry 273: 15621-15627 (1998).
Miller A. Cationic Liposomes for Gene Therapy. Angewandte Chemie International Edition 37: 1768-1785 (1998).
Mockey et al. "mRNA-based cancer vaccine: prevention of B16 melanoma progression and metastasis by systemic injection of MART1 mRNA histidylated lipopolyplexes", Cancer Gene Therapy, vol. 14, Jun. 22, 2007, pp. 802-814 (13 pages).
Monck et al. Stablized Plasmid-Lipid Particles: Pharmacokinetics and Plasmid Delivery to Distal Tumors following Intravenous Injection J. Drug Target 7(6): 439-452 (2000).
Monia B.P. et al. Evaluation of 2'-Modified Oligonucleotides Containing 2'-Deoxy Gaps as Antisense Inhibitors of Gene Epression The Journal of Biological Chemistry 268(19): 14514-14522 (1993).
Montana et al., "Employment of Cationic Solid-Lipid Nanoparticles as RNA Carriers", Bioconjugate Chem., vol. 18, 2007, pp. 302-308, DOI: 10.1021/bc0601166 (7 pages).
Morrissey D.V. et al. Potent and Persistent in vivo Anti-HBV Activity of Chemically Modified siRNAs Nat. Biotechnol. 23(8): 1003-1007 (2005).
Nakada et al., "mRNA induces RANTES production in trophoblast cells via TLR3 only when delivered intracellularly using lipid membrane encapsulation", Placenta, vol. 32, 2011, pp. 500-505, DOI: 10.1016/j.placenta.2011.04.011 (6 pages).
Narang A.S. et al. Cationic lipids with increased DNA binding affinity for nonviral gene transfer in dividing and nondividing cells. Bioconjugate Chemistry 16(1): 156-168 (2005).
Navarro G. et al. Phospholipid-polyethylenimine conjugate-based micelle-like nanoparticles for siRNA delivery. Drug Delivery and Translational Research 1: 25-33 (2011).
Neamnark A. et al. Aliphatic lipid substitution on 2 kDa polyethylenimine improves plasmid delivery and transgene expression. Molecular Pharmaceutics 6(6): 1798-1815 (2009).
Ng J. et al. LincRNAs join the pluripotency alliance Nature Genetics 42:1035-1036 (2010).
Nguyen D.N. et al. A novel high-throughput cell-based method for integrated quantification of type I interferons and in vitro screening of immunostimulatory RNA drug delivery. Biotechnology and Bioengineering 103(4): 664-675 (2009).
Nguyen D.N. et al. Drug delivery-mediated control of RNA immunostimulation. Molecular Therapy 17(9): 1555-1562 (2009).
Nojima T. et al. The Interaction between Cap-binding Complex and RNA Export Factor is Required for Intronless mRNA Export Journal of Biological Chemistry 282(21): 15645-15651 (2007).
Nori A. et al. Tat-conjugated synthetic macromolecules facilitate cytoplasmic drug delivery to human ovarian carcinoma cells Bioconj. Chem. 14(1): 44-50 (2003).
Okumura K. et al. Bax mRNA therapy using cationic liposomes for human malignant melanoma The Journal of Gene Medicine 10:910-917 (2008).
Optiz Lennart et al. Impact of RNA Degradation on Gene Expression Profiling BMC Medical Genomics 2010 pp. 1-14 3:36 http://www.biooscientific.com/AIR-DNA-Fragmentation-Kit.
Ostro et al., "Evidence for translation of rabbit globin mRNA after liposome-mediated insertion into a human cell line", Nature, vol. 274, Aug. 31, 1978, pp. 921-923 (3 pages).
Otsuka Y. et al. Identification of a Cytoplasmic Complex That Adds a Cap onto 5'- Monophosphate RNA Molecular and Cellular Biology 29(8):2155-2167 (2009).
Ozawa Keeiya M.D. Ph.D. Gene Therapy Using AAV 2007 pp. 47-56 Division of Hematology Department of Medicine Division of Gerretic Therapeutics Center for Molecular Medicine Jich1 Medical University 3311-1 Yakuhiji Shimotsuke-shi Tochigi 329--0198 Japan.
Ozer A. Alternative applications for drug delivery: nasal and pulmonary routes Nanomaterials and Nanosystems for Biomedical Applications M.R. Mozafari (ed.): 99-112 (2007).
Painter H. et al Topical Delivery of mRNA to the Murine Lung and Nasal Epithelium Gene Medicine Group and the Medical Informatics Unit Nuffield Department of Clinical Laboratory Sciences University of Oxford 1 page.
Painter H. et al. Topical Delivery of mRNA to the Murine Lung and Nasal Epithelium Molecular Therapy 9:S187 (2004).
Painter H. An Investigation of mRNA as a Gene Transfer Agent Gene Medicine Research Group Nuffield Department of Clinical Laboratory Sciences and Merton College University of Oxford 1-282 (2007).
Painter H. An Investigation of mRNA as a Gene Transfer Agent Oxford University GeneMedicine Abstract Only 1 page (2007).
Parrish D.A. and Mathias L.J. Five- and six-membered ring opening of pyroglutamic diketopiperazine. Journal of Organic Chemistry 67(6): 1820-1826 (2002).
Pathak et al. Nano-vectors for efficient liver specific gene transfer Int. J. Nanomedicine 3(1): 31-49 (2008).
Patton J. Market Trends in Pulmonary Therapies Trends and Opportunities VI: 372-377.
Paulus C. and Nevels M. The Human Cytomegalovirus Major Immediate-Early Proteins as Antagonists of Intrinsic and Innate Antiviral Host Responses Viruses 1:760-779 (2009).
Peer et al., "Systemic Leukocyte-Directed siRNA Delivery Revealing Cyclin D1 as an Anti-Inflammatory Target", Science, vol. 319, Feb. 1, 2008, pp. 627-630 (5 pages).
Peppas N.A. et al. Hydrogels in Biology and Medicine: From Molecular Principles to Bionanotechnology. Advanced Materials 18: 1345-1360 (2006).
Philipp A. et al. Hydrophobically modified oligoethylenimines as highly efficient transfection agents for siRNA delivery. Bioconjugate Chemistry 20(11): 2055-2061 (2009).
Pons M. et al. Liposomes obtained by the ethanol injection method Int. J. Pharm. 95: 51-56. (1993).
Prata C.A. et al. Lipophilic peptides for gene delivery. Bioconjugate Chemistry 19(2): 418-420 (2008).
Pray et al., "Eukaryotic Genome Complexity", Nature Education, vol. 1, No. 1, 2008, pp. 96 (4 pages).
Probst J. et al. Spontaneous cellular uptake of exogenous messenger RNA in vivo is nucleic acid-specific saturable and ion dependent Gene Therapy 14:1175-1180 (2007).
Promega PolyATtract mRNA Isolation Systems Instructions for Use of Products Z5200 Z5210 Z2300 and Z5310 Technical Manual (2012).
Putnam D. Polymers for gene delivery across length scales. Nature Materials 5: 439-451 (2006).
Putnam D. and Langer R. Poly(4-hydroxy-I-proline ester): Low-Temperature Polycondensation and Plasmid DNA Complexation. Macromolecules 32(11): 3658-3662 (1999).
Qiagen Oligotex Handbook Second Edition (2002).
Rabinovich P.M. et al. Synthetic Messenger RNA as a Tool for Gene Therapy Human Gene Therapy 17:1027-1035 (2006).
Ramaswamy S. et al. "Systemic delivery of factor IX messenger RNA for protein replacement therapy" Proceedings of the National Academy of Sciences of the United States of America 114(10):E1941-E1950 (Mar. 7, 2017).
Raney et al. The effect of circulation lifetime and drug-to-lipid ratio of intravenously administered lipid nanoparticles on the biodistribution and immunostimulatory activity of encapsulated CpG-ODN J. Drug Target 16(7): 564-577 (2008).
Raper S.E. et al. Developing adenoviral-mediated in vivo gene therapy for ornithine transcarbamylase deficiency Journal of Inherited Metabolic Disease 21:119-137 (1998).

(56) References Cited

OTHER PUBLICATIONS

Ratajczak J. et al. Membrane-derived microvesicles: important and underappreciated mediators of cell-to-cell communication Leukemia 20:1487-1495 (2006).
Ratner B.D. and Bryant S. Biomaterials: where we have been and where we are going. Annual Review of Biomedical Engineering 6: 41-75 (2004).
Reddy A. et al. The Effect of Labour and Placental Separation on the Shedding of Syncytiotrophoblast Microparticles Cell-free DNA and mRNA in Normal Pregnancy and Pre-eclampsia Placenta 29:942-949 (2008).
Rejman J. et al. Characterization and transfection properties of lipoplexes stabilized with novel exchangeable polyethylene glycol-lipid conjugates Biochimica et Biophysica Acta 1660:41-52 (2004).
Rejman et al., "mRNA transfection of cervical carcinoma and mesenchymal stem cells mediated by cationic carriers", Journal of Controlled Release, vol. 147, 2010, pp. 385-391, DOI: 10.1016/j.jconrel.2010.07.124 (7 pages).
Remington: The Science and Practice of Pharmacy 21st Edition Philadelphia PA. Lippincott Williams & Wilkins (2005).
Riordan Thomas G. Md. Formulations and Nebulizer Performance Respiratory Care Nov. 2002 pp. 1305-1312 vol. 47 No. 11.
Robinson et al. "Lipid Nanoparticle-Delivered Chemically Modified mRNA Restores Chloride Secretion in Cystic Fibrosis" Molecular Therapy 26(8): 1-13 (2018).
Rosenecker J. et al. Gene Therapy for Cystic Fibrosis Lung Disease: Current Status and Future Perspectives Curr. Opin. Mol. Ther. 8:439-445 (2006).
Rosenecker J. et al. Interaction of Bronchoalveolar Lavage Fluid with Polyplexes and Lipoplexes: Analysing the Role of Proteins and Glycoproteins J. Gene. Med. 5:49-60 (2003).
Rowe S.M. et al. Cystic Fibrosis New Engl. J. Med. 352:1992-2001 (2005).
Rudolph C. et al. Aerosolized Nanogram Quantities of Plasmid DNA Mediate Highly Efficient Gene Delivery to Mouse Airway Epithelium Molecular Therapy 12(3): 493-501 (2005).
Rudolph C. et al. Methodological optimization of polyethylenimine (PEI)-based gene delivery to the lungs of mice via aerosol application Journal of Gene Medicine 7(1): 59-66 (2005).
Ryng S. et al. Synthesis and structure elucidation of 5-aminomethinimino-3-methyl-4- isoxazolecarboxylic acid phenylamides and their immunological activity. Arch. Pharm. Pharm. Med. Chem 330(11):319-26 (1997).
Sahay G. et al. Endocytosis of nanomedicines. Journal of Controlled Release 145: 182-195 (2010).
Sakiyama-Elbert S.E. and Hubbell J.A. Functional Biomaterials: Design of Novel Biomaterials. Annual Review of Materials Research 31: 183-201 (2001).
Sambrook Joseph et al. Fragmentation of DNA by Nebulization Commonly Used Techniques in Molecular Cloning Appendix 8 in Molecular Cloning 2001-2006 5 Pages. vol. 3 3rd edition (eds. Sambrook and Russell). Cold Spring Harbor Laboratory Press Cold Spring Harbor NY USA.
Scherphof et al. Uptake of Liposomes by Rat and Mouse Hepatocytes and Kupffer Cells Biol. Cell 47: 47-58 (1983).
Schnierle B.S. et al. Cap-specific mRNA (nucleoside-O2'-)-methyltransferase and poly(A) polymerase stimulatory activities of vaccinia virus are mediated by a single protein Proceedings of the National Academy of Sciences 89:2897-2901 (1992).
Schreier H. The new frontier: gene and oligonucleotide therapy Pharmaceutica Acta Helvetiae 68(3):145-159 (1994).
Semple S.C. et al. Rational design of cationic lipids for siRNA delivery Nature Biotechnology 28(2): 172-176 (2010).
Shchori E. Poly(secondary Amine)s from Diacrylates and Diamines. Journal of Polymer Science 21(6):413-15 (1983).
Sherwood R.F. Advanced drug delivery reviews: enzyme prodrug therapy Adv. Drug Del. Rev. 22: 269-288 (1996).
Shimada A. et al. Translocation Pathway of the Intratracheally Instilled Ultrafine Particles from the Lung into the Blood Circulation in the Mouse Toxicologic Pathology 34:949-957 (2006).
Siegwart D.J. et al. Combinatorial synthesis of chemically diverse core-shell nanoparticles for intracellular delivery. Proceedings of the National Academy of the Sciences of the USA 108(32):12996-123001 (2011).
Sigurgeirsson Benjamin et al. Sequencing Degraded RNA Addressed by 3' Tag Counting PLOS One Mar. 2014 pp. 1-11 vol. 9 Issue 3 e91851.
Smisterova J. et al. Molecular Shape of the Cationic Lipid Controls the Structure of Cationic Lipid/Dioleylphosphatidylethanolamine-DNA Complexes and the Efficiency of Gene Delivery The Journal of Biological Chemistry 276(50):47615-47622 (2001).
Stern L. et al. A novel antitumor prodrug platform designed to be cleaved by the endoprotease legumain Bioconj. Chem. 20: 500-510 (2009).
Su X. et al. Cytosolic Delivery Mediated Via Electrostatic Surface Binding of mRNA To Degradable Lipid-Coated Polymeric Nanoparticles Polymer Preprints 51(2):668-669 (2010).
Su X. et al. In Vitro and in Vivo mRNA Delivery Using Lipid-Enveloped pH-Responsive Polymer Nanoparticles Molecular Pharmaceutics 8(3):774-787 (2011).
Suri M. et al. Genetics for Pediatricians Remedica Publishing (2005).
Szoka F. and Papahadjopoulos D. Comparative properties and methods of preparation of lipid vesicles (liposomes). Annual Review of Biophysics Bioengineering 9: 467-508 (1980).
Tagawa M. et al. Gene expression and active virus replication in the liver after injection of duck hepatitis B virus DNA into the peripheral vein of ducklings Journal of Hepatology 24:328-334 (1996).
Takahashi Y. et al. Development of safe and effective nonviral gene therapy by eliminating CpG motifs from plasmid DNA vector Frontiers in Bioscience S4: 133-141 (2012).
Tan S. et al. Engineering Nanocarriers for siRNA Delivery. Small 7(7): 841-856 (2011).
Tang F. and Hughes J et al. Introduction of a Disulfide Bond into a Cationic Lipid Enhances Transgene Expression of Plasmid DNA Biochemical and Biophysical Research Communications 242(1):141-145 (1998).
Tang M.X. et al. In vitro gene delivery by degraded polyamidoamine dendrimers. Bioconjugate Chemistry 7(6): 703-714 (1996).
Tarcha P.J. et al. Synthesis and characterization of chemically condensed oligoethylenimine containing beta-aminopropionamide linkages for siRNA delivery. Biomaterials 28: 3731-3740 (2007).
Tavernier G. et al. mRNA as gene therapeutic: How to control protein expression Journal of Controlled Release 150:238-247 (2011).
Tcherepanova I. et al. Ectopic expression of a truncated CD40L protein from synthetic post-transcriptionally capped RNA in dendritic cells induces high levels of IL-12 secretion BMC Molecular Biology 9(1): pp. 1-13 (2008).
Thess A. et al. "Sequence-engineered mRNA Without Chemical Nucleoside Modifications Enables an Effective Protein Therapy in Large Animals" Molecular Therapy 23(9):1456-64 (Sep. 2015).
Theus S. and Liarakos C. A Simple Assay for Determining the Capping Efficiencies of RNA Polymerases Used for In Vitro Transcription BioChromatography 9(5):610-614 (1990).
Third Party Preissuance Submission Under 37 CFR § 1.290 (Oct. 25, 2013).
Thomas C. E. et al. Progress and problems with the use of viral vectors for gene therapy Nature Reviews/Genetics 4: 346-358 (2003).
Thompson P.E. et al. Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki B.E. et al. Protease-mediated fragmentation of p-amidobenzyl ethers: a new strategy for the activation of anticancer prodrugs J. Org. Chem. 67(6): 1866-1872 (2002).
Tolmachov Oleg E. et al. Methods of Transfection with Messenger RNA Gene Vectors Gene Therapy-Principles and Challenges 2015 pp. 1-55 Chapter 2. http://dx.doi.org/10.5772/61688.
Tranchant I. et al. Physicochemical optimisation of plasmid delivery by cationic lipids. Journal of Gene Medicine 6: S24-S35 (2004).

(56) References Cited

OTHER PUBLICATIONS

Tsui N.B. et al. Stability of endogenous and added RNA in blood specimens serum and plasma Clinical Chemistry 48(10):1647-53 (2002).
Tsvetkov D.E. et al. Neoglycoconjugates based on dendrimeric poly(aminoamides). Russian Journal of Bioorganic Chemistry 28(6): 470-486 (2002).
Tuschl T. et al. Targeted mRNA degradation by double-stranded RNA in vitro Genes and Development 13(24): 3191-7 (1999).
Urban-Klein B. et al. RNAi-mediated gene-targeting through systemic application of Polyethylenimine (PEI)-complexed siRNA in vivo. Gene Therapy 12(5): 461-466 (2005).
Van Balen G.P. et al. Liposome/water lipophilicity: methods information content and pharmaceutical applications. Medicinal Research Reviews 24(3): 299-324 (2004).
Van De Wetering P. et al. Structure-activity relationships of water-soluble cationic methacrylate/methacrylamide polymers for nonviral gene delivery. Bioconjugate Chemistry 10(4): 589-597 (1999).
Van Der Gun B.T.F et al. Serum insensitive intranuclear protein delivery by the multipurpose cationic lipid Saint-2 Journal of Controlled Release 123:228-238 (2007).
Van Tendeloo V.F.I et al. mRNA-based gene transfer as a tool for gene and cell therapy Current Opinion in Molecular Therapeutics 9(5):423-431 (2007).
Vandenbroucke R.E. et al. Prolonged gene silencing in hepatoma cells and primary hepatocytes after small interfering RNA delivery with biodegradable poly(beta-amino esters). Journal of Gene Medicine 10: 783-794 (2008).
Varambally S. et al. Genomic Loss of microRNA-101 Leads to Overexpression of Histone Methyltransferase EZH2 in Cancer Science 322:1695-1699 (2008).
Veronese F.M. et al. PEG-doxorubicin conjugates: influence of polymer structure on drug release in vitro cytotoxicity biodistribution and antitumor activity Bioconj. Chem. 16(4): 775-784 (2005).
Viecelli H. et al. Gene Therapy for Hepatic Diseases Using Non-Viral Minicircle-DNA Vector Journal of Inherited Metabolic Disease 35(1):S144 (2012).
Viecelli H. et al. Gene therapy for liver diseases using non-viral minicircle-DNA vector Human Gene Therapy 23(10):A145 (2012).
Viecelli H. et al. Gene therapy for liver diseases using non-viral minicircle-DNA vector Molecular Therapy 21(1):S136 (2013).
Vomelova I. et al. Methods of RNA Purification. All Ways (Should) Lead to Rome Folia Biologica 55(6):242-251 (2009).
Von Harpe et al. Characterization of commercially available and synthesized polyethylenimines for gene delivery. Journal of Controlled Release 69(2):309-322 (2000).
Walde P. et al. Preparation of Vesicles (Liposomes). Encyclopedia of Nanoscience and Nanotechnology. Nalwa ed. American Scientific Publishers Los Angeles 9:43-79 (2004).
Wang H. et al. N-acetylgalactosamine functionalized mixed micellar nanoparticles for targeted delivery of siRNA to liver Journal of Controlled Release 166(2):106-114 (2013).
Wang Y. et al. Systemic delivery of modified mRNA encoding herpes simplex virus 1 thymidine kinase for targeted cancer gene therapy Molecular Therapy 21(2):358-367 (2013).
Wang Yaogeng et al. The Impact of Different Preservation Conditions and Freezing-Thawing Cycles on Quality of RNA DNA and Proteins in Cancer Tissue Biopreservation and Biobanking 2015 pp. 335-347 vol. 13 No. 5.
Webb M. et al. Sphinogomyeline-cholesterol liposomes significantly enhance the pharmacokinetic and therapeutic properties of vincristine in murine and human tumour models British Journal of Cancer 72(4):896-904 (1995).
Weiss et al., "Evidence for Specificity in the Encapsidation of Sindbis Virus RNAs", Journal of Virology, vol. 63, No. 12, Dec. 1989, pp. 5310-5318 (9 pages).
Werth S. et al. A low molecular weight fraction of polyethylenimine (PEI) displays increased transfection efficiency of DNA and siRNA in fresh or lyophilized complexes. Journal of Controlled Release 112: 257-270 (2006).
Wetzer B. et al. Reducible cationic lipids for gene transfer Biochem. J. 356:747-756 (2001).
White J.E. et al. Poly(hydroxyaminoethers): A New Family of Epoxy-Based Thermoplastics. Advanced Materials 12(23): 1791-1800 (2000).
White J.E. et al. Step-growth polymerization of 1011-epoxyundecanoic acid. Synthesis and properties of a new hydroxy-functionalized thermopastic polyester. Advanced Materials 48: 3990-3998 (2007).
Whitehead K.A. et al. Knocking down barriers: advances in siRNA delivery. Nature Reviews Drug Discovery 8(2): 129-139 (2009).
Wiehe J.M. et al. mRNA-mediated gene delivery into human progenitor cells promotes highly efficient protein expression Journal of Cellular and Molecular Medicine 11(3):521-530 (2007).
Williams D. et al. A simple highly efficient method for heterologous expression in mammalian primary neurons using cationic lipid-mediated mRNA transfection Frontiers in Neuroscience 4(181):1-20 (2010).
Wilson et al. Ex vivo gene therapy of familial hypercholesterolemia Hum. Gene Ther. 3(2): 179-222 (1992).
Wisse et al. The size of endothelial fenestrae in human liver sinusoids: implications for hepatocyte-directed gene transfer Gene Therapy 15: 1193-1199 (2008).
Wolf J.A. et al. Protein/Amphipathic Polyamine Complexes Enable Highly Efficient Transfection with Minimal Toxicity BioTechniques 23:139-147 (1997).
Woodle et al. Versality in lipid compositions showing prolonged circulation with sterically stabilized liposomes Biochim. Biophys. Acta 1105(2): 193-200 (1992).
Written Opinion for PCT/US2010/058457 10 pages (May 6, 2011).
Written Opinion for PCT/US2011/062459 9 pages (Apr. 11, 2012).
Written Opinion for PCT/US2012/041663 7 pages (Oct. 8, 2012).
Written Opinion for PCT/US2012/041724 11 pages (Oct. 25, 2012).
Written Opinion for PCT/US2013/034602 4 pages (Jun. 17, 2013).
Written Opinion for PCT/US2013/034604 9 pages (Jun. 17, 2013).
Written Opinion for PCT/US2013/044769 8 pages (Nov. 12, 2013).
Written Opinion for PCT/US2013/044771 7 pages (Nov. 1, 2013).
Written Opinion for PCT/US2013/073672 7 pages (Mar. 3, 2014).
Written Opinion for PCT/US2014/027422 6 pages (Jul. 31, 2014).
Written Opinion for PCT/US2014/027587 5 pages (Jul. 24, 2014).
Written Opinion for PCT/US2014/027602 7 pages (Jul. 28, 2014).
Written Opinion for PCT/US2014/027717 5 pages (Jul. 16, 2014).
Written Opinion for PCT/US2014/028330 7 pages (Jul. 22, 2014).
Written Opinion for PCT/US2014/028441 6 pages (Jul. 22, 2014).
Written Opinion for PCT/US2014/028498 6 pages (Jul. 28, 2014).
Written Opinion for PCT/US2014/028849 7 pages (Jul. 17, 2015).
Written Opinion for PCT/US2014/061786 5 pages (Feb. 6, 2015).
Written Opinion for PCT/US2014/061793 4 pages (Feb. 6, 2015).
Written Opinion for PCT/US2014/061830 7 pages (Feb. 4, 2015).
Written Opinion for PCT/US2014/061841 8 pages (Feb. 24, 2015).
Written Opinion for PCT/US2015/021403 7 pages (Jun. 15, 2015).
Written Opinion for PCT/US2015/027563 12 pages (Sep. 18, 2015).
Written Opinion for PCT/US2015/039004 8 pages (Oct. 6, 2015).
Wu et al., Modification of liposomes for liver targeting Journal of Hepatology 24(6):757-763 (1996).
Wu J. et al. Cationic lipid polymerization as a novel approach for constructing new DNA delivery agents. Bioconjugate Chemistry 12(2): 251-257 (2001).
Wurdinger et al. (2008) A secreted luciferase for ex-vivo monitoring of vivo processes Nature Methods 5(2): 171-173.
Xiong et al., "Cationic liposomes as gene delivery system: transfection efficiency and new application", Pharmazie, vol. 66, Mar. 2011, pp. 158-164, DOI: 10.1691/ph.2011.0768.
Yamamoto A. et al. Current prospects for mRNA gene delivery European Journal of Pharmaceutics and Biopharmaceutics 71:484-489 (2009).
Yamamoto Y. et al. Important Role of the Proline Residue in the Signal Sequence that Directs the Secretion of Human Lysozyme in Saccharomyces Cerevisiae Biochemistry 28:2728-2732 (1989).
Yang Tzu-Hsueh et al. Determination of RNA degradation by Capillary Electrophoresis with Cyan Light-emitted Diode-induced Fluorescence Journal of Chromatography Mar. 2012 pp. 78-84 vol. 1239 Journal Homepage: www.elsevier.com/locate/chroma.

(56) References Cited

OTHER PUBLICATIONS

Yasuda et al. Fabry Disease: Novel [alpha]-Galactosidase A 3-terminal Mutations Result in Multiple Transcripts Due to Aberrant 3-End Formation American Journal of Human Genetics 73: 162-73 (2003).
Ye X. et al. Nucleic Acids Protein Synthesis and Molecular Genetics: Prolonged Metabolic Correction in Adult Ornithine Transcarbamylase-deficient Mice with Adenoviral Vectors The Journal of Biological Chemistry 271:3639-3646 (1996).
Yokoe H. et al. Spatial dynamics of GFP-tagged proteins investigated by local fluorescence enhancement Nature Biotechnology 14(10):1252-1256 (1996).
Yoneda et al. A cell-penetrating peptidic GRP78 ligand for tumor cell-specific prodrug therapy Bioorg. Med. Chern. Lett. 18(5): 1632-1636 (2008).
Yoshioka Y. and Calvert P. Epoxy-based Electroactive Polymer Gels. Experimental Mechanics 42(4): 404-408 (2002).
Zagridullin P.H. et al. Monobasic amines. II. Cycloalkylation and hydroxyalkylation of cyclic and acyclic di- and polyamines. Journal of Organic Chemistry26(1):184-88. Russian (1990).
Zaugg H.E. et al. 3-Carboxy-25-piperazinedione and Derivatives. Journal of American Chemical Society 78(11):2626-2631 (1956).
Zauner W.et al. Polylysine-based transfection systems utilizing receptor-mediated delivery. Advanced Drug Delivery Reviews 30(1-3):97-113(1998).
Zhang L. et al. "Enhanced efficacy and limited systemic cytokine exposure with membrane-anchored interleukin-12 T-cell therapy in murine tumor models" Journal for ImmunoTherapy of Cancer 8(1): article e000210 (2020).
Zintchenko A. et al. Simple modifications of branched PEI lead to highly efficient siRNA carriers with low toxicity. Bioconjugate Chemistry 19(7):1448-1455 (2008).
Zohra et al., "Effective delivery with enhanced translational activity synergistically accelerates mRNA-based transfection", Biochemical and Biophysical Research Communications, vol. 358, 2007, pp. 373-378.
Zou S. et al. Lipid-mediated delivery of RNA is more efficient than delivery of DNA in non-dividing cells International Journal of Pharmaceutics 389(1-2):232-243 (2010).
Anderson, Michael et al., "The Effect of Different Lipid Components on the In Vitro Stability and Release Kinetics of Liposome Formulations", Drug Delivery, 11:33-39. 2004.
Authors unnamed, "How CRISPR Is Changing Cancer Research and Treatment", published by the National Cancer Institute, online at How CRISPR Is Changing Cancer Research and Treatment—NCI, 12 pages printed (Year: 2020).
Brown, William M. "rAAt (inhaled Arriva/Hyland Immuno", Current Opinion in Molecular Therapy, 8(1): 76-82, Abstract Only, 1 page, (2006).
Busby, Sharon et al., "Expression of active human factor IX in transfected cells", Nature, vol. 316, 271-273, 1985.
Crooke, S.T., "Chapter 9.3 Methods of encapsulating nucleic acids" In: "Antisense Drug Technology: Principles, Strategies, and Applications—2nd Edition", Jul. 25, 2007 (Jul. 25, 2007), CRC Press ISBN: 9780849387968 pp. 242-251.
Engelhardt, John F. et al., "Adenovirus-Mediated Transfer of the CFTR Gene to Lung of Nonhuman Primates: Biological Efficacy Study", Human Gene Therapy 4:759-769 (1993).
Graham, Michael R. et al., "Potential benefits of recombinant human growth hormone (rhGH) to athletes", Growth Hormone & IGF Research, 19 (2009) 300-307.
Hong, Joon Pio et al., "Recombinant Human Epidermal Growth Factor (EGF) to Enhance Healing for Diabetic Foot Ulcers", Annals of Plastic Surgery, 56(4) 394-98, 2006.
Lu, Zhi John et al., "Efficient siRNA selection using hybridization thermodynamics", Nucleic Acids Research, 2008, vol. 36, No. 2, 640-647.
Murphy, Samuel L. et al., "Gene therapy for haemophilia", British Journal of Haematology, 140: 479-487 (2008).
Soukharev, Serguei et al., "Expression of Factor VIII in Recombinant and Transgenic Systems", Blood Cells, Molecules and Diseases (2002), 28(2): 234-248.
Hartl et al., (2011), "Molecular chaperones in protein folding and proteostatis," Nature, 475:324-332.

* cited by examiner

5' CMV Sequence:

XCAGAUCGCCUGGAGACGCCAUCCACGCUGUUUUGACCUCCAUAGAAGACACCGGGACCGAUCCAGCCUCCGCGGC
CGGGAACGGUGCAUUGGAACGCGGAUUCCCCGUGCCAAGAGUGACUCACCGUCCUUGACACG
(SEQ ID NO: 1)

FIG. 1

3' hGH Sequence:

CGGGUGGCAUCCCUGUGACCCCUCCCCAGUGCCUCUCCUGGCCCUGGAAGUUGCCACUCCAGUGCCCACCAGCCUUG
UCCUAAUAAAAUUAAGUUGCAUC (SEQ ID NO: 2)

FIG. 2

Human erythropoietin (EPO) mRNA:

AUGGGGGUGCACGAAUGUCCUGCCUGGCUGUGGCUUCUCCUGUCCCUGCUGUCGCUCCCUCUGGGCCUCCCAGUCC
UGGGCGCCCCACCACGCCUCAUCUGUGACAGCCGAGUCCUGGAGAGGUACCUCUUGGAGGCCAAGGAGGCCGAGAA
UAUCACGACGGGCUGUGCUGAACACUGCAGCUUGAAUGAGAAUAUCACUGUCCCAGACACCAAAGUUAAUUUCUAU
GCCUGGAAGAGGAUGGAGGUCGGGCAGCAGGCCGUAGAAGUCUGGCAGGGCCUGGCCCUGCUGUCGGAAGCUGUCC
UGCGGGGCCAGGCCCUGUUGGUCAACUCUUCCCAGCCGUGGGAGCCCCUGCAGCUGCAUGUGGAUAAAGCCGUCAG
UGGCCUUCGCAGCCUCACCACUCUGCUUCGGGCUCUGGGAGCCCAGAAGGAAGCCAUCUCCCCUCCAGAUGCGGCCU
CAGCUGCUCCACUCCGAACAAUCACUGCUGACACUUUCCGCAAACUCUUCCGAGUCUACUCCAAUUUCCUCCGGGG
AAAGCUGAAGCUGUACACAGGGGAGGCCUGCAGGACAGGGGACAGAUGA (SEQ ID NO: 3)

FIG. 3

Human alpha-galactosidase (GLA) mRNA:

AUGCAGCUGAGGAACCCAGAACUACAUCUGGGCUGCGCGCUUGCGCUUCGCUUCCUGGCCCUCGUUUCCUGGGACA
UCCCUGGGGCUAGAGCACUGGACAAUGGAUUGGCAAGGACGCCUACCAUGGGCUGGCUGCACUGGGAGCGCUUCAU
GUGCAACCUUGACUGCCAGGAAGAGCCAGAUUCCUGCAUCAGUGAGAAGCUCUUCAUGGAGAUGGCAGAGCUCAUG
GUCUCAGAAGGCUGGAAGGAUGCAGGUUAUGAGUACCUCUGCAUUGAUGACUGUUGGAUGGCUCCCCAAAGAGAU
UCAGAAGGCAGACUUCAGGCAGACCCUCAGCGCUUUCCUCAUGGGAUUCGCCAGCUAGCUAAUUAUGUUCACAGCA
AAGGACUGAAGCUAGGGAUUUAUGCAGAUGUUGGAAAUAAAACCUGCGCAGGCUUCCCUGGGAGUUUUGGAUACU
ACGACAUUGAUGCCCAGACCUUUGCUGACUGGGGAGUAGAUCUGCUAAAAUUUGAUGGUUGUUACUGUGACAGUU
UGGAAAAUUUGGCAGAUGGUUAUAAGCACAUGUCCUUGGCCCUGAAUAGGACUGGCAGAAGCAUUGUGUACUCCU
GUGAGUGGCCUCUUUAUAUGUGGCCCUUUCAAAAGCCCAAUUAUACAGAAAUCCGACAGUACUGCAAUCACUGGCG
AAAUUUUGCUGACAUUGAUGAUUCCUGGAAAAGUAUAAAGAGUAUCUUGGACUGGACAUCUUUUAACCAGGAGAG
AAUUGUUGAUGUUGCUGGACCAGGGGGUUGGAAUGACCCAGAUAUGUUAGUGAUUGGCAACUUUGGCCUCAGCUG
GAAUCAGCAAGUAACUCAGAUGGCCCUCUGGGCUAUCAUGGCUGCUCCUUUAUUCAUGUCUAAUGACCUCCGACAC
AUCAGCCCUCAAGCCAAAGCUCUCCUUCAGGAUAAGGACGUAAUUGCCAUCAAUCAGGACCCCUUGGGCAAGCAAG
GGUACCAGCUUAGACAGGGAGACAACUUUGAAGUGUGGGAACGACCUCUCUCAGGCUUAGCCUGGGCUGUAGCUAU
GAUAAACCGGCAGGAGAUUGGUGGACCUCGCUCUUAUACCAUCGCAGUUGCUUCCCUGGGUAAAGGAGUGGCCUGU
AAUCCUGCCUGCUUCAUCACACAGCUCCUCCCUGUGAAAAGGAAGCUAGGGUUCUAUGAAUGGACUUCAAGGUUAA
GAAGUCACAUAAAUCCCACAGGCACUGUUUUGCUUCAGCUAGAAAAUACAAUGCAGAUGUCAUUAAAAGACUUAC
UUUAA (SEQ ID NO: 4)

FIG. 4

Human alpha-1 antitrypsin (A1AT) mRNA:

AUGCCGUCUUCUGUCUCGUGGGGCAUCCUCCUGCUGGCAGGCCUGUGCUGCCUGGUCCCUGUCUCCCUGGCUGAGG
AUCCCCAGGGAGAUGCUGCCCAGAAGACAGAUACAUCCCACCAUGAUCAGGAUCACCCAACCUUCAACAAGAUCAC
CCCCAACCUGGCUGAGUUCGCCUUCAGCCUAUACCGCCAGCUGGCACACCAGUCCAACAGCACCAAUAUCUUCUUCU
CCCCAGUGAGCAUCGCUACAGCCUUUGCAAUGCUCUCCCUGGGGACCAAGGCUGACACUCACGAUGAAAUCCUGGA
GGGCCUGAAUUUCAACCUCACGGAGAUUCCGGAGGCUCAGAUCCAUGAAGGCUUCCAGGAACUCCUCCGUACCCUC
AACCAGCCAGACAGCCAGCUCCAGCUGACCACCGGCAAUGGCCUGUUCCUCAGCGAGGGCCUGAAGCUAGUGGAUA
AGUUUUUGGAGGAUGUUAAAAAGUUGUACCACUCAGAAGCCUUCACUGUCAACUUCGGGGACACCGAAGAGGCCA
AGAAACAGAUCAACGAUUACGUGGAGAAGGGUACUCAAGGGAAAAUUGUGGAUUUGGUCAAGGAGCUUGACAGAG
ACACAGUUUUUGCUCUGGUGAAUUACAUCUUCUUUAAAGGCAAAUGGGAGAGACCCUUUGAAGUCAAGGACACCG
AGGAAGAGGACUUCCACGUGGACCAGGUGACCACCGUGAAGGUGCCUAUGAUGAAGCGUUUAGGCAUGUUUAACA
UCCAGCACUGUAAGAAGCUGUCCAGCUGGGUGCUGCUGAUGAAAUACCUGGGCAAUGCCACCGCCAUCUUCUUCCU
GCCUGAUGAGGGGAAACUACAGCACCUGGAAAAUGAACUCACCCACGAUAUCAUCACCAAGUUCCUGGAAAAUGAA
GACAGAAGGUCUGCCAGCUUACAUUUACCCAAACUGUCCAUUACUGGAACCUAUGAUCUGAAGAGCGUCCUGGGUC
AACUGGGCAUCACUAAGGUCUUCAGCAAUGGGGCUGACCUCUCCGGGGUCACAGAGGAGGCACCCCUGAAGCUCUC
CAAGGCCGUGCAUAAGGCUGUGCUGACCAUCGACGAGAAAGGGACUGAAGCUGCUGGGGCCAUGUUUUUAGAGGCC
AUACCCAUGUCUAUCCCCCCCGAGGUCAAGUUCAACAAACCCUUUGUCUUCUUAAUGAUUGAACAAAAUACCAAGU
CUCCCCUCUUCAUGGGAAAAGUGGUGAAUCCCACCCAAAAAUAA (SEQ ID NO: 5)

FIG. 5

Human Factor IX (FIX) mRNA:

AUGCAGCGCGUGAACAUGAUCAUGGCAGAAUCACCAGGCCUCAUCACCAUCUGCCUUUUAGGAUAUCUACUCAGUG
CUGAAUGUACAGUUUUUCUUGAUCAUGAAAACGCCAACAAAAUUCUGAGGCGGAGAAGGAGGUAUAAUUCAGGUA
AAUUGGAAGAGUUUGUUCAAGGGAACCUUGAGAGAGAAUGUAUGGAAGAAAAGUGUAGUUUUGAAGAAGCACGAG
AAGUUUUUGAAAACACUGAAAGAACAACUGAAUUUUGGAAGCAGUAUGUUGAUGGAGAUCAGUGUGAGUCCAAUC
CAUGUUUAAAUGGCGGCAGUUGCAAGGAUGACAUUAAUUCCUAUGAAUGUUGGUGUCCCUUUGGAUUUGAAGGAA
AGAACUGUGAAUUAGAUGUAACAUGUAACAUUAAGAAUGGCAGAUGCGAGCAGUUUUGUAAAAAUAGUGCUGAUA
ACAAGGUGGUUUGCUCCUGUACUGAGGGAUAUCGACUUGCAGAAAACCAGAAGUCCUGUGAACCAGCAGUGCCAUU
UCCAUGUGGAAGAGUUUCUGUUUCACAAACUUCUAAGCUCACCCGUGCUGAGGCUGUUUUUCCUGAUGUGGACUAU
GUAAAUUCUACUGAAGCUGAAACCAUUUUGGAUAACAUCACUCAAAGCACCCAAUCAUUUAAUGACUUCACUCGGG
UUGUUGGUGGAGAAGAUGCCAAACCAGGUCAAUUCCCUUGGCAGGUUGUUUUGAAUGGUAAAGUUGAUGCAUUCU
GUGGAGGCUCUAUCGUUAAUGAAAAAUGGAUUGUAACUGCUGCCCACUGUGUUGAAACUGGUGUUAAAAUUACAG
UUGUCGCAGGUGAACAUAAUAUUGAGGAGACAGAACAUACAGAGCAAAAGCGAAAUGUGAUUCGAAUUAUUCCUC
ACCACAACUACAAUGCAGCUAUUAAUAAGUACAACCAUGACAUUGCCCUUCUGGAACUGGACGAACCCUUAGUGCU
AAACAGCUACGUUACACCUAUUUGCAUUGCUGACAAGGAAUACACGAACAUCUUCCUCAAAUUUGGAUCUGGCUAU
GUAAGUGGCUGGGGAAGAGUCUUCCACAAAGGGAGAUCAGCUUUAGUUCUUCAGUACCUUAGAGUUCCACUUGUU
GACCGAGCCACAUGUCUUCGAUCUACAAAGUUCACCAUCUAUAACAACAUGUUCUGUGCUGGCUUCCAUGAAGGAG
GUAGAGAUUCAUGUCAAGGAGAUAGUGGGGGACCCCAUGUUACUGAAGUGGAAGGGACCAGUUUCUUAACUGGAA
UUAUUAGCUGGGGUGAAGAGUGUGCAAUGAAAGGCAAAUAUGGAAUAUAUACCAAGGUAUCCCGGUAUGUCAACU
GGAUUAAGGAAAAAACAAAGCUCACUUAA (SEQ ID NO: 6)

FIG. 6

SEQUENCE LISTING

```
Sequence total quantity: 11
SEQ ID NO: 1           moltype = RNA  length = 140
FEATURE                Location/Qualifiers
misc_feature           1..3
                       note = This region may or may not be present
source                 1..140
                       mol_type = other RNA
                       organism = synthetic construct
SEQUENCE: 1
ggacagatcg cctggagacg ccatccacgc tgttttgacc tccatagaag acaccgggac  60
cgatccagcc tccgcggccg ggaacggtgc attggaacgc ggattccccg tgccaagagt  120
gactcaccgt ccttgacacg                                              140

SEQ ID NO: 2           moltype = RNA  length = 100
FEATURE                Location/Qualifiers
source                 1..100
                       mol_type = other RNA
                       organism = synthetic construct
SEQUENCE: 2
cgggtggcat ccctgtgacc cctccccagt gcctctcctg gccctggaag ttgccactcc  60
agtgcccacc agccttgtcc taataaaatt aagttgcatc                        100

SEQ ID NO: 3           moltype = RNA  length = 582
FEATURE                Location/Qualifiers
source                 1..582
                       mol_type = other RNA
                       organism = synthetic construct
SEQUENCE: 3
atgggggtgc acgaatgtcc tgcctggctg tggcttctcc tgtccctgct gtcgctccct  60
ctgggcctcc cagtcctggg cgccccacca cgcctcatct gtgacagccg agtcctggag  120
aggtacctct tggaggccaa ggaggccgag aatatcacga cgggctgtgc tgaacactgc  180
agcttgaatg agaatatcac tgtcccagac accaaagtta atttctatgc ctggaagagg  240
atggaggtcg ggcagcaggc cgtagaagtc tggcagggcc tggccctgct gtcggaagct  300
gtcctgcggg gccaggccct gttggtcaac tcttcccagc cgtgggagcc cctgcagctg  360
catgtggata aagccgtcag tggccttcgc agcctcacca ctctgcttcg ggctctggga  420
gcccagaagg aagccatctc ccctccagat gcggcctcag ctgctccact ccgaacaatc  480
actgctgaca ctttccgcaa actcttccga gtctactcca atttcctccg gggaaagctg  540
aagctgtaca caggggaggc ctgcaggaca ggggacagat ga                    582

SEQ ID NO: 4           moltype = RNA  length = 1290
FEATURE                Location/Qualifiers
source                 1..1290
                       mol_type = other RNA
                       organism = synthetic construct
SEQUENCE: 4
atgcagctga ggaacccaga actacatctg ggctgcgcgc ttgcgcttcg cttcctggcc  60
ctcgtttcct gggacatccc tggggctaga gcactggaca atggattggc aaggacgcct  120
accatgggct ggctgcactg ggagcgcttc atgtgcaacc ttgactgcca ggaagagcca  180
gattcctgca tcagtgagaa gctcttcatg gagatggcag agctcatggt ctcagaaggc  240
tggaaggatg caggttatga gtacctctgc attgatgact gttggatggc tccccaaaga  300
gattcagaag gcagacttca ggcagaccct cagcgctttc ctcatgggat tcgccagcta  360
gctaattatg ttcacagcaa aggactgaag ctagggattt atgcagatgt tggaaataaa  420
acctgcgcag gcttccctgg gagttttgga tactacgaca ttgatgccca gacctttgct  480
gactggggag tagatctgct aaaatttgat ggttgttact gtgacagttt ggaaaatttg  540
gcagatggtt ataagcacat gtccttggcc ctgaatagga ctggcagaag cattgtgtac  600
tcctgtgagt ggcctcttta tatgtggccc tttcaaaagc ccaattatac agaaatccga  660
cagtactgca atcactggcg aaattttgct gacattgatg attcctggaa aagtataaag  720
agtatcttgg actggacatc ttttaaccag gagagaattg ttgatgttgc tggaccaggg  780
ggttggaatg acccagatat gttagtgatt ggcaactttg gcctcagctg gaatcagcaa  840
gtaactcaga tggccctctg ggctatcatg gctgctcctt tattcatgtc taatgacctc  900
cgacacatca gccctcaagc caaagctctc cttcaggata aggacgtaat tgccatcaat  960
caggacccct tgggcaagca agggtaccag cttagacagg gagacaactt tgaagtgtgg  1020
gaacgacctc tctcaggctt agcctgggct gtagctatga taaaccggca ggagattggt  1080
ggacctcgct cttataccat cgcagttgct tccctgggta aaggagtggc ctgtaatcct  1140
```

-continued

```
gcctgcttca tcacacagct cctccctgtg aaaaggaagc tagggttcta tgaatggact  1200
tcaaggttaa gaagtcacat aaatcccaca ggcactgttt tgcttcagct agaaaataca  1260
atgcagatgt cattaaaaga cttactttaa                                   1290

SEQ ID NO: 5            moltype = RNA  length = 1257
FEATURE                 Location/Qualifiers
source                  1..1257
                        mol_type = other RNA
                        organism = synthetic construct
SEQUENCE: 5
atgccgtctt ctgtctcgtg ggcatcctc ctgctggcag gcctgtgctg cctggtccct  60
gtctccctgg ctgaggatcc ccagggagat gctgcccaga agacagatac atcccaccat  120
gatcaggatc acccaacctt caacaagatc acccccaacc tggctgagtt cgccttcagc  180
ctataccgcc agctggcaca ccagtccaac agcaccaata tcttcttctc cccagtgagc  240
atcgctacag cctttgcaat gctctccctg gggaccaagg ctgacactca cgatgaaatc  300
ctggagggcc tgaatttcaa cctcacggag attccggagg ctcagatcca tgaaggcttc  360
caggaactcc tccgtaccct caaccagcca gacagccagc tccagctgac caccggcaat  420
ggcctgttcc tcagcgaggg cctgaagcta gtggataagt tttggagga tgttaaaaag  480
ttgtaccact cagaagcctt cactgtcaac ttcggggaca ccgaagaggc caagaaacag  540
atcaacgatt acgtggagaa gggtactcaa gggaaaattg tggatttggt caaggagctt  600
gacagagaca cagtttttgc tctggtgaat tacatcttct ttaaaggcaa atgggagaga  660
ccctttgaag tcaaggacac cgaggaagag gacttccacg tggaccaggt gaccaccgtg  720
aaggtgccta tgatgaagcg tttaggcatg tttaacatcc agcactgtaa gaagctgtcc  780
agctgggtgc tgctgatgaa atacctgggc aatgccaccg ccatcttctt cctgcctgat  840
gaggggaaac tacagcacct ggaaaatgaa ctcacccacg atatcatcac caagttcctg  900
gaaaatgaag acagaaggtc tgccagctta catttaccca aactgtccat tactggaacc  960
tatgatctga agagcgtcct gggtcaactg ggcatcacta aggtcttcag caatggggct  1020
gacctctccg gggtcacaga ggaggcaccc ctgaagctct ccaaggccgt gcataaggct  1080
gtgctgacca tcgacgagaa agggactgaa gctgctgggg ccatgttttt agaggccata  1140
cccatgtcta tcccccccga ggtcaagttc aacaaaccct ttgtcttctt aatgattgaa  1200
caaaatacca agtctcccct cttcatggga aaagtggtga atcccaccca aaaataa     1257

SEQ ID NO: 6            moltype = RNA  length = 1386
FEATURE                 Location/Qualifiers
source                  1..1386
                        mol_type = other RNA
                        organism = synthetic construct
SEQUENCE: 6
atgcagcgcg tgaacatgat catggcagaa tcaccaggcc tcatcaccat ctgcctttta  60
ggatatctac tcagtgctga atgtacagtt tttcttgatc atgaaaacgc caacaaaatt  120
ctgaggcgga gaaggaggta taattcaggt aaattggaag agtttgttca agggaacctt  180
gagagagaat gtatggaaga aaagtgtagt tttgaagaag cacgagaagt ttttgaaaac  240
actgaaagaa caactgaatt ttggaagcag tatgttgatg gagatcagtg tgagtccaat  300
ccatgtttaa atggcggcag ttgcaaggat gacattaatt cctatgaatg ttggtgtccc  360
tttggatttg aaggaaagaa ctgtgaatta gatgtaacat gtaacattaa gaatggcaga  420
tgcgagcagt tttgtaaaaa tagtgctgat aacaaggtgg tttgctcctg tactgaggga  480
tatcgacttg cagaaaacca gaagtcctgt gaaccagcag tgccatttcc atgtggaaga  540
gtttctgttt cacaaacttc taagctcacc cgtgctgagg ctgtttttcc tgatgtggac  600
tatgtaaatt ctactgaagc tgaaaccatt ttggataaca tcactcaaag cacccaatca  660
tttaatgact tcactcgggt tgttggtgga gaagatgcca aaccaggtca attcccttgg  720
caggttgttt tgaatggtaa agttgatgca ttctgtggag gctctatcgt taatgaaaaa  780
tggattgtaa ctgctgccca ctgtgttgaa actggtgtta aaattacagt tgtcgcaggt  840
gaacataata ttgaggagac agaacataca gagcaaaagc gaaatgtgat tcgaattatt  900
cctcaccaca actacaatgc agctattaat aagtacaacc atgacattgc ccttctggaa  960
ctggacgaac ccttagtgct aaacagctac gttacaccta tttgcattgc tgacaaggaa  1020
tacacgaaca tcttcctcaa atttggatct ggctatgtaa gtggctgggg aagagtcttc  1080
cacaaaggga gatcagcttt agttcttcag taccttagag ttccacttgt tgaccgagcc  1140
acatgtcttc gatctacaaa gttcaccatc tataacaaca tgttctgtgc tggcttccat  1200
gaaggaggta gagattcatg tcaaggagat agtgggggac cccatgttac tgaagtggaa  1260
gggaccagtt tcttaactgg aattattagc tggggtgaag agtgtgcaat gaaaggcaaa  1320
tatggaatat ataccaaggt atcccggtat gtcaactgga ttaaggaaaa aacaaagctc  1380
acttaa                                                             1386

SEQ ID NO: 7            moltype = RNA  length = 90
FEATURE                 Location/Qualifiers
misc_feature            1..90
                        note = Synthetic oligonucleotide
source                  1..90
                        mol_type = other RNA
                        organism = synthetic construct
SEQUENCE: 7
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa                                   90
```

-continued

```
SEQ ID NO: 8           moltype = RNA  length = 200
FEATURE                Location/Qualifiers
misc_feature           1..200
                       note = Synthetic oligonucleotide
source                 1..200
                       mol_type = other RNA
                       organism = synthetic construct
SEQUENCE: 8
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa                                              200

SEQ ID NO: 9           moltype = RNA  length = 300
FEATURE                Location/Qualifiers
misc_feature           1..300
                       note = Synthetic oligonucleotide
source                 1..300
                       mol_type = other RNA
                       organism = synthetic construct
SEQUENCE: 9
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300

SEQ ID NO: 10          moltype = RNA  length = 400
FEATURE                Location/Qualifiers
misc_feature           1..400
                       note = Synthetic oligonucleotide
source                 1..400
                       mol_type = other RNA
                       organism = synthetic construct
SEQUENCE: 10
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa                        400

SEQ ID NO: 11          moltype = RNA  length = 500
FEATURE                Location/Qualifiers
misc_feature           1..500
                       note = Synthetic oligonucleotide
source                 1..500
                       mol_type = other RNA
                       organism = synthetic construct
SEQUENCE: 11
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaaaa aaaaaaaaaa  480
aaaaaaaaaa aaaaaaaaaa                                              500
```

LIPID NANOPARTICLE COMPOSITIONS AND METHODS FOR MRNA DELIVERY

CROSS-REFERENCE TO RELATED APPLICATIONS

The present application is a divisional application of U.S. application Ser. No. 17/832,202 filed Jun. 3, 2022, which is a divisional application of U.S. application Ser. No. 17/558,310 filed Dec. 21, 2021, which is a divisional application of U.S. application Ser. No. 17/509,674 filed Oct. 25, 2021, issued as U.S. Pat. No. 11,291,734, which is a divisional application of U.S. application Ser. No. 17/341,016 filed Jun. 7, 2021, issued as U.S. Pat. No. 11,185,595, which is a divisional application of U.S. application Ser. No. 17/099,462 filed Nov. 16, 2020, issued as U.S. Pat. No. 11,052,159, which is a divisional application of U.S. application Ser. No. 16/931,231 filed Jul. 16, 2020, issued as U.S. Pat. No. 10,888,626, which is a divisional application of U.S. application Ser. No. 16/681,565 filed Nov. 12, 2019, now abandoned, which is a divisional application of U.S. application Ser. No. 16/502,672 filed Jul. 3, 2019, issued as U.S. Pat. No. 10,507,249, which is a divisional application of U.S. application Ser. No. 16/286,400 filed on Feb. 26, 2019, issued as U.S. Pat. No. 10,350,303 on Jul. 16, 2019, which is a divisional application of U.S. application Ser. No. 16/233,031 filed on Dec. 26, 2018, now issued as U.S. Pat. No. 10,413,618, which is a divisional application of U.S. application Ser. No. 15/482,117 filed on Apr. 7, 2017, now issued as U.S. Pat. No. 10,238,754, which is a divisional application of U.S. application Ser. No. 14/124,608 filed on Mar. 5, 2014, now abandoned, which is a U.S. National Entry claiming priority to International Application PCT/US2012/041724 filed on Jun. 8, 2012, which claims priority to U.S. Provisional Application Ser. No. 61/494,881 filed Jun. 8, 2011, the disclosures of which are hereby incorporated by reference.

INCORPORATION-BY-REFERENCE OF SEQUENCE LISTING

This instant application contains a Sequence Listing which has been submitted electronically in xml format and is hereby incorporated by reference in its entirety. Said xml copy, created on Mar. 29, 2023, is named MRT-1055.xml and is 19 KB in size. No new matter is hereby added.

Novel approaches and therapies are still needed for the treatment of protein and enzyme deficiencies. For example, lysosomal storage diseases are a group of approximately 50 rare inherited metabolic disorders that result from defects in lysosomal function, usually due to a deficiency of an enzyme required for metabolism. Fabry disease is a lysosomal storage disease that results from a deficiency of the enzyme alpha galactosidase (GLA), which causes a glycolipid known as globotriaosylceramide to accumulate in blood vessels and other tissues, leading to various painful manifestations. For certain diseases, like Fabry disease, there is a need for replacement of a protein or enzyme that is normally secreted by cells into the blood stream. Therapies, such as gene therapy, that increase the level or production of an affected protein or enzyme could provide a treatment or even a cure for such disorders. However, there have been several limitations to using conventional gene therapy for this purpose.

Conventional gene therapy involves the use of DNA for insertion of desired genetic information into host cells. The DNA introduced into the cell is usually integrated to a certain extent into the genome of one or more transfected cells, allowing for long-lasting action of the introduced genetic material in the host. While there may be substantial benefits to such sustained action, integration of exogenous DNA into a host genome may also have many deleterious effects. For example, it is possible that the introduced DNA will be inserted into an intact gene, resulting in a mutation which impedes or even totally eliminates the function of the endogenous gene. Thus, gene therapy with DNA may result in the impairment of a vital genetic function in the treated host, such as e.g., elimination or deleteriously reduced production of an essential enzyme or interruption of a gene critical for the regulation of cell growth, resulting in unregulated or cancerous cell proliferation. In addition, with conventional DNA based gene therapy it is necessary for effective expression of the desired gene product to include a strong promoter sequence, which again may lead to undesirable changes in the regulation of normal gene expression in the cell. It is also possible that the DNA based genetic material will result in the induction of undesired anti-DNA antibodies, which in turn, may trigger a possibly fatal immune response. Gene therapy approaches using viral vectors can also result in an adverse immune response. In some circumstances, the viral vector may even integrate into the host genome. In addition, production of clinical grade viral vectors is also expensive and time consuming. Targeting delivery of the introduced genetic material using viral vectors can also be difficult to control. Thus, while DNA based gene therapy has been evaluated for delivery of secreted proteins using viral vectors (U.S. Pat. No. 6,066,626; US2004/0110709), these approaches may be limited for these various reasons.

Another obstacle apparent in these prior approaches at delivery of nucleic acids encoding secreted proteins, is in the levels of protein that are ultimately produced. It is difficult to achieve significant levels of the desired protein in the blood, and the amounts are not sustained over time. For example, the amount of protein produced by nucleic acid delivery does not reach normal physiological levels. See e.g., US2004/0110709.

In contrast to DNA, the use of RNA as a gene therapy agent is substantially safer because (1) RNA does not involve the risk of being stably integrated into the genome of the transfected cell, thus eliminating the concern that the introduced genetic material will disrupt the normal functioning of an essential gene, or cause a mutation that results in deleterious or oncogenic effects; (2) extraneous promoter sequences are not required for effective translation of the encoded protein, again avoiding possible deleterious side effects; (3) in contrast to plasmid DNA (pDNA), messenger RNA (mRNA) is devoid of immunogenic CpG motifs so that anti-RNA antibodies are not generated; and (4) any deleterious effects that do result from mRNA based on gene therapy would be of limited duration due to the relatively short half-life of RNA. In addition, it is not necessary for mRNA to enter the nucleus to perform its function, while DNA must overcome this major barrier.

One reason that mRNA based gene therapy has not been used more in the past is that mRNA is far less stable than DNA, especially when it reaches the cytoplasm of a cell and is exposed to degrading enzymes. The presence of a hydroxyl group on the second carbon of the sugar moiety in mRNA causes steric hinderance that prevents the mRNA from forming the more stable double helix structure of DNA and thus makes the mRNA more prone to hydrolytic degradation. As a result, until recently, it was widely believed that mRNA was too labile to withstand transfection protocols. Advances in RNA stabilizing modifications have sparked more interest in the use of mRNA in place of plasmid DNA in gene therapy. Certain delivery vehicles, such as cationic lipid or polymer delivery vehicles may also help protect the transfected mRNA from endogenous RNases. Yet, in spite of increased stability of modified mRNA, delivery of mRNA to cells in vivo in a manner allowing for therapuetic levels of protein production is still a challenge, particularly for mRNA encoding full length proteins. While delivery of mRNA encoding secreted proteins has been contemplated (US2009/0286852), the levels of a full length secreted protein that would actually be produced via in vivo mRNA delivery are not known and there is not a reason to expect the levels would exceed those observed with DNA based gene therapy.

To date, significant progress using mRNA gene therapy has only been made in applications for which low levels of translation has not been a limiting factor, such as immunization with mRNA encoding antigens. Clinical trials involving vaccination against tumor antigens by intradermal injection of naked or protamine-complexed mRNA have demonstrated feasibility, lack of toxicity, and promising results. X. Su et al., *Mol. Pharmaceutics* 8:774-787 (2011). Unfortunately, low levels of translation has greatly restricted the exploitation of mRNA based gene therapy in other applications which require higher levels of sustained expression of the mRNA encoded protein to exert a biological or therapeutic effect.

The invention provides methods for delivery of mRNA gene therapeutic agents that lead to the production of therapeutically effective levels of secreted proteins via a "depot effect." In embodiments of the invention, mRNA encoding a secreted protein is loaded in lipid nanoparticles and delivered to target cells in vivo. Target cells then act as a depot source for production of soluble, secreted protein into the circulatory system at therapeutic levels. In some embodiments, the levels of secreted protein produced are above normal physiological levels.

The invention provides compositions and methods for intracellular delivery of mRNA in a liposomal transfer vehicle to one or more target cells for production of therapeutic levels of secreted functional protein.

The compositions and methods of the invention are useful in the management and treatment of a large number of diseases, in particular diseases which result from protein and/or enzyme deficiencies, wherein the protein or enzyme is normally secreted. Individuals suffering from such diseases may have underlying genetic defects that lead to the compromised expression of a protein or enzyme, including, for example, the non-synthesis of the secreted protein, the reduced synthesis of the secreted protein, or synthesis of a secreted protein lacking or having diminished biological activity. In particular, the methods and compositions of the invention are useful for the treatment of lysosomal storage disorders and/or the urea cycle metabolic disorders that occur as a result of one or more defects in the biosynthesis of secreted enzymes involved in the urea cycle.

The compositions of the invention comprise an mRNA, a transfer vehicle and, optionally, an agent to facilitate contact with, and subsequent transfection of a target cell. The mRNA can encode a clinically useful secreted protein. For example, the mRNA may encode a functional secreted urea cycle enzyme or a secreted enzyme implicated in lysosomal storage disorders. The mRNA can encode, for example, erythropoietin (e.g., human EPO) or α-galactosidase (e.g., human α-galactosidase (human GLA).

In some embodiments the mRNA can comprise one or more modifications that confer stability to the mRNA (e.g., compared to a wild-type or native version of the mRNA) and may also comprise one or more modifications relative to the wild-type which correct a defect implicated in the associated aberrant expression of the protein. For example, the nucleic acids of the present invention may comprise modifications to one or both of the 5' and 3' untranslated regions. Such modifications may include, but are not limited to, the inclusion of a partial sequence of a cytomegalovirus (CMV) immediate-early 1 (IE1) gene, a poly A tail, a Cap1 structure or a sequence encoding human growth hormone (hGH)). In some embodiments, the mRNA is modified to decrease mRNA immunogenecity.

Methods of treating a subject comprising administering a composition of the invention, are also contemplated. For example, methods of treating or preventing conditions in which production of a particular secreted protein and/or utilization of a particular secreted protein is inadequate or compromised are provided. In one embodiment, the methods provided herein can be used to treat a subject having a deficiency in one or more urea cycle enzymes or in one or more enzymes deficient in a lysosomal storage disorder.

In a preferred embodiment, the mRNA in the compositions of the invention is formulated in a liposomal transfer vehicle to facilitate delivery to the target cell. Contemplated transfer vehicles may comprise one or more cationic lipids, non-cationic lipids, and/or PEG-modified lipids. For example, the transfer vehicle may comprise at least one of the following cationic lipids: C12-200, DLin-KC2-DMA, DODAP, HGT4003, ICE, HGT5000, or HGT5001. In embodiments, the transfer vehicle comprises cholesterol (chol) and/or a PEG-modified lipid. In some embodiments, the transfer vehicles comprises DMG-PEG2K. In certain embodiments, the tranfer vehicle comprises one of the following lipid formulations: C12-200, DOPE, chol, DMG-PEG2K; DODAP, DOPE, cholesterol, DMG-PEG2K; HGT5000, DOPE, chol, DMG-PEG2K, HGT5001, DOPE, chol, DMG-PEG2K.

The invention also provides compositions and methods useful for facilitating the transfection and delivery of one or more mRNA molecules to target cells capable of exhibiting the "depot effect." For example, the compositions and methods of the present invention contemplate the use of targeting ligands capable of enhancing the affinity of the composition to one or more target cells. In one embodiment, the targeting ligand is apolipoprotein-B or apolipoprotein-E and corresponding target cells express low-density lipoprotein receptors, thereby facilitating recognition of the targeting ligand. The methods and compositions of the present invention may be used to preferentially target a vast number of target cells. For example, contemplated target cells include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

In embodiments, the secreted protein is produced by the target cell for sustained amounts of time. For example, the secreted protein may be produced for more than one hour, more than four, more than six, more than 12, more than 24, more than 48 hours, or more than 72 hours after administration. In some embodiments the polypeptide is expressed at a peak level about six hours after administration. In some embodiments the expression of the polypeptide is sustained at least at a therapeutic level. In some embodiments the polypeptide is expressed at at least a therapeutic level for more than one, more than four, more than six, more than 12, more than 24, more than 48 hours, or more than 72 hours after administration. In some embodiments the polypeptide is detectable at the level in patient serum or tissue (e.g., liver, or lung). In some embodiments, the level of detectable polypeptide is from continuous expression from the mRNA composition over periods of time of more than one, more than four, more than six, more than 12, more than 24, more than 48 hours, or more than 72 hours after administration.

In certain embodiments, the secreted protein is produced at levels above normal physiological levels. The level of secreted protein may be increased as compared to a control.

In some embodiments the control is the baseline physiological level of the polypeptide in a normal individual or in a population of normal individuals. In other embodiments the control is the baseline physiological level of the polypeptide in an individual having a deficiency in the relevant protein or polypeptide or in a population of individuals having a deficiency in the relevant protein or polypeptide. In some embodiments the control can be the normal level of the relevant protein or polypeptide in the individual to whom the composition is administered. In other embodiments the control is the expression level of the polypeptide upon other therapeutic intervention, e.g., upon direct injection of the corresponding polypeptide, at one or more comparable time points.

In certain embodiments the polypeptide is expressed by the target cell at a level which is at least 1.5-fold, at least 2-fold, at least 5-fold, at least 10-fold, at least 20-fold, 30-fold, at least 100-fold, at least 500-fold, at least 5000-fold, at least 50,000-fold or at least 100,000-fold greater than a control. In some embodiments, the fold increase of expression greater than control is sustained for more than one, more than four, more than six, more than 12, more than 24, or more than 48 hours, or more than 72 hours after administration. For example, in one embodiment, the levels of secreted protein are detected in the serum at least 1.5-fold, at least 2-fold, at least 5-fold, at least 10-fold, at least 20-fold, 30-fold, at least 100-fold, at least 500-fold, at least 5000-fold, at least 50,000-fold or at least 100,000-fold greater than a control for at least 48 hours or 2 days. In certain embodiments, the levels of secreted protein are detectable at 3 days, 4 days, 5 days, or 1 week or more after administration. Increased levels of secreted protein may be observed in the serum and/or in a tissue (e.g. liver, lung).

In some embodiments, the method yields a sustained circulation half-life of the desired secreted protein. For example, the secreted protein may be detected for hours or days longer than the half-life observed via subcutaneous injection of the secreted protein. In embodiments, the half-life of the secreted protein is sustained for more than 1 day, 2 days, 3 days, 4 days, 5 days, or 1 week or more.

In some embodiments administration comprises a single or repeated doses. In certain embodiments, the dose is administered intravenously, or by pulmonary delivery.

The polypeptide can be, for example, one or more of erythropoietin, α-galactosidase, LDL receptor, Factor VIII, Factor IX, α-L-iduronidase (for MPS I), iduronate sulfatase (for MPS II), heparin-N-sulfatase (for MPS IIIA), α-N-acetylglucosaminidase (for MPS IIIB), galactose 6-sultatase (for MPS IVA), lysosomal acid lipase, arylsulfatase-A.

Certain embodiments relate to compositions and methods that provide to a cell or subject mRNA, at least a part of which encodes a functional protein, in an amount that is substantially less that the amount of corresponding functional protein generated from that mRNA. Put another way, in certain embodiments the mRNA delivered to the cell can produce an amount of protein that is substantially greater than the amount of mRNA delivered to the cell. For example, in a given amount of time, for example 1, 2, 3, 4, 5, 6, 7, 8, 9, 10, 12, 15, 20, or 24 hours from administration of the mRNA to a cell or subject, the amount of corresponding protein generated by that mRNA can be at least 1.5, 2, 3, 5, 10, 15, 20, 25, 50, 100, 150, 200, 250, 300, 400, 500, or more times greater that the amount of mRNA actually administered to the cell or subject. This can be measured on a mass-by-mass basis, on a mole-by-mole basis, and/or on a molecule-by-molecule basis. The protein can be measured in various ways. For example, for a cell, the measured protein can be measured as intracellular protein, extracellular protein, or a combination of the two. For a subject, the measured protein can be protein measured in serum; in a specific tissue or tissues such as the liver, kidney, heart, or brain; in a specific cell type such as one of the various cell types of the liver or brain; or in any combination of serum, tissue, and/or cell type. Moreover, a baseline amount of endogenous protein can be measured in the cell or subject prior to administration of the mRNA and then subtracted from the protein measured after administration of the mRNA to yield the amount of corresponding protein generated from the mRNA. In this way, the mRNA can provide a reservoir or depot source of a large amount of therapeutic material to the cell or subject, for example, as compared to amount of mRNA delivered to the cell or subject. The depot source can act as a continuous source for polypeptide expression from the mRNA over sustained periods of time.

The above discussed and many other features and attendant advantages of the present invention will become better understood by reference to the following detailed description of the invention when taken in conjunction with the accompanying examples. The various embodiments described herein are complimentary and can be combined or used together in a manner understood by the skilled person in view of the teachings contained herein.

BRIEF DESCRIPTION OF THE DRAWINGS

FIG. 1 shows the nucleotide sequence of a 5' CMV sequence (SEQ ID NO: 1), wherein X, if present is GGA.

FIG. 2 shows the nucleotide sequence of a 3' hGH sequence (SEQ ID NO:2).

FIG. 3 shows the nucleotide sequence of human erythropoietic (EPO) mRNA (SEQ ID NO:3). This sequence can be flanked on the 5' end with SEQ ID NO:1 and on the 3' end with SEQ ID NO:2.

FIG. 4 shows the nucleotide sequence of human alpha-galactosidase (GLA) mRNA (SEQ ID NO:4). This sequence can be flanked on the 5' end with SEQ ID NO:1 and on the 3' end with SEQ ID NO:2.

FIG. 5 shows the nucleotide sequence of human alpha-1 antitrypsin (A1AT) mRNA (SEQ ID NO:5). This sequence can be flanked on the 5' end with SEQ ID NO:1 and on the 3' end with SEQ ID NO:2.

FIG. 6 shows the nucleotide sequence of human factor IX (FIX) mRNA (SEQ ID NO:6). This sequence can be flanked on the 5' end with SEQ ID NO:1 and on the 3' end with SEQ ID NO:2.

DESCRIPTION OF EXEMPLARY EMBODIMENTS

Figure 7:
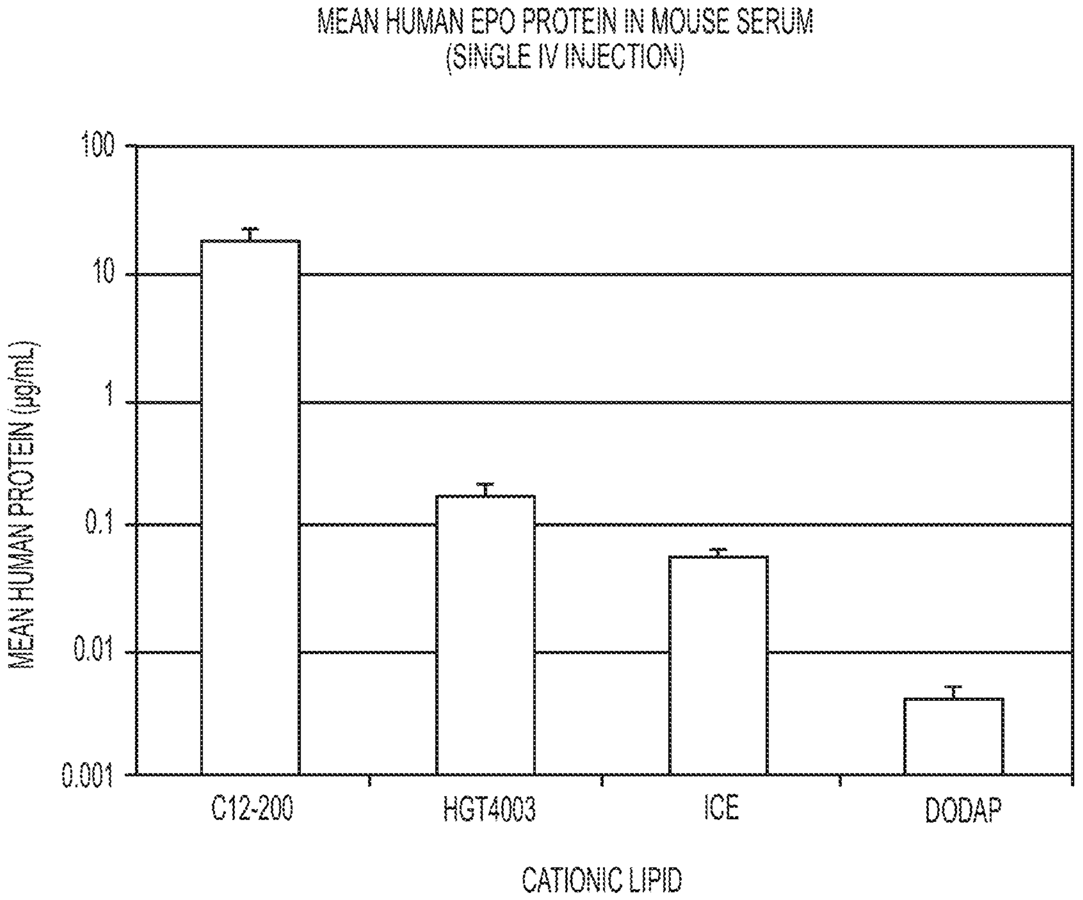
FIG. 7 shows quantification of secreted hEPO protein levels as measured via ELISA. The protein detected is a result of its production from hEPO mRNA delivered intravenously via a single dose of various lipid nanoparticle formulations. The formulations C12-200 (30 ug), HGT4003 (150 ug), ICE (100 ug), DODAP (200 ug) are represented as the cationic/ionizable lipid component of each test article (Formulations 1-4). Values are based on blood sample four hours post-administration.

The invention provides compositions and methods for intracellular delivery of mRNA in a liposomal transfer vehicle to one or more target cells for production of therapeutic levels of secreted functional protein.

The term "functional," as used herein to qualify a protein or enzyme, means that the protein or enzyme has biological activity, or alternatively is able to perform the same, or a similar function as the native or normally-functioning protein or enzyme. The mRNA compositions of the invention are useful for the treatment of a various metabolic or genetic disorders, and in particular those genetic or metabolic disorders which involve the non-expression, misexpression or deficiency of a protein or enzyme. The term "therapeutic levels" refers to levels of protein detected in the blood or tissues that are above control levels, wherein the control may be normal physiological levels, or the levels in the subject prior to administration of the mRNA composition. The term "secreted" refers to protein that is detected outside the target cell, in extracellular space. The protein may be detected in the blood or in tissues. In the context of the present invention the term "produced" is used in its broadest sense to refer the translation of at least one mRNA into a protein or enzyme. As provided herein, the compositions include a transfer vehicle. As used herein, the term "transfer vehicle" includes any of the standard pharmaceutical carriers, diluents, excipients and the like which are generally intended for use in connection with the administration of biologically active agents, including nucleic acids. The compositions and in particular the transfer vehicles described herein are capable of delivering mRNA to the target cell. In embodiments, the transfer vehicle is a lipid nanoparticle.

mRNA

The mRNA in the compositions of the invention may encode, for example, a secreted hormone, enzyme, receptor, polypeptide, peptide or other protein of interest that is normally secreted. In one embodiment of the invention, the mRNA may optionally have chemical or biological modifications which, for example, improve the stability and/or half-life of such mRNA or which improve or otherwise facilitate protein production.

The methods of the invention provide for optional co-delivery of one or more unique mRNA to target cells, for example, by combining two unique mRNAs into a single transfer vehicle. In one embodiment of the present invention, a therapeutic first mRNA, and a therapeutic second mRNA, may be formulated in a single transfer vehicle and administered. The present invention also contemplates co-delivery and/or co-administration of a therapeutic first mRNA and a second nucleic acid to facilitate and/or enhance the function or delivery of the therapeutic first mRNA. For example, such a second nucleic acid (e.g., exogenous or synthetic mRNA) may encode a membrane transporter protein that upon expression (e.g., translation of the exogenous or synthetic mRNA) facilitates the delivery or enhances the biological activity of the first mRNA. Alternatively, the therapeutic first mRNA may be administered with a second nucleic acid that functions as a "chaperone" for example, to direct the folding of either the therapeutic first mRNA.

The methods of the invention also provide for the delivery of one or more therapeutic nucleic acids to treat a single disorder or deficiency, wherein each such therapeutic nucleic acid functions by a different mechanism of action. For example, the compositions of the present invention may comprise a therapeutic first mRNA which, for example, is administered to correct an endogenous protein or enzyme deficiency, and which is accompanied by a second nucleic acid, which is administered to deactivate or "knock-down" a malfunctioning endogenous nucleic acid and its protein or enzyme product. Such "second" nucleic acids may encode, for example mRNA or siRNA.

Upon transfection, a natural mRNA in the compositions of the invention may decay with a half-life of between 30 minutes and several days. The mRNA in the compositions of the invention preferably retain at least some ability to be translated, thereby producing a functional secreted protein or enzyme. Accordingly, the invention provides compositions comprising and methods of administering a stabilized mRNA. In some embodiments of the invention, the activity of the mRNA is prolonged over an extended period of time. For example, the activity of the mRNA may be prolonged such that the compositions of the present invention are administered to a subject on a semi-weekly or bi-weekly basis, or more preferably on a monthly, bi-monthly, quarterly or an annual basis. The extended or prolonged activity of the mRNA of the present invention, is directly related to the quantity of secreted functional protein or enzyme produced from such mRNA. Similarly, the activity of the compositions of the present invention may be further extended or prolonged by modifications made to improve or enhance translation of the mRNA. Furthermore, the quantity of functional protein or enzyme produced by the target cell is a function of the quantity of mRNA delivered to the target cells and the stability of such mRNA. To the extent that the stability of the mRNA of the present invention may be improved or enhanced, the half-life, the activity of the produced secreted protein or enzyme and the dosing frequency of the composition may be further extended.

Accordingly, in some embodiments, the mRNA in the compositions of the invention comprise at least one modification which confers increased or enhanced stability to the nucleic acid, including, for example, improved resistance to nuclease digestion in vivo. As used herein, the terms "modification" and "modified" as such terms relate to the nucleic acids provided herein, include at least one alteration which preferably enhances stability and renders the mRNA more stable (e.g., resistant to nuclease digestion) than the wild-type or naturally occurring version of the mRNA. As used herein, the terms "stable" and "stability" as such terms relate to the nucleic acids of the present invention, and particularly with respect to the mRNA, refer to increased or enhanced resistance to degradation by, for example nucleases (i.e., endonucleases or exonucleases) which are normally capable of degrading such mRNA. Increased stability can include, for example, less sensitivity to hydrolysis or other destruction by endogenous enzymes (e.g., endonucleases or exonucleases) or conditions within the target cell or tissue, thereby increasing or enhancing the residence of such mRNA in the target cell, tissue, subject and/or cytoplasm. The stabilized mRNA molecules provided herein demonstrate longer half-lives relative to their naturally occurring, unmodified counterparts (e.g. the wild-type version of the mRNA). Also contemplated by the terms "modification" and "modified" as such terms related to the mRNA of the present invention are alterations which improve or enhance translation of mRNA nucleic acids, including for example, the inclusion of sequences which function in the initiation of protein translation (e.g., the Kozac consensus sequence). (Kozak, M., Nucleic Acids Res 15 (20): 8125-48 (1987)).

In some embodiments, the mRNA of the invention have undergone a chemical or biological modification to render them more stable. Exemplary modifications to an mRNA include the depletion of a base (e.g., by deletion or by the substitution of one nucleotide for another) or modification of a base, for example, the chemical modification of a base. The phrase "chemical modifications" as used herein, includes modifications which introduce chemistries which differ from those seen in naturally occurring mRNA, for example, covalent modifications such as the introduction of modified nucleotides, (e.g., nucleotide analogs, or the inclusion of pendant groups which are not naturally found in such mRNA molecules).

In addition, suitable modifications include alterations in one or more nucleotides of a codon such that the codon encodes the same amino acid but is more stable than the codon found in the wild-type version of the mRNA. For example, an inverse relationship between the stability of RNA and a higher number cytidines (C's) and/or uridines (U's) residues has been demonstrated, and RNA devoid of C and U residues have been found to be stable to most RNases (Heidenreich, et al. J Biol Chem 269, 2131-8 (1994)). In some embodiments, the number of C and/or U residues in an mRNA sequence is reduced. In a another embodiment, the number of C and/or U residues is reduced by substitution of one codon encoding a particular amino acid for another codon encoding the same or a related amino acid. Contemplated modifications to the mRNA nucleic acids of the present invention also include the incorporation of pseudouridines. The incorporation of pseudouridines into the mRNA nucleic acids of the present invention may enhance stability and translational capacity, as well as diminishing immunogenicity in vivo. See, e.g., Karikó, K., et al., Molecular Therapy 16 (11): 1833-1840 (2008). Substitutions and modifications to the mRNA of the present invention may be performed by methods readily known to one or ordinary skill in the art.

The constraints on reducing the number of C and U residues in a sequence will likely be greater within the coding region of an mRNA, compared to an untranslated region, (i.e., it will likely not be possible to eliminate all of the C and U residues present in the message while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible). For example, the codons for Gly can be altered to GGA or GGG instead of GGU or GGC.

The term modification also includes, for example, the incorporation of non-nucleotide linkages or modified nucleotides into the mRNA sequences of the present invention (e.g., modifications to one or both the 3' and 5' ends of an mRNA molecule encoding a functional secreted protein or enzyme). Such modifications include the addition of bases to an mRNA sequence (e.g., the inclusion of a poly A tail or a longer poly A tail), the alteration of the 3' UTR or the 5' UTR, complexing the mRNA with an agent (e.g., a protein or a complementary nucleic acid molecule), and inclusion of elements which change the structure of an mRNA molecule (e.g., which form secondary structures).

The poly A tail is thought to stabilize natural messengers. Therefore, in one embodiment a long poly A tail can be added to an mRNA molecule thus rendering the mRNA more stable. Poly A tails can be added using a variety of art-recognized techniques. For example, long poly A tails can be added to synthetic or in vitro transcribed mRNA using poly A polymerase (Yokoe, et al. Nature Biotechnology. 1996; 14: 1252-1256). A transcription vector can also encode long poly A tails. In addition, poly A tails can be added by transcription directly from PCR products. In one embodiment, the length of the poly A tail is at least about 90, 200, 300, 400 at least 500 nucleotides. In one embodiment, the length of the poly A tail is adjusted to control the stability of a modified mRNA molecule of the invention and, thus, the transcription of protein. For example, since the length of the poly A tail can influence the half-life of an mRNA molecule, the length of the poly A tail can be adjusted to modify the level of resistance of the mRNA to nucleases and thereby control the time course of protein expression in a cell. In one embodiment, the stabilized mRNA molecules are sufficiently resistant to in vivo degradation (e.g., by nucleases), such that they may be delivered to the target cell without a transfer vehicle.

In one embodiment, an mRNA can be modified by the incorporation 3' and/or 5' untranslated (UTR) sequences which are not naturally found in the wild-type mRNA. In one embodiment, 3' and/or 5' flanking sequence which naturally flanks an mRNA and encodes a second, unrelated protein can be incorporated into the nucleotide sequence of an mRNA molecule encoding a therapeutic or functional protein in order to modify it. For example, 3' or 5' sequences from mRNA molecules which are stable (e.g., globin, actin, GAPDH, tubulin, histone, or citric acid cycle enzymes) can be incorporated into the 3' and/or 5' region of a sense mRNA nucleic acid molecule to increase the stability of the sense mRNA molecule. See, e.g., US2003/0083272.

In some embodiments, the mRNA in the compositions of the invention include modification of the 5' end of the mRNA to include a partial sequence of a CMV immediate-early 1 (IE1) gene, or a fragment thereof (e.g., SEQ ID NO:1) to improve the nuclease resistance and/or improve the half-life of the mRNA. In addition to increasing the stability of the mRNA nucleic acid sequence, it has been surprisingly discovered the inclusion of a partial sequence of a CMV immediate-early 1 (IE1) gene enhances the translation of the mRNA and the expression of the functional protein or enzyme. Also contemplated is the inclusion of a human growth hormone (hGH) gene sequence, or a fragment thereof (e.g., SEQ ID NO:2) to the 3' ends of the nucleic acid (e.g., mRNA) to further stabilize the mRNA. Generally, preferred modifications improve the stability and/or pharmacokinetic properties (e.g., half-life) of the mRNA relative to their unmodified counterparts, and include, for example modifications made to improve such mRNA's resistance to in vivo nuclease digestion.

Further contemplated are variants of the nucleic acid sequence of SEQ ID NO:1 and/or SEQ ID NO:2, wherein the variants maintain the functional properties of the nucleic acids including stabilization of the mRNA and/or pharmacokinetic properties (e.g., half-life). Variants may have greater than 90%, greater than 95%, greater than 98%, or greater than 99% sequence identity to SEQ ID NO:1 or SEQ ID NO:2.

In some embodiments, the composition can comprise a stabilizing reagent. The compositions can include one or more formulation reagents that bind directly or indirectly to, and stabilize the mRNA, thereby enhancing residence time in the target cell. Such reagents preferably lead to an improved half-life of the mRNA in the target cells. For example, the stability of an mRNA and efficiency of translation may be increased by the incorporation of "stabilizing reagents" that form complexes with the mRNA that naturally occur within a cell (see e.g., U.S. Pat. No. 5,677,124). Incorporation of a stabilizing reagent can be accomplished for example, by combining the poly A and a protein with the mRNA to be stabilized in vitro before loading or encapsulating the mRNA within a transfer vehicle. Exemplary stabilizing reagents include one or more proteins, peptides, aptamers, translational accessory protein, mRNA binding proteins, and/or translation initiation factors.

Stabilization of the compositions may also be improved by the use of opsonization-inhibiting moieties, which are typically large hydrophilic polymers that are chemically or physically bound to the transfer vehicle (e.g., by the intercalation of a lipid-soluble anchor into the membrane itself, or by binding directly to active groups of membrane lipids). These opsonization-inhibiting hydrophilic polymers form a protective surface layer which significantly decreases the uptake of the liposomes by the macrophage-monocyte system and reticulo-endothelial system (e.g., as described in U.S. Pat. No. 4,920,016, the entire disclosure of which is herein incorporated by reference). Transfer vehicles modified with opsonization-inhibition moieties thus remain in the circulation much longer than their unmodified counterparts.

When RNA is hybridized to a complementary nucleic acid molecule (e.g., DNA or RNA) it may be protected from nucleases. (Krieg, et al. Melton. Methods in Enzymology. 1987; 155, 397-415). The stability of hybridized mRNA is likely due to the inherent single strand specificity of most RNases. In some embodiments, the stabilizing reagent selected to complex a mRNA is a eukaryotic protein, (e.g., a mammalian protein). In yet another embodiment, the mRNA can be modified by hybridization to a second nucleic acid molecule. If an entire mRNA molecule were hybridized to a complementary nucleic acid molecule translation initiation may be reduced. In some embodiments the 5' untranslated region and the AUG start region of the mRNA molecule may optionally be left unhybridized. Following translation initiation, the unwinding activity of the ribosome complex can function even on high affinity duplexes so that translation can proceed. (Liebhaber. J. Mol. Biol. 1992; 226: 2-13; Monia, et al. J Biol Chem. 1993; 268: 14514-22.)

It will be understood that any of the above described methods for enhancing the stability of mRNA may be used either alone or in combination with one or more of any of the other above-described methods and/or compositions.

The mRNA of the present invention may be optionally combined with a reporter gene (e.g., upstream or downstream of the coding region of the mRNA) which, for example, facilitates the determination of mRNA delivery to the target cells or tissues. Suitable reporter genes may include, for example, Green Fluorescent Protein mRNA (GFP mRNA), *Renilla* Luciferase mRNA (Luciferase mRNA), Firefly Luciferase mRNA, or any combinations thereof. For example, GFP mRNA may be fused with a mRNA encoding a secretable protein to facilitate confirmation of mRNA localization in the target cells that will act as a depot for protein production.

As used herein, the terms "transfect" or "transfection" mean the intracellular introduction of a mRNA into a cell, or preferably into a target cell. The introduced mRNA may be stably or transiently maintained in the target cell. The term "transfection efficiency" refers to the relative amount of mRNA taken up by the target cell which is subject to transfection. In practice, transfection efficiency is estimated by the amount of a reporter nucleic acid product expressed by the target cells following transfection. Preferred embodiments include compositions with high transfection efficacies and in particular those compositions that minimize adverse effects which are mediated by transfection of non-target cells. The compositions of the present invention that demonstrate high transfection efficacies improve the likelihood that appropriate dosages of the mRNA will be delivered to the target cell, while minimizing potential systemic adverse effects. In one embodiment of the present invention, the transfer vehicles of the present invention are capable of delivering large mRNA sequences (e.g., mRNA of at least 1 kDa, 1.5 kDa, 2 kDa, 2.5 kDa, 5 kDa, 10 kDa, 12 kDa, 15 kDa, 20 kDa, 25 kDa, 30 kDa, or more). The mRNA can be formulated with one or more acceptable reagents, which provide a vehicle for delivering such mRNA to target cells. Appropriate reagents are generally selected with regard to a number of factors, which include, among other things, the biological or chemical properties of the mRNA, the intended route of administration, the anticipated biological environment to which such mRNA will be exposed and the specific properties of the intended target cells. In some embodiments, transfer vehicles, such as liposomes, encapsulate the mRNA without compromising biological activity. In some embodiments, the transfer vehicle demonstrates preferential and/or substantial binding to a target cell relative to non-target cells. In a preferred embodiment, the transfer vehicle delivers its contents to the target cell such that the mRNA are delivered to the appropriate subcellular compartment, such as the cytoplasm.

Transfer Vehicle

In embodiments, the transfer vehicle in the compositions of the invention is a liposomal transfer vehicle, e.g. a lipid nanoparticle. In one embodiment, the transfer vehicle may be selected and/or prepared to optimize delivery of the mRNA to a target cell. For example, if the target cell is a hepatocyte the properties of the transfer vehicle (e.g., size, charge and/or pH) may be optimized to effectively deliver such transfer vehicle to the target cell, reduce immune clearance and/or promote retention in that target cell. Alternatively, if the target cell is the central nervous system (e.g., mRNA administered for the treatment of neurodegenerative diseases may specifically target brain or spinal tissue), selection and preparation of the transfer vehicle must consider penetration of, and retention within the blood brain barrier and/or the use of alternate means of directly delivering such transfer vehicle to such target cell. In one embodiment, the compositions of the present invention may be combined with agents that facilitate the transfer of exogenous mRNA (e.g., agents which disrupt or improve the permeability of the blood brain barrier and thereby enhance the transfer of exogenous mRNA to the target cells).

The use of liposomal transfer vehicles to facilitate the delivery of nucleic acids to target cells is contemplated by the present invention. Liposomes (e.g., liposomal lipid nanoparticles) are generally useful in a variety of applications in research, industry, and medicine, particularly for their use as transfer vehicles of diagnostic or therapeutic compounds in vivo (Lasic, Trends Biotechnol., 16: 307-321, 1998; Drummond et al., Pharmacol. Rev., 51: 691-743, 1999) and are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.).

In the context of the present invention, a liposomal transfer vehicle typically serves to transport the mRNA to the target cell. For the purposes of the present invention, the liposomal transfer vehicles are prepared to contain the desired nucleic acids. The process of incorporation of a desired entity (e.g., a nucleic acid) into a liposome is often referred to as "loading" (Lasic, et al., FEBS Lett., 312:

255-258, 1992). The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in a preferred embodiment of the present invention, the selected transfer vehicle is capable of enhancing the stability of the mRNA contained therein. The liposome can allow the encapsulated mRNA to reach the target cell and/or may preferentially allow the encapsulated mRNA to reach the target cell, or alternatively limit the delivery of such mRNA to other sites or cells where the presence of the administered mRNA may be useless or undesirable. Furthermore, incorporating the mRNA into a transfer vehicle, such as for example, a cationic liposome, also facilitates the delivery of such mRNA into a target cell.

Ideally, liposomal transfer vehicles are prepared to encapsulate one or more desired mRNA such that the compositions demonstrate a high transfection efficiency and enhanced stability. While liposomes can facilitate introduction of nucleic acids into target cells, the addition of polycations (e.g., poly L-lysine and protamine), as a copolymer can facilitate, and in some instances markedly enhance the transfection efficiency of several types of cationic liposomes by 2-28 fold in a number of cell lines both in vitro and in vivo. (See N.J. Caplen, et al., Gene Ther. 1995; 2: 603; S. Li, et al., Gene Ther. 1997; 4, 891.)

Lipid Nanoparticles

In a preferred embodiment of the present invention, the transfer vehicle is formulated as a lipid nanoparticle. As used herein, the phrase "lipid nanoparticle" refers to a transfer vehicle comprising one or more lipids (e.g., cationic lipids, non-cationic lipids, and PEG-modified lipids). Preferably, the lipid nanoparticles are formulated to deliver one or more mRNA to one or more target cells. Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine. In one embodiment, the transfer vehicle is selected based upon its ability to facilitate the transfection of a mRNA to a target cell.

The invention contemplates the use of lipid nanoparticles as transfer vehicles comprising a cationic lipid to encapsulate and/or enhance the delivery of mRNA into the target cell that will act as a depot for protein production. As used herein, the phrase "cationic lipid" refers to any of a number of lipid species that carry a net positive charge at a selected pH, such as physiological pH. The contemplated lipid nanoparticles may be prepared by including multi-component lipid mixtures of varying ratios employing one or more cationic lipids, non-cationic lipids and PEG-modified lipids. Several cationic lipids have been described in the literature, many of which are commercially available.

Particularly suitable cationic lipids for use in the compositions and methods of the invention include those described in international patent publication WO 2010/053572, incorporated herein by reference, and most particularly, C12-200 described at paragraph [00225] of WO 2010/053572. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z,18Z)-N,N-dimethyl-6-(9Z,12Z)-octadeca-9,12-dien-1-yl)tetracosa-15,18-dien-1-amine (HGT5000), (15Z,18Z)-N,N-dimethyl-6-((9Z,12Z)-octadeca-9,12-dien-1-yl)tetracosa-4,15,18-trien-1-amine (HGT5001), and (15Z,18Z)-N,N-dimethyl-6-((9Z,12Z)-octadeca-9,12-dien-1-yl)tetracosa-5,15,18-trien-1-amine (HGT5002).

In some embodiments, the cationic lipid N-[1-(2,3-dioleyloxy)propyl]-N,N,N-trimethylammonium chloride or "DOTMA" is used. (Felgner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethy 1-1-(cis,cis-9', 1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-K-DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28:172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1).

The use of cholesterol-based cationic lipids is also contemplated by the present invention. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE.

In addition, several reagents are commercially available to enhance transfection efficacy. Suitable examples include LIPOFECTIN (DOTMA:DOPE) (Invitrogen, Carlsbad, California), LIPOFECTAMINE (DOSPA:DOPE) (Invitrogen), LIPOFECTAMINE2000. (Invitrogen), FUGENE, TRANSFECTAM (DOGS), and EFFECTENE.

Also contemplated are cationic lipids such as the dialkylamino-based, imidazole-based, and guanidinium-based lipids. For example, certain embodiments are directed to a composition comprising one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by structure (I) below. In a preferred embodiment, a transfer vehicle for delivery of mRNA may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a] phenanthren-3-yl 3-(1H-imidazol-4-yl)propanoate, as represented by structure (I).

(I)

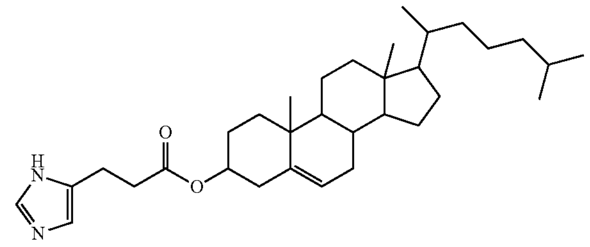

Without wishing to be bound by a particular theory, it is believed that the fusogenicity of the imidazole-based cationic lipid ICE is related to the endosomal disruption which is facilitated by the imidazole group, which has a lower pKa relative to traditional cationic lipids. The endosomal disruption in turn promotes osmotic swelling and the disruption of the liposomal membrane, followed by the transfection or intracellular release of the nucleic acid(s) contents loaded therein into the target cell.

The imidazole-based cationic lipids are also characterized by their reduced toxicity relative to other cationic lipids. The imidazole-based cationic lipids (e.g., ICE) may be used as the sole cationic lipid in the lipid nanoparticle, or alternatively may be combined with traditional cationic lipids, non-cationic lipids, and PEG-modified lipids. The cationic lipid may comprise a molar ratio of about 1% to about 90%, about 2% to about 70%, about 5% to about 50%, about 10% to about 40% of the total lipid present in the transfer vehicle, or preferably about 20% to about 70% of the total lipid present in the transfer vehicle.

Similarly, certain embodiments are directed to lipid nanoparticles comprising the HGT4003 cationic lipid 2-((2,3-Bis((9Z,12Z)-octadeca-9,12-dien-1-yloxy)propyl)disulfanyl)-N,N-dimethylethanamine, as represented by structure (II) below, and as further described in U.S. Provisional Application No. 61/494,745, filed Jun. 8, 2011, the entire teachings of which are incorporated herein by reference in their entirety:

(I)

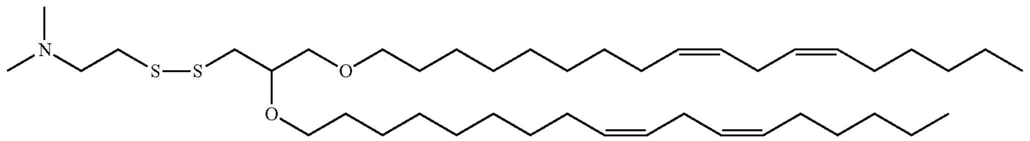

In other embodiments the compositions and methods described herein are directed to lipid nanoparticles comprising one or more cleavable lipids, such as, for example, one or more cationic lipids or compounds that comprise a cleavable disulfide (S-S) functional group (e.g., HGT4001, HGT4002, HGT4003, HGT4004 and HGT4005), as further described in U.S. Provisional Application No. 61/494,745, the entire teachings of which are incorporated herein by reference in their entirety.

The use of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipids together which comprise the transfer vehicle (e.g., a lipid nanoparticle). Contemplated PEG-modified lipids include, but is not limited to, a polyethylene glycol chain of up to 5 kDa in length covalently attached to a lipid with alkyl chain(s) of C6-C20 length. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-

237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

The present invention also contemplates the use of non-cationic lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone, but are preferably used in combination with other excipients, for example, cationic lipids. When used in combination with a cationic lipid, the non-cationic lipid may comprise a molar ratio of 5% to about 90%, or preferably about 10% to about 70% of the total lipid present in the transfer vehicle.

Preferably, the transfer vehicle (e.g., a lipid nanoparticle) is prepared by combining multiple lipid and/or polymer components. For example, a transfer vehicle may be prepared using C12-200, DOPE, chol, DMG-PEG2K at a molar ratio of 40:30:25:5, or DODAP, DOPE, cholesterol, DMG-PEG2K at a molar ratio of 18:56:20:6, or HGT5000, DOPE, chol, DMG-PEG2K at a molar ratio of 40:20:35:5, or HGT5001, DOPE, chol, DMG-PEG2K at a molar ratio of 40:20:35:5. The selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly. For example, in embodiments, the percentage of cationic lipid in the lipid nanoparticle may be greater than 10%, greater than 20%, greater than 30%, greater than 40%, greater than 50%, greater than 60%, or greater than 70%. The percentage of non-cationic lipid in the lipid nanoparticle may be greater than 5%, greater than 10%, greater than 20%, greater than 30%, or greater than 40%. The percentage of cholesterol in the lipid nanoparticle may be greater than 10%, greater than 20%, greater than 30%, or greater than 40%. The percentage of PEG-modified lipid in the lipid nanoparticle may be greater than 1%, greater than 2%, greater than 5%, greater than 10%, or greater than 20%.

In certain preferred embodiments, the lipid nanoparticles of the invention comprise at least one of the following cationic lipids: C12-200, DLin-KC2-DMA, DODAP, HGT4003, ICE, HGT5000, or HGT5001. In embodiments, the transfer vehicle comprises cholesterol and/or a PEG-modified lipid. In some embodiments, the transfer vehicles comprises DMG-PEG2K. In certain embodiments, the tranfer vehicle comprises one of the following lipid formulations: C12-200, DOPE, chol, DMG-PEG2K; DODAP, DOPE, cholesterol, DMG-PEG2K; HGT5000, DOPE, chol, DMG-PEG2K, HGT5001, DOPE, chol, DMG-PEG2K.

The liposomal transfer vehicles for use in the compositions of the invention can be prepared by various techniques which are presently known in the art. Multi-lamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments of this invention, the compositions of the present invention comprise a transfer vehicle wherein the mRNA is associated on both the surface of the transfer vehicle and encapsulated within the same transfer vehicle. For example, during preparation of the compositions of the present invention, cationic liposomal transfer vehicles may associate with the mRNA through electrostatic interactions.

In certain embodiments, the compositions of the invention may be loaded with diagnostic radionuclide, fluorescent materials or other materials that are detectable in both in vitro and in vivo applications. For example, suitable diagnostic materials for use in the present invention may include Rhodamine-dioleoylphospha-tidylethanolamine (Rh-PE), Green Fluorescent Protein mRNA (GFP mRNA), *Renilla* Luciferase mRNA and Firefly Luciferase mRNA.

Selection of the appropriate size of a liposomal transfer vehicle must take into consideration the site of the target cell or tissue and to some extent the application for which the liposome is being made. In some embodiments, it may be desirable to limit transfection of the mRNA to certain cells or tissues. For example, to target hepatocytes a liposomal transfer vehicle may be sized such that its dimensions are smaller than the fenestrations of the endothelial layer lining hepatic sinusoids in the liver; accordingly the liposomal transfer vehicle can readily penetrate such endothelial fenestrations to reach the target hepatocytes. Alternatively, a liposomal transfer vehicle may be sized such that the dimensions of the liposome are of a sufficient diameter to limit or expressly avoid distribution into certain cells or tissues. For example, a liposomal transfer vehicle may be sized such that its dimensions are larger than the fenestrations of the endothelial layer lining hepatic sinusoids to thereby limit distribution of the liposomal transfer vehicle to hepatocytes. Generally, the size of the transfer vehicle is within the range of about 25 to 250 nm, preferably less than about 250 nm, 175 nm, 150 nm, 125 nm, 100 nm, 75 nm, 50 nm, 25 nm or 10 nm.

A variety of alternative methods known in the art are available for sizing of a population of liposomal transfer vehicles. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, Ann. Rev. Biophys. Bioeng., 10:421-450 (1981), incorporated herein by reference. Average liposome diameter may be reduced by sonication of formed liposomes. Intermittent sonication cycles may be alternated with QELS assessment to guide efficient liposome synthesis.

Target Cells

As used herein, the term "target cell" refers to a cell or tissue to which a composition of the invention is to be directed or targeted. In some embodiments, the target cells are deficient in a protein or enzyme of interest. For example, where it is desired to deliver a nucleic acid to a hepatocyte, the hepatocyte represents the target cell. In some embodiments, the compositions of the invention transfect the target cells on a discriminatory basis (i.e., do not transfect non-target cells). The compositions of the invention may also be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

The compositions of the invention may be prepared to preferentially distribute to target cells such as in the heart, lungs, kidneys, liver, and spleen. In some embodiments, the compositions of the invention distribute into the cells of the liver to facilitate the delivery and the subsequent expression of the mRNA comprised therein by the cells of the liver (e.g., hepatocytes). The targeted hepatocytes may function as a biological "reservoir" or "depot" capable of producing, and systemically excreting a functional protein or enzyme. Accordingly, in one embodiment of the invention the liposomal transfer vehicle may target hepatocytes and/or preferentially distribute to the cells of the liver upon delivery. Following transfection of the target hepatocytes, the mRNA loaded in the liposomal vehicle are translated and a functional protein product is produced, excreted and systemically distributed. In other embodiments, cells other than hepatocytes (e.g., lung, spleen, heart, ocular, or cells of the central nervous system) can serve as a depot location for protein production.

In one embodiment, the compositions of the invention facilitate a subject's endogenous production of one or more functional proteins and/or enzymes, and in particular the production of proteins and/or enzymes which demonstrate less immunogenicity relative to their recombinantly-prepared counterparts. In a preferred embodiment of the present invention, the transfer vehicles comprise mRNA which encode a deficient protein or enzyme. Upon distribution of such compositions to the target tissues and the subsequent transfection of such target cells, the exogenous mRNA loaded into the liposomal transfer vehicle (e.g., a lipid nanoparticle) may be translated in vivo to produce a functional protein or enzyme encoded by the exogenously administered mRNA (e.g., a protein or enzyme in which the subject is deficient). Accordingly, the compositions of the present invention exploit a subject's ability to translate exogenously- or recombinantly-prepared mRNA to produce an endogenously-translated protein or enzyme, and thereby produce (and where applicable excrete) a functional protein or enzyme. The expressed or translated proteins or enzymes may also be characterized by the in vivo inclusion of native post-translational modifications which may often be absent in recombinantly-prepared proteins or enzymes, thereby further reducing the immunogenicity of the translated protein or enzyme.

The administration of mRNA encoding a deficient protein or enzyme avoids the need to deliver the nucleic acids to specific organelles within a target cell (e.g., mitochondria). Rather, upon transfection of a target cell and delivery of the nucleic acids to the cytoplasm of the target cell, the mRNA contents of a transfer vehicle may be translated and a functional protein or enzyme expressed.

The present invention also contemplates the discriminatory targeting of target cells and tissues by both passive and active targeting means. The phenomenon of passive targeting exploits the natural distributions patterns of a transfer vehicle in vivo without relying upon the use of additional excipients or means to enhance recognition of the transfer vehicle by target cells. For example, transfer vehicles which are subject to phagocytosis by the cells of the reticulo-endothelial system are likely to accumulate in the liver or spleen, and accordingly may provide means to passively direct the delivery of the compositions to such target cells.

Alternatively, the present invention contemplates active targeting, which involves the use of additional excipients, referred to herein as "targeting ligands" that may be bound (either covalently or non-covalently) to the transfer vehicle to encourage localization of such transfer vehicle at certain target cells or target tissues. For example, targeting may be mediated by the inclusion of one or more endogenous targeting ligands (e.g., apolipoprotein E) in or on the transfer vehicle to encourage distribution to the target cells or tissues. Recognition of the targeting ligand by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes). As provided herein, the composition can comprise a ligand capable of enhancing affinity of the composition to the target cell. Targeting ligands may be linked to the outer bilayer of the lipid particle during formulation or post-formulation. These methods are well known in the art. In addition, some lipid particle formulations may employ fusogenic polymers such as PEAA, hemagluttinin, other lipopeptides (see U.S. patent application Ser. Nos. 08/835,281, and 60/083,294, which are incorporated herein by reference) and other features useful for in vivo and/or intracellular delivery. In other some embodiments, the compositions of the present invention demonstrate improved transfection efficacies, and/or demonstrate enhanced selectivity towards target cells or tissues of interest. Contemplated therefore are compositions which comprise one or more ligands (e.g., peptides, aptamers, oligonucleotides, a vitamin or other molecules) that are capable of enhancing the affinity of the compositions and their nucleic acid contents for the target cells or tissues. Suitable ligands may optionally be bound or linked to the surface of the transfer vehicle. In some embodiments, the targeting ligand may span the surface of a transfer vehicle or be encapsulated within the transfer vehicle. Suitable ligands and are selected based upon their physical, chemical or biological properties (e.g., selective affinity and/or recognition of target cell surface markers or features.) Cell-specific target sites and their corresponding targeting ligand can vary widely. Suitable targeting ligands are selected such that the unique characteristics of a target cell are exploited, thus allowing the composition to discriminate between target and non-target cells. For example, compositions of the invention may include surface markers (e.g., apolipoprotein-B or apolipoprotein-E) that selectively enhance recognition of, or affinity to hepatocytes (e.g., by receptor-mediated recognition of and binding to such surface markers). Additionally, the use of galactose as a targeting ligand would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting ligands that have been conjugated to moieties present in the transfer vehicle (e.g., a lipid nanoparticle) therefore facilitate recognition and uptake of the compositions of the present invention in target cells and tissues. Examples of suitable targeting ligands include one or more peptides, proteins, aptamers, vitamins and oligonucleotides.

Application and Administration

As used herein, the term "subject" refers to any animal (e.g., a mammal), including, but not limited to, humans, non-human primates, rodents, and the like, to which the compositions and methods of the present invention are administered. Typically, the terms "subject" and "patient" are used interchangeably herein in reference to a human subject.

The compositions and methods of the invention provide for the delivery of mRNA to treat a number of disorders. In particular, the compositions and methods of the present invention are suitable for the treatment of diseases or disorders relating to the deficiency of proteins and/or enzymes that are excreted or secreted by the target cell into the surrounding extracellular fluid (e.g., mRNA encoding hormones and neurotransmitters). In embodiments the disease may involve a defect or deficiency in a secreted protein (e.g. Fabry disease, or ALS). In certain embodiments, the disease may not be caused by a defect or deficit in a secreted protein, but may benefit from providing a secreted protein. For example, the symptoms of a disease may be improved by providing the compositions of the invention (e.g. cystic fibrosis). Disorders for which the present invention are useful include, but are not limited to, disorders such as Huntington's Disease; Parkinson's Disease; muscular dystrophies (such as, e.g. Duchenne and Becker); hemophilia diseases (such as, e.g., hemophilia B (FIX), hemophilia A (FVIII); SMN1-related spinal muscular atrophy (SMA); amyotrophic lateral sclerosis (ALS); GALT-related galactosemia; Cystic Fibrosis (CF); SLC3A1-related disorders including cystinuria; COL4A5-related disorders including Alport syndrome; galactocerebrosidase deficiencies; X-linked adrenoleukodystrophy and adrenomyeloneuropathy; Friedreich's ataxia; Pelizaeus-Merzbacher disease; TSC1 and TSC2-related tuberous sclerosis; Sanfilippo B syndrome (MPS IIIB); CTNS-related cystinosis; the FMR1-related disorders which include Fragile X syndrome, Fragile X-Associated Tremor/Ataxia Syndrome and Fragile X Premature Ovarian Failure Syndrome; Prader-Willi syndrome; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; Wilson's disease; and Fabry Disease. In one embodiment, the nucleic acids, and in particular mrRNA, of the invention may encode functional proteins or enzymes that are secreted into extracellular space. For example, the secreted proteins include clotting factors, components of the complement pathway, cvtokines, chemokines, chemoattractants, protein hormones (e.g. EGF. PDF), protein components of serum, antibodies, secretable toll-like receptors, and others. In some embodiments, the compositions of the present invention may include mRNA encoding erythropoietin α1-antitrypsin. carboxypeptidase N or human growth hormone.

In embodiments, the invention encodes a secreted protein that is made up of subunits that are encoded by more than one gene. For example, the secreted protein may be a heterodimer, wherein each chain or subunit of the is encoded by a separate gene. It is possible that more than one mRNA molecule is delivered in the transfer vehicle and the mRNA encodes separate subunit of the secreted protein. Alternatively, a single mRNA may be engineered to encode more than one subunit (e.g. in the case of a single-chain Fv antibody). In certain embodiments, separate mRNA molecules encoding the individual subunits may be administered in separate transfer vehicles. In one embodiment, the mRNA may encode full length antibodies (both heavy and light chains of the variable and constant regions) or fragments of antibodies (e.g. Fab, Fv, or a single chain Fv (scFv) to confer immunity to a subject. While one embodiment of the present invention relates to methods and compositions useful for conferring immunity to a subject (e.g., via the translation of mRNA encoding functional antibodies), the inventions disclosed herein and contemplated hereby are broadly applicable. In an alternative embodiment the compositions of the present invention encode antibodies that may be used to transiently or chronically effect a functional response in subjects. For example, the mRNA of the present invention may encode a functional monoclonal or polyclonal antibody, which upon translation and secretion from target cell may be useful for targeting and/or inactivating a biological target (e.g., a stimulatory cytokine such as tumor necrosis factor). Similarly, the mRNA nucleic acids of the present invention may encode, for example, functional anti-nephritic factor antibodies useful for the treatment of membranoproliferative glomerulonephritis type II or acute hemolytic uremic syndrome, or alternatively may encode anti-vascular endothelial growth factor (VEGF) antibodies useful for the treatment of VEGF-mediated diseases, such as cancer. In other embodiments, the secreted protein is a cytokine or other secreted protein comprised of more than one subunit (e.g. IL-12, or IL-23).

The compositions of the invention can be administered to a subject. In some embodiments, the composition is formulated in combination with one or more additional nucleic acids, carriers, targeting ligands or stabilizing reagents, or in pharmacological compositions where it is mixed with suitable excipients. For example, in one embodiment, the compositions of the invention may be prepared to deliver mRNA encoding two or more distinct proteins or enzymes. Techniques for formulation and administration of drugs may be found in "Remington's Pharmaceutical Sciences," Mack Publishing Co., Easton, Pennsylvania, latest edition.

A wide range of molecules that can exert pharmaceutical or therapeutic effects can be delivered into target cells using compositions and methods of the invention. The molecules can be organic or inorganic. Organic molecules can be peptides, proteins, carbohydrates, lipids, sterols, nucleic acids (including peptide nucleic acids), or any combination thereof. A formulation for delivery into target cells can comprise more than one type of molecule, for example, two different nucleotide sequences, or a protein, an enzyme or a steroid.

The compositions of the present invention may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein production.

Suitable routes of administration include, for example, oral, rectal, vaginal, transmucosal, pulmonary including intratracheal or inhaled, or intestinal administration; parenteral delivery, including intramuscular, subcutaneous, intramedullary injections, as well as intrathecal, direct intraventricular, intravenous, intraperitoneal, intranasal, or intraocular injections.

Alternately, the compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present invention complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In one embodiment, the compositions of the invention are formulated such that they are suitable for extended-release of the mRNA contained therein. Such extended-release compositions may be conveniently administered to a subject at extended dosing intervals. For example, in one embodiment, the compositions of the present invention are administered to a subject twice day, daily or every other day. In a preferred embodiment, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and liposomal vehicles which are formulated for depot administration (e.g., intramuscularly, subcutaneously, intravitreally) to either deliver or release a mRNA over extended periods of time. Preferably, the extended-release means employed are combined with modifications made to the mRNA to enhance stability.

Also contemplated herein are lyophilized pharmaceutical compositions comprising one or more of the liposomal nanoparticles disclosed herein and related methods for the use of such lyophilized compositions as disclosed for example, in U.S. Provisional Application No. 61/494,882, filed Jun. 8, 2011, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

While certain compounds, compositions and methods of the present invention have been described with specificity in accordance with certain embodiments, the following examples serve only to illustrate the compounds of the invention and are not intended to limit the same. Each of the publications, reference materials, accession numbers and the like referenced herein to describe the background of the invention and to provide additional detail regarding its practice are hereby incorporated by reference in their entirety.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1: Protein Production Depot Via Intravenous Delivery of Polynucleotide Compositions Messenger RNA Human erythropoietin (EPO) (SEQ ID NO: 3; FIG. 3), human alpha-galactosidase (GLA) (SEQ ID NO: 4; FIG. 4), human alpha-1 antitrypsin (A1AT) (SEQ ID NO: 5; FIG. 5), and human factor IX (FIX) (SEQ ID NO: 6; FIG. 6) were synthesized by in vitro transcription from a plasmid DNA template encoding the gene, which was followed by the addition of a 5' cap structure (Cap1) (Fechter & Brownlee, J Gen. Virology 86:1239-1249 (2005)) and a 3' poly(A) tail of approximately 200 nucleotides in length as determined by gel electrophoresis. 5' and 3' untranslated regions were present in each mRNA product in the following examples and are defined by SEQ ID NOs: 1 and 2 (FIG. 1 and FIG. 2) respectively.

Lipid Nanoparticle Formulations Formulation 1: Aliquots of 50 mg/mL ethanolic solutions of C12-200, DOPE, Chol and DMG-PEG2K (40:30:25:5) were mixed and diluted with ethanol to 3 mL final volume. Separately, an aqueous buffered solution (10 mM citrate/150 mM NaCl, pH 4.5) of mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C.

Formulation 2: Aliquots of 50 mg/mL ethanolic solutions of DODAP, DOPE, cholesterol and DMG-PEG2K (18:56:20:6) were mixed and diluted with ethanol to 3 mL final volume. Separately, an aqueous buffered solution (10 mM citrate/150 mM NaCl, pH 4.5) of EPO mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.35 mg/mL EPO mRNA (encapsulated). $Z_{ave}$=75.9 nm ($Dv_{(50)}$=57.3 nm; $Dv_{(90)}$=92.1 nm).

Formulation 3: Aliquots of 50 mg/mL ethanolic solutions of HGT4003, DOPE, cholesterol and DMG-PEG2K (50:25:20:5) were mixed and diluted with ethanol to 3 mL final volume. Separately, an aqueous buffered solution (10 mM citrate/150 mM NaCl, pH 4.5) of mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C.

Formulation 4: Aliquots of 50 mg/mL ethanolic solutions of ICE, DOPE and DMG-PEG2K (70:25:5) were mixed and diluted with ethanol to 3 mL final volume. Separately, an aqueous buffered solution (10 mM citrate/150 mM NaCl, pH 4.5) of mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C.

Formulation 5: Aliquots of 50 mg/mL ethanolic solutions of HGT5000, DOPE, cholesterol and DMG-PEG2K (40:20:35:5) were mixed and diluted with ethanol to 3 mL final volume. Separately, an aqueous buffered solution (10 mM citrate/150 mM NaCl, pH 4.5) of EPO mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.82 mg/mL EPO mRNA (encapsulated). $Z_{ave}$=105.6 nm ($Dv_{(50)}$=53.7 nm; $Dv_{(90)}$=157 nm).

Formulation 6: Aliquots of 50 mg/mL ethanolic solutions of HGT5001, DOPE, cholesterol and DMG-PEG2K (40:20:35:5) were mixed and diluted with ethanol to 3 mL final volume. Separately, an aqueous buffered solution (10 mM citrate/150 mM NaCl, pH 4.5) of EPO mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C.

Analysis of Protein Produced Via Intravenously Delivered mRNA-Loaded Nanoparticles Injection Protocol Studies were performed using male CD-1 mice of approximately 6-8 weeks of age at the beginning of each experiment, unless otherwise indicated. Samples were introduced by a single bolus tail-vein injection of an equivalent total dose of 30-200 micrograms of encapsulated mRNA. Mice were sacrificed and perfused with saline at the designated time points.

Isolation of Organ Tissues for Analysis

The liver and spleen of each mouse was harvested, apportioned into three parts, and stored in either 10% neutral buffered formalin or snap-frozen and stored at −80° C. for analysis.

Isolation of Serum for Analysis

All animals were euthanized by $CO_2$ asphyxiation 48 hours post dose administration (±5%) followed by thoracotomy and terminal cardiac blood collection. Whole blood (maximal obtainable volume) was collected via cardiac puncture on euthanized animals into serum separator tubes, allowed to clot at room temperature for at least 30 minutes, centrifuged at 22° C.±5° C. at 9300 g for 10 minutes, and the serum extracted. For interim blood collections, approximately 40-50 µL of whole blood was collected via facial vein puncture or tail snip. Samples collected from non treatment animals were used as a baseline for comparison to study animals.

Enzyme-Linked Immunosorbent Assay (ELISA) Analysis

EPO ELISA: Quantification of EPO protein was performed following procedures reported for human EPO ELISA kit (Quantikine IVD, R&D Systems, Catalog #Dep-00). Positive controls employed consisted of ultrapure and tissue culture grade recombinant human erythropoietin protein (R&D Systems, Catalog #286-EP and 287-TC, respectively). Detection was monitored via absorption (450 nm) on a Molecular Device Flex Station instrument.

GLA ELISA: Standard ELISA procedures were followed employing sheep anti-Alpha-galactosidase G-188 IgG as the capture antibody with rabbit anti-Alpha-galactosidase TK-88 IgG as the secondary (detection) antibody (Shire Human Genetic Therapies). Horseradish peroxidase (HRP)-conjugated goat anti-rabbit IgG was used for activation of the 3,3',5,5'-tetramethylbenzidine (TMB) substrate solution. The reaction was quenched using 2N $H_2SO_4$ after 20 minutes. Detection was monitored via absorption (450 nm) on a Molecular Device Flex Station instrument. Untreated mouse serum and human Alpha-galactosidase protein were used as negative and positive controls, respectively.

FIXELISA: Quantification of FIX protein was performed following procedures reported for human FIX ELISA kit (AssayMax, Assay Pro, Catalog #EF1009-1).

A1AT ELISA: Quantification of A1AT protein was performed following procedures reported for human A1AT ELISA kit (Innovative Research, Catalog #IRAPKT015).

Western Blot Analysis (EPO): Western blot analyses were performed using an anti-hEPO antibody (R&D Systems #MAB2871) and ultrapure human EPO protein (R&D Systems #286-EP) as the control.

Results

The work described in this example demonstrates the use of mRNA-encapsulated lipid nanoparticles as a depot source for the production of protein. Such a depot effect can be achieved in multiple sites within the body (i.e., liver, kidney, spleen, and muscle). Measurement of the desired exogenous-based protein derived from messenger RNA delivered via liposomal nanoparticles was achieved and quantified, and the secretion of protein from a depot using human erythropoietin (hEPO), human alpha-galactosidase (hGLA), human alpha-1 antitrypsin (hA1AT), and human Factor IX (hFIX) mRNA was demonstrated.

1A. In Vivo Human EPO Protein Production Results

The production of hEPO protein was demonstrated with various lipid nanoparticle formulations. Of four different cationic lipid systems, C12-200-based lipid nanoparticles produced the highest quantity of hEPO protein after four hours post intravenous administration as measured by ELISA (FIG. 7). This formulation (Formulation 1) resulted in 18.3 ug/mL hEPO protein secreted into the bloodstream. Normal hEPO protein levels in serum for human are 3.3-16.6 mIU/mL (NCCLS Document C28-P; Vol. 12, No. 2). Based on a specific activity of 120,000 IU/mg of EPO protein, that yields a quantity of 27.5-138 pg/mL hEPO protein in normal human individuals. Therefore, a single 30 ug dose of a C12-200-based cationic lipid formulation encapsulating hEPO mRNA yielded an increase in respective protein of over 100,000-fold physiological levels.

Of the lipid systems tested, the DODAP-based lipid nanoparticle formulation was the least effective. However, the observed quantity of human EPO protein derived from delivery via a DODAP-based lipid nanoparticle encapsulating EPO mRNA was 4.1 ng/mL, which is still greater than 30-fold over normal physiological levels of EPO protein (Table 1).

TABLE 1

Figure 8:
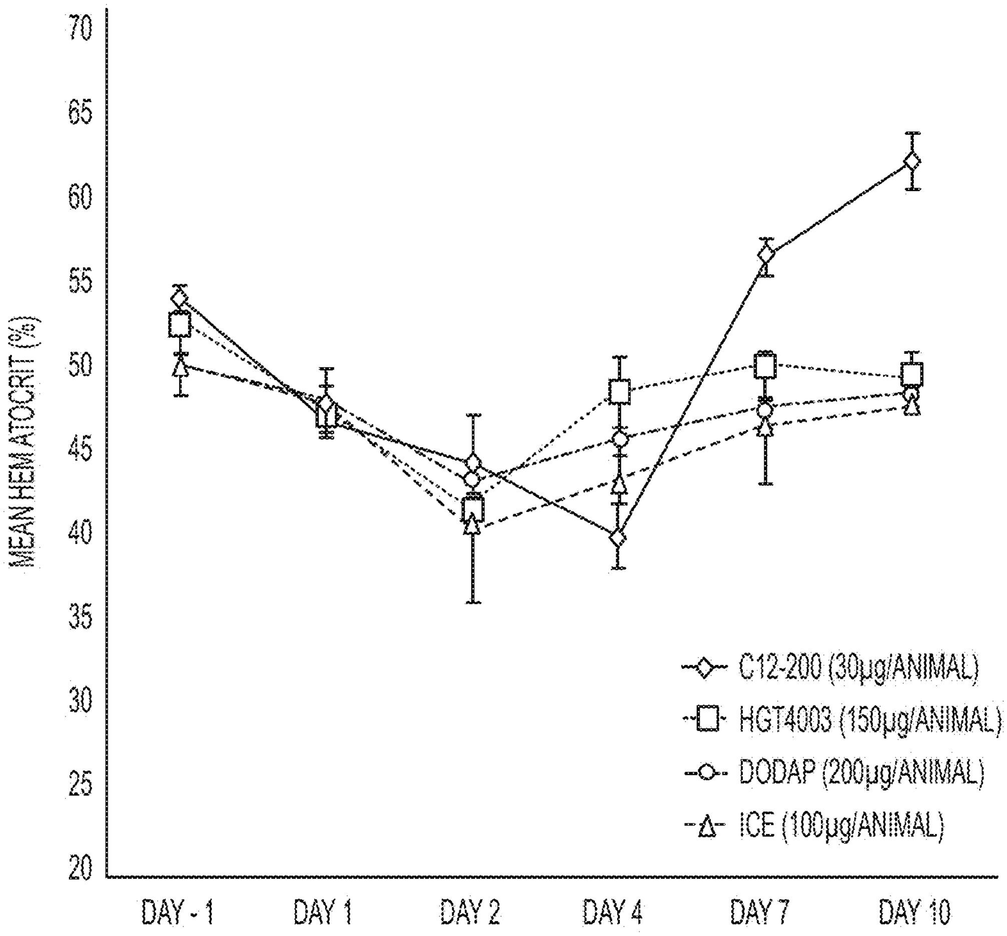
FIG. 8 shows the hematocrit measurement of mice treated with a single IV dose of human EPO mRNA-loaded lipid nanoparticles (Formulations 1-4). Whole blood samples were taken at 4 hr (Day 1), 24 hr (Day 2), 4 days, 7 days, and 10 days post-administration.

Raw values of secreted hEPO protein for various cationic lipid-based nanoparticle systems as measured via ELISA analysis (as depicted in FIG. 8). Doses are based on encapsulated hEPO mRNA. Values of protein are depicted as nanogram of human EPO protein per milliliter of serum. Hematocrit changes are based on comparison of pre-bleed (Day −1) and Day 10.

| Cationic/Ionizable Lipid Component | Dose of Encapsulated mRNA (ug) | Secreted Human EPO Protein (ng/mL) | Increase in Hematocrit (%) |
|---|---|---|---|
| C12-200 | 30 | 18,306 | 15.0 |
| HGT4003 | 150 | 164 | 0.0 |
| ICE | 100 | 56.2 | 0.0 |
| DODAP | 200 | 4.1 | 0.0 |

In addition, the resulting protein was tested to determine if it was active and functioned properly. In the case of mRNA replacement therapy (MRT) employing hEPO mRNA, hematocrit changes were monitored over a ten day period for five different lipid nanoparticle formulations (FIG. 8, Table 1) to evaluate protein activity. During this time period, two of the five formulations demonstrated an increase in hematocrit (≥15%), which is indicative of active hEPO protein being produced from such systems.

Figure 9:
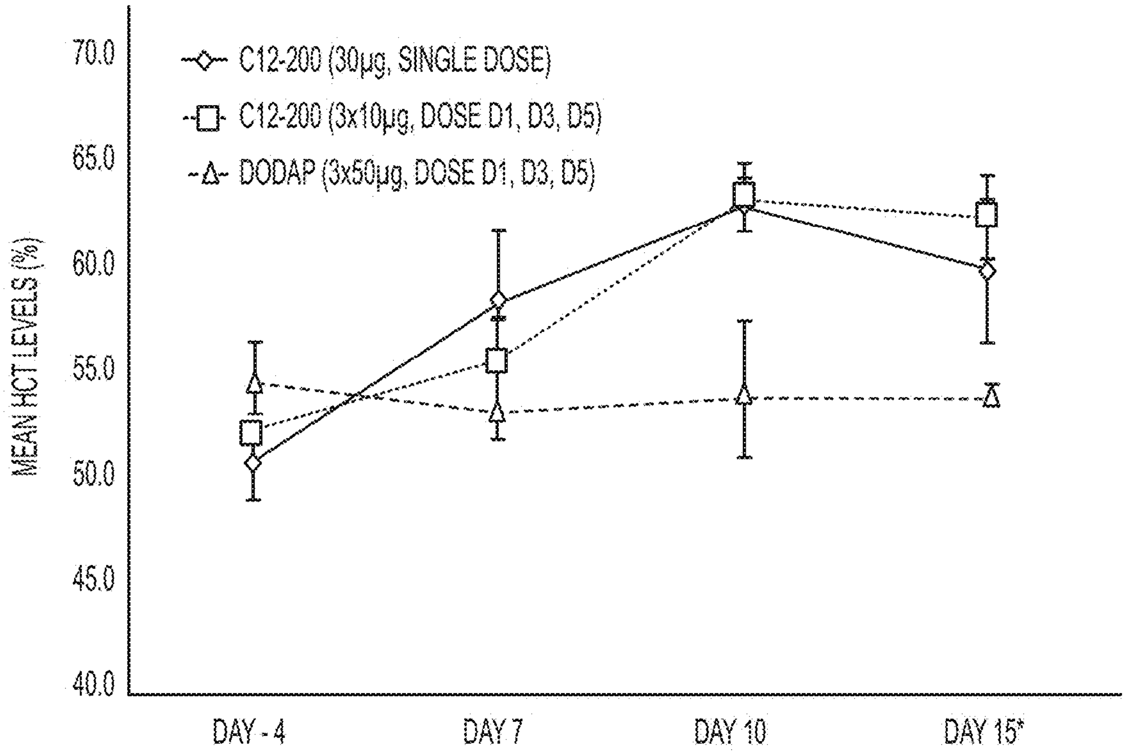
FIG. 9 shows hematocrit measurements of mice treated with human EPO-mRNA-loaded lipid nanoparticles with either a single IV dose or three injections (day 1, day 3, day 5). Whole blood samples were taken prior to injection (day −4), day 7, and day 15. Formulation 1 was administered: (30 ug, single dose) or (3×10 ug, dose day 1, day 3, day 5); Formulation 2 was administered: (3×50 ug, dose day 1, day 3, day 5).

In another experiment, hematocrit changes were monitored over a 15-day period (FIG. 9, Table 2). The lipid nanoparticle formulation (Formulation 1) was administered either as a single 30 µg dose, or as three smaller 10 µg doses injected on day 1, day 3 and day 5. Similarly, Formulation 2 was administered as 3 doses of 50 µg on day 1, day 3, and day 5. C12-200 produced a significant increase in hematocrit. Overall an increase of up to ~25% change was observed, which is indicative of active human EPO protein being produced from such systems.

TABLE 2

Hematocrit levels of each group over a 15 day observation period (FIG. 9). Mice were either dosed as a single injection, or three injections, every other day. N = 4 mice per group.

| Test Article | Dose (µg/animal) | Hct Levels Mean (%) ± SEM Day −4 | Day 7 | Day 10 | Day 15[a] |
|---|---|---|---|---|---|
| C12-200 | 30 (single dose) | 50.8 ± 1.8 | 58.3 ± 3.3 | 62.8 ± 1.3 | 59.9 ± 3.3 |
| C12-200 | 30 (over 3 doses) | 52.2 ± 0.5 | 55.3 ± 2.3 | 63.3 ± 1.6 | 62.3 ± 1.9 |
| DODAP | 150 (over 3 doses) | 54.8 ± 1.7 | 53.5 ± 1.6 | 54.2 ± 3.3 | 54.0 ± 0.3 |

Hct = hematocrit; SEM = standard error of the mean.
[a]Blood samples were collected into non-heparinized hematocrit tubes.

1B. In Vivo Human GLA Protein Production Results

A second exogenous-based protein system was explored to demonstrate the "depot effect" when employing mRNA-loaded lipid nanoparticles. Animals were injected intravenously with a single 30 microgram dose of encapsulated human alpha-galactosidase (hGLA) mRNA using a C12-200-based lipid nanoparticle system and sacrificed after six hours (Formulation 1). Quantification of secreted hGLA protein was performed via ELISA. Untreated mouse serum and human Alpha-galactosidase protein were used as controls. Detection of human alpha-galactosidase protein was monitored over a 48 hour period.

Figure 10:
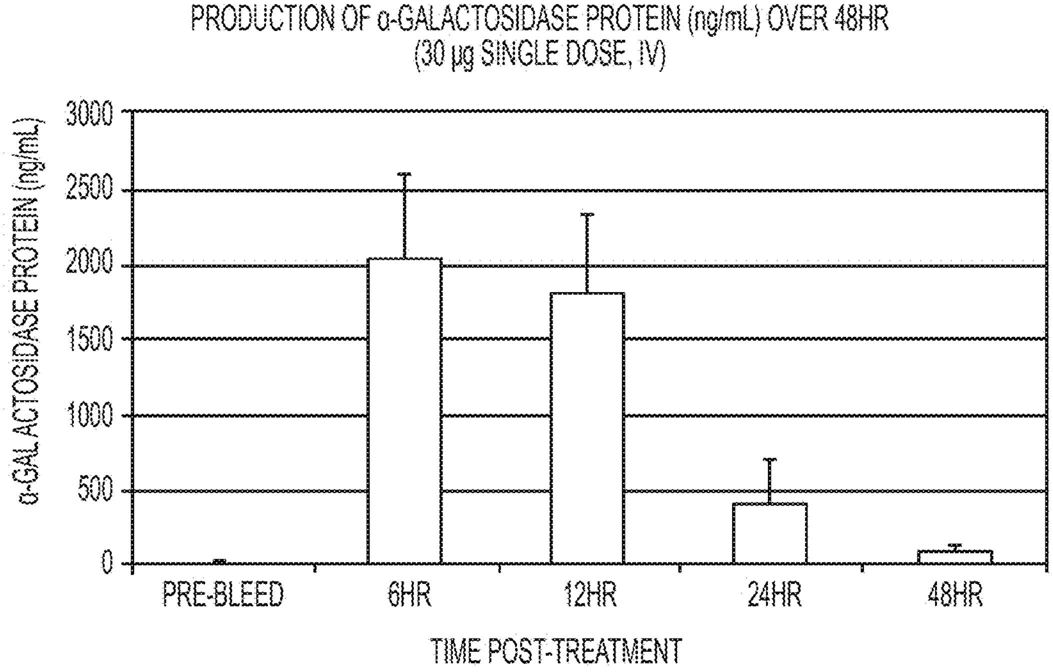
FIG. 10 shows quantification of secreted human α-galactosidase (hGLA) protein levels as measured via ELISA. The protein detected is a result of the production from hGLA mRNA delivered via lipid nanoparticles (Formulation 1; 30 ug single intravenous dose, based on encapsulated mRNA). hGLA protein is detected through 48 hours.

Measurable levels of hGLA protein were observed throughout the time course of the experiment with a maximum level of 2.0 ug/mL hGLA protein at six hours (FIG. 10). Table 3 lists the specific quantities of hGLA found in the serum. Normal activity in healthy human males has been reported to be approximately 3.05 nanomol/hr/mL. The activity for Alpha-galactosidase, a recombinant human alpha-galactosidase protein, $3.56\times10^6$ nanomol/hr/mg. Analysis of these values yields a quantity of approximately 856 pg/mL of hGLA protein in normal healthy male individuals. The quantity of 2.0 ug/mL hGLA protein observed after six hours when dosing a hGLA mRNA-loaded lipid nanoparticle is over 2300-fold greater than normal physiological levels. Further, after 48 hours, one can still detect appreciable levels of hGLA protein (86.2 ng/mL). This level is representative of almost 100-fold greater quantities of hGLA protein over physiological amounts still present at 48 hours.

TABLE 3

Raw values of secreted hGLA protein over time as measured via ELISA analysis (as depicted in FIG. 10). Values are depicted as nanogram of hGLA protein per milliliter of serum. N = 4 mice per group.

| Time Post-Administration (hr) | Secreted Human GLA Protein (ng/mL) |
|---|---|
| 6 | 2,038 |
| 12 | 1,815 |
| 24 | 414 |
| 48 | 86.2 |

In addition, the half-life of Alpha-galactosidase when administered at 0.2 mg/kg is approximately 108 minutes. Production of GLA protein via the "depot effect" when administering GLA mRNA-loaded lipid nanoparticles shows a substantial increase in blood residence time when compared to direct injection of the naked recombinant protein. As described above, significant quantities of protein are present after 48 hours.

Figure 11:
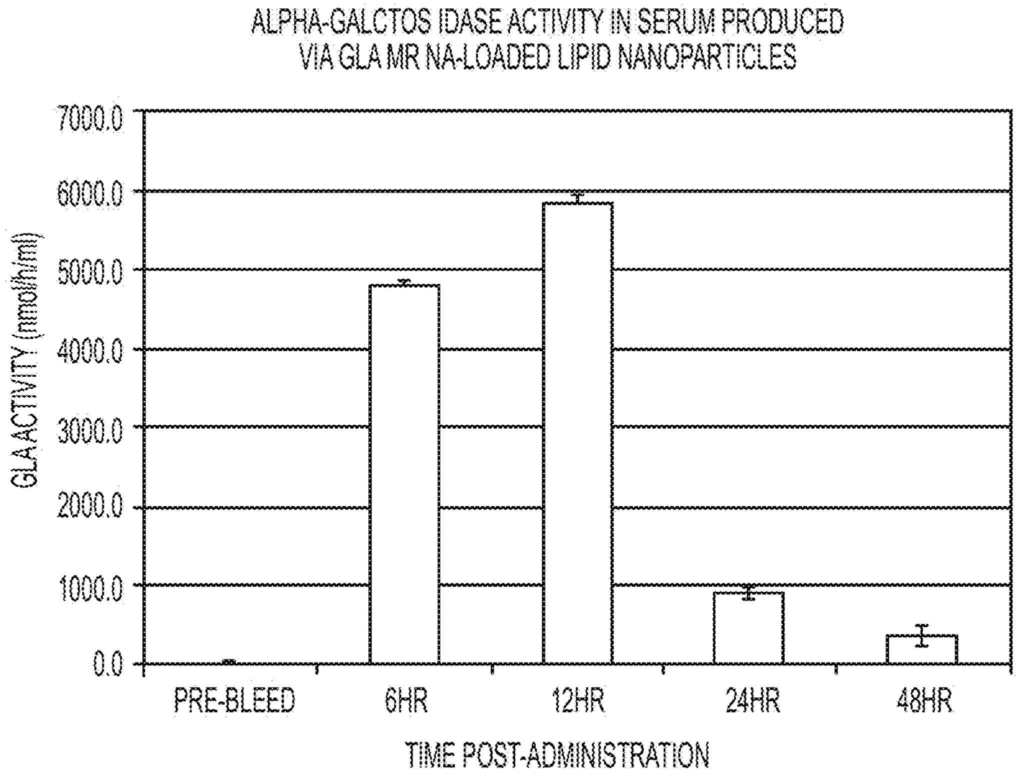
FIG. 11 shows hGLA activity in serum. hGLA activity was measured using substrate 4-methylumbelliferyl-α-D-galactopyranoside (4-MU-α-gal) at 37° C. Data are average of 6 to 9 individual measurements.
Figure 12:
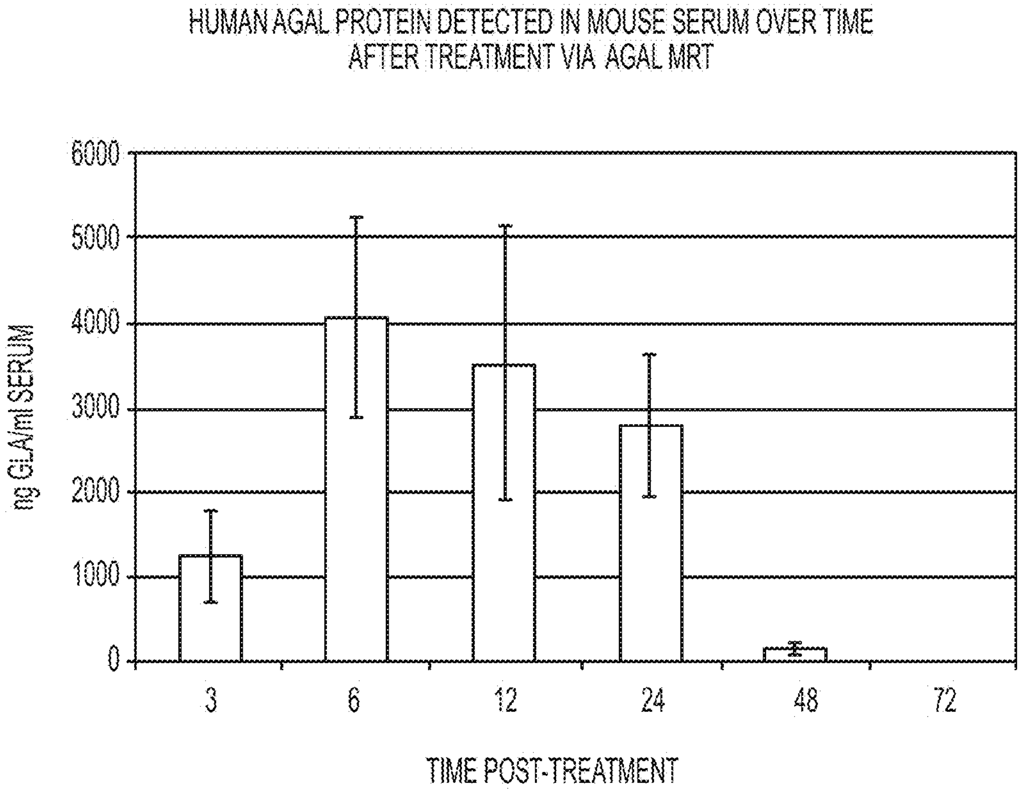
FIG. 12 shows quantification of hGLA protein levels in serum as measured via ELISA. Protein is produced from hGLA mRNA delivered via C12-200-based lipid nanoparticles (C12-200:DOPE:Chol:DMGPEG2K, 40:30:25:5 (Formulation 1); 30 ug mRNA based on encapsulated mRNA, single IV dose). hGLA protein is monitored through 72 hours. per single intravenous dose, based on encapsulated mRNA). hGLA protein is monitored through 72 hours.

The activity profile of the α-galactosidase protein produced from GLA mRNA-loaded lipid nanoparticles was measured as a function of 4-methylumbelliferyl-α-D-galactopyranoside (4-MU-α-gal) metabolism. As shown in FIG. 11, the protein produced from these nanoparticle systems is quite active and reflective of the levels of protein available (FIG. 12, Table 3). AUC comparisons of mRNA therapy-based hGLA production versus enzyme replacement therapy (ERT) in mice and humans show a 182-fold and 30-fold increase, respectively (Table 4).

TABLE 4

| | Test Article | Description | Dose (mg/kg) | $C_{max}$ (U/mL) | $AUC_{inf}$ (hr · U/mL) | n |
|---|---|---|---|---|---|---|
| Fabry[a] Patient | α-GAL Protein | Transplant | 0.2 | 3478 | 3683 | 11 |
| | | Dialysis | 0.2 | 3887 | 3600 | 6 |
| | | Non-ESRD[b] | 0.2 | 3710 | 4283 | 18 |
| Mouse | α-GAL Protein (MM1) | Athymic nude | 0.04 | 3807 | 797 | 3 |

TABLE 4-continued

| | Test Article | Description | Dose (mg/kg) | $C_{max}$ (U/mL) | $AUC_{inf}$ (hr · U/mL) | n |
|---|---|---|---|---|---|---|
| | α-GAL Protein (MM2) | Athymic nude | 0.04 | 3705 | 602 | 3 |
| Mouse | α-GAL mRNA | mouse | 0.95 | 5885 ($C_{at\ 6hr}$)[c] | 109428 | 6 |

Comparison of $C_{max}$ and $AUC_{inf}$ values in Fabry patients post-IV dosing 0.2 mg/kg of Alpha-galactosidase (pharmacological dose) with those in mice post-IV dosing Alpha-galactosidase and GLA mRNA.

[a]Data were from a published paper (Gregory M. Pastores et al. Safety and Pharmacokinetics of hGLA in patients with Fabry disease and end-stage renal disease. Nephrol Dial Transplant (2007) 22:1920-1925.

[b]non-end-stage renal disease.

[c]α-Galactosidase activity at 6 hours after dosing (the earliest time point tested in the study).

The ability of mRNA encapsulated lipid nanoparticles to target organs which can act as a depot for the production of a desired protein has been demonstrated. The levels of secreted protein observed have been several orders of magnitude above normal physiological levels. This "depot effect" is repeatable. FIG. 12 shows again that robust protein production is observed upon dosing wild type (CD-1) mice with a single 30 ug dose of hGLA mRNA-loaded in C12-200-based lipid nanoparticles (Formulation 1). In this experiment, hGLA levels were evaluated over a 72 hour period. A maximum average of 4.0 ug human hGLA protein/mL serum is detected six hours post-administration. Based on a value of ~1 ng/mL hGLA protein for normal physiological levels, hGLA MRT provides roughly 4000-fold higher protein levels. As before, hGLA protein could be detected out to 48 hr post-administration (FIG. 12).

Figure 13:
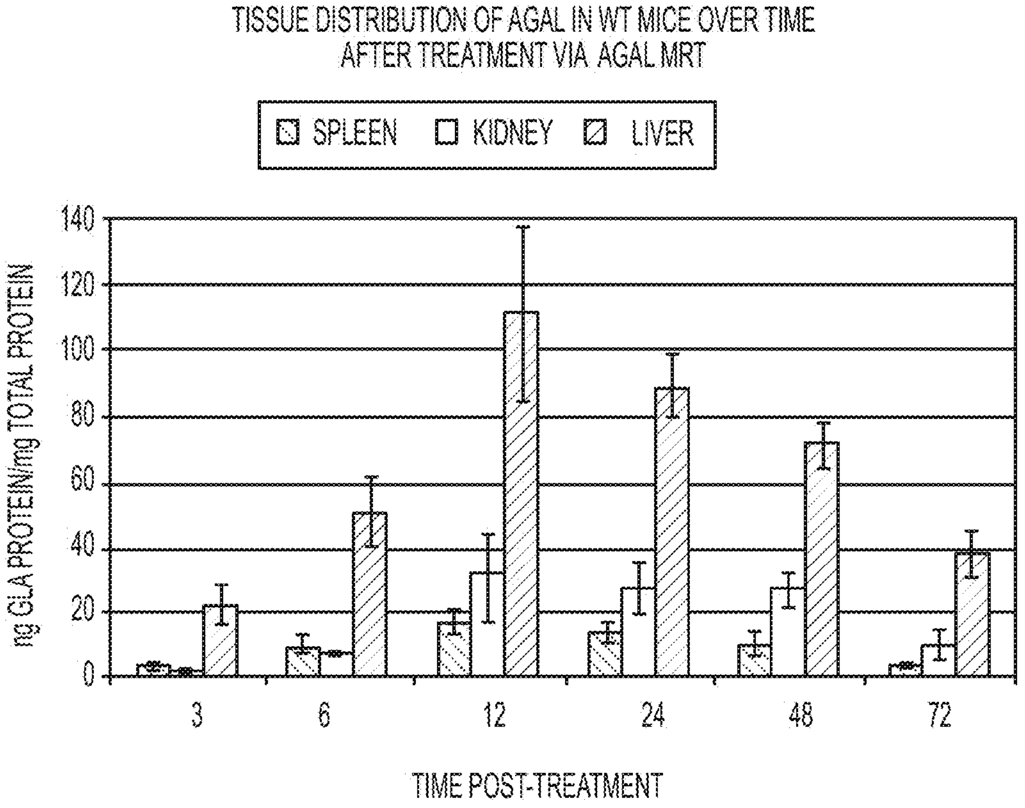
FIG. 13 shows quantification of hGLA protein levels in liver, kidney, and spleen as measured via ELISA. Protein is produced from hGLA mRNA delivered via C12-200-based lipid nanoparticles (Formulation 1; 30 ug mRNA based on encapsulated mRNA, single IV dose). hGLA protein is monitored through 72 hours.

An analysis of tissues isolated from this same experiment provided insight into the distribution of hGLA protein in hGLA MRT-treated mice (FIG. 13). Supraphysiological levels of hGLA protein were detected in the liver, spleen and kidneys of all mice treated with a maximum observed between 12 and 24 hour post-administration. Detectable levels of MRT-derived protein could be observed three days after a single injection of hGLA-loaded lipid nanoparticles.

Figure 14A:
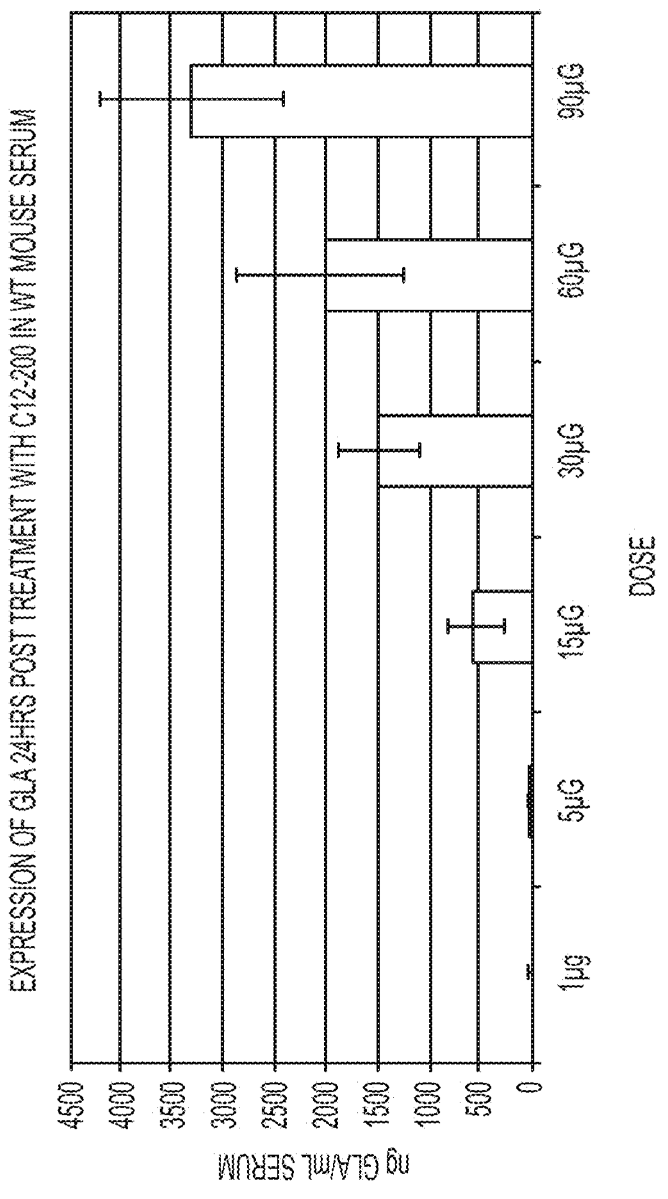
FIG. 14A shows a dose response study monitoring protein production of hGLA as secreted MRT-derived human GLA protein in serum. Samples were measured 24 hours post-administration (Formulation 1; single dose, IV, N=4 mice/group) and quantified via ELISA.
Figure 14B:
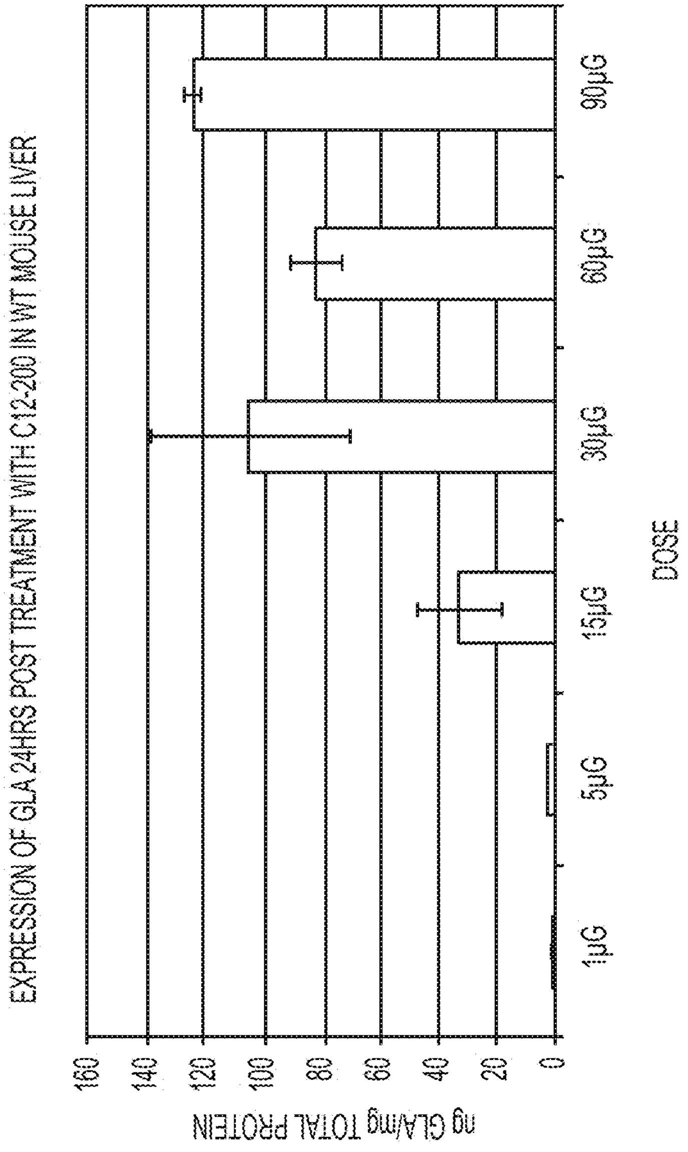
FIG. 14B shows a dose response study monitoring protein production of hGLA as secreted MRT-derived human GLA protein in liver. Samples were measured 24 hours post-administration (Formulation 1; single dose, IV, N=4 mice/group) and quantified via ELISA.

In addition, the production of hGLA upon administration of hGLA mRNA loaded C12-200 nanoparticles was shown to exhibit a dose a response in the serum (FIG. 14A), as well as in the liver (FIG. 14B).

Figure 15:
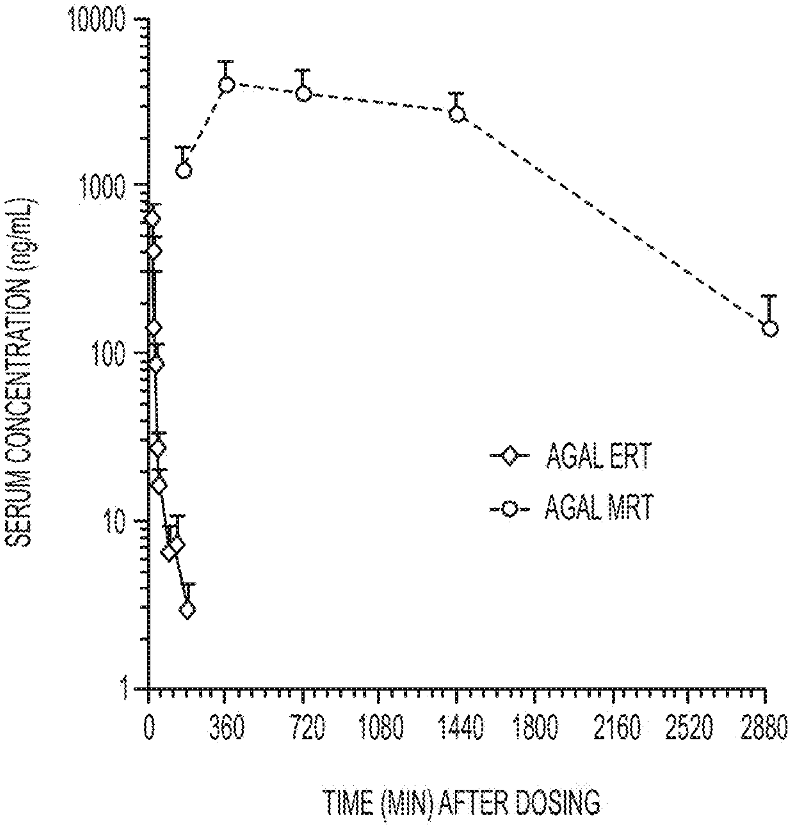
FIG. 15 shows the pharmacokinetic profiles of ERT-based Alpha-galactosidase in athymjic nude mice (40 ug/kg dose) and hGLA protein produced from MRT (Formulation 1; 1.0 mg/kg mRNA dose).

One inherent characteristic of lipid nanoparticle-mediated mRNA replacement therapy would be the pharmacokinetic profile of the respective protein produced. For example, ERT-based treatment of mice employing Alpha-galactosidase results in a plasma half-life of approximately 100 minutes. In contrast, MRT-derived alpha-galactosidase has a blood residence time of approximately 72 hrs with a peak time of 6 hours. This allows for much greater exposure for organs to participate in possible continuous uptake of the desired protein. A comparison of PK profiles is shown in FIG. 15 and demonstrates the stark difference in clearance rates and ultimately a major shift in area under the curve (AUC) can be achieved via MRT-based treatment.

Figure 16:
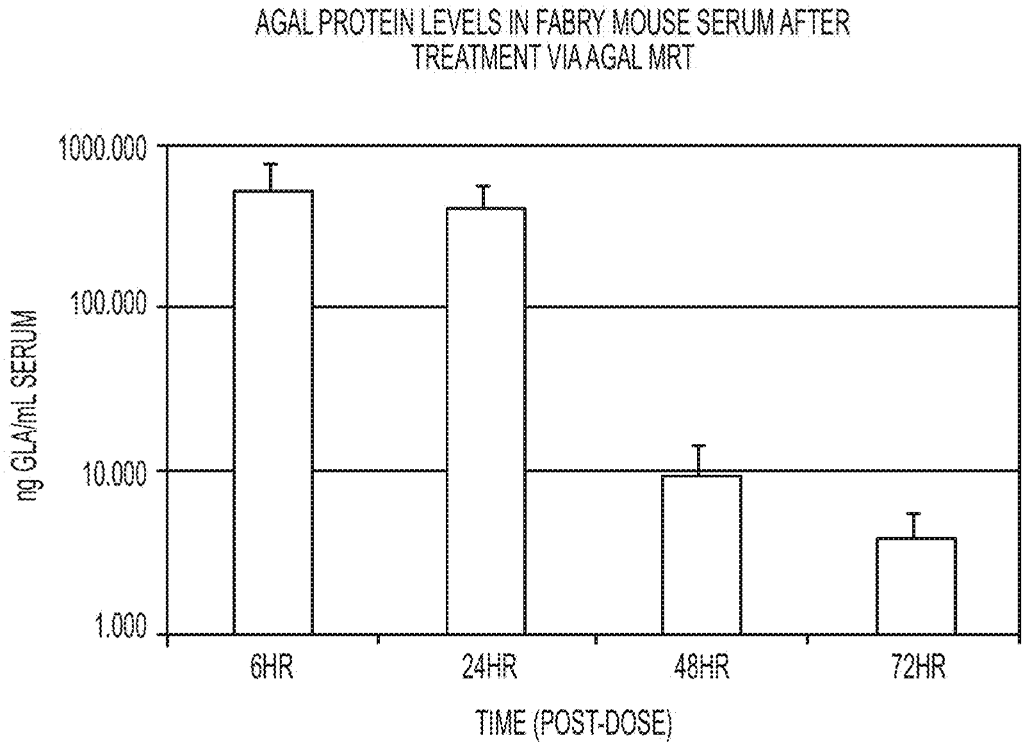
FIG. 16 shows the quantification of secreted hGLA protein levels in MRT-treated Fabry mice as measured using ELISA. hGLA protein is produced from hGLA mRNA delivered via C12-200-based lipid nanoparticles (Formulation 1; 10 ug mRNA per single intravenous dose, based on encapsulated mRNA). Serum is monitored through 72 hours.

In a separate experiment, hGLA MRT was applied to a mouse disease model, hGLA KO mice (Fabry mice). A 0.33 mg/kg dose of hGLA mRNA-loaded C12-200-based lipid nanoparticles (Formulation 1) was administered to female KO mice as a single, intravenous injection. Substantial quantities of MRT-derived hGLA protein were produced with a peak at 6 hr (~560 ng/mL serum) which is approximately 600-fold higher than normal physiological levels. Further, hGLA protein was still detectable 72 hr post-administration (FIG. 16).

Figure 17:
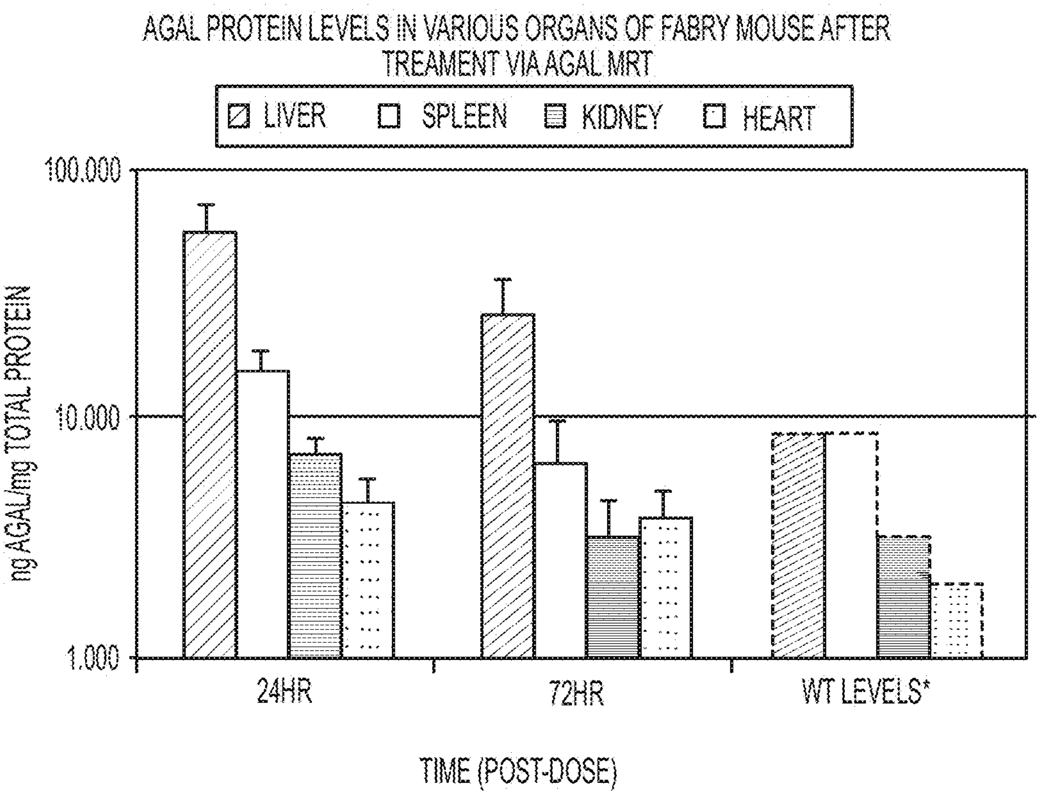
FIG. 17 shows the quantification of hGLA protein levels in liver, kidney, spleen, and heart of MRT-treated Fabry KO mice as measured via ELISA. Protein is produced from hGLA mRNA delivered via C12-200-based lipid nanoparticles (Formulation 1; 30 ug mRNA based on encapsulated mRNA, single IV dose). hGLA protein is monitored through 72 hours. Literature values representing normal physiological levels are graphed as dashed lines.

Quantification of MRT-derived GLA protein in vital organs demonstrated substantial accumulation as shown in FIG. 17. A comparison of observed MRT-derived hGLA protein to reported normal physiological levels that are found in key organs is plotted (normal levels plotted as dashed lines). While levels of protein at 24 hours are higher than at 72 hours post-administration, the levels of hGLA protein detected in the liver, kidney, spleen and hearts of the treated Fabry mice are equivalent to wild type levels. For example, 3.1 ng hGLA protein/mg tissue were found in the kidneys of treated mice 3 days after a single MRT treatment.

Figure 18:
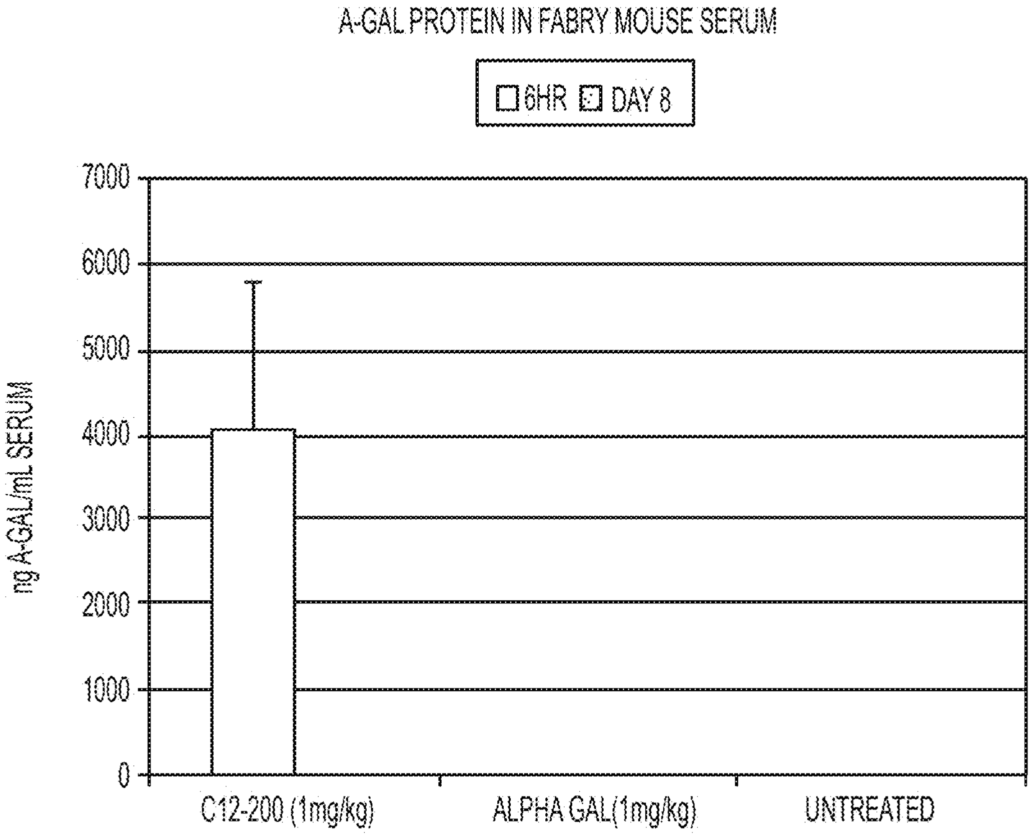
FIG. 18 shows the quantification of secreted hGLA protein levels in MRT and Alpha-galactosidase-treated Fabry mice as measured using ELISA. Both therapies were dosed as a single 1.0 mg/kg intravenous dose.

In a subsequent experiment, a comparison of ERT-based Alpha-galactosidase treatment versus hGLA MRT-based treatment of male Fabry KO mice was conducted. A single, intravenous dose of 1.0 mg/kg was given for each therapy and the mice were sacrificed one week post-administration. Serum levels of hGLA protein were monitored at 6 hr and 1 week post-injection. Liver, kidney, spleen, and heart were analyzed for hGLA protein accumulation one week post-administration. In addition to the biodistribution analyses, a measure of efficacy was determined via measurement of globotrioasylceramide (Gb3) and lyso-Gb3 reductions in the kidney and heart. FIG. 18 shows the serum levels of hGLA protein after treatment of either Alpha-galactosidase or GLA mRNA loaded lipid nanoparticles (Formulation 1) in male Fabry mice. Serum samples were analyzed at 6 hr and 1 week post-administration. A robust signal was detected for MRT-treated mice after 6 hours, with hGLA protein serum levels of ~4.0 ug/mL. In contrast, there was no detectable Alpha-galactosidase remaining in the bloodstream at this time.

Figure 19:
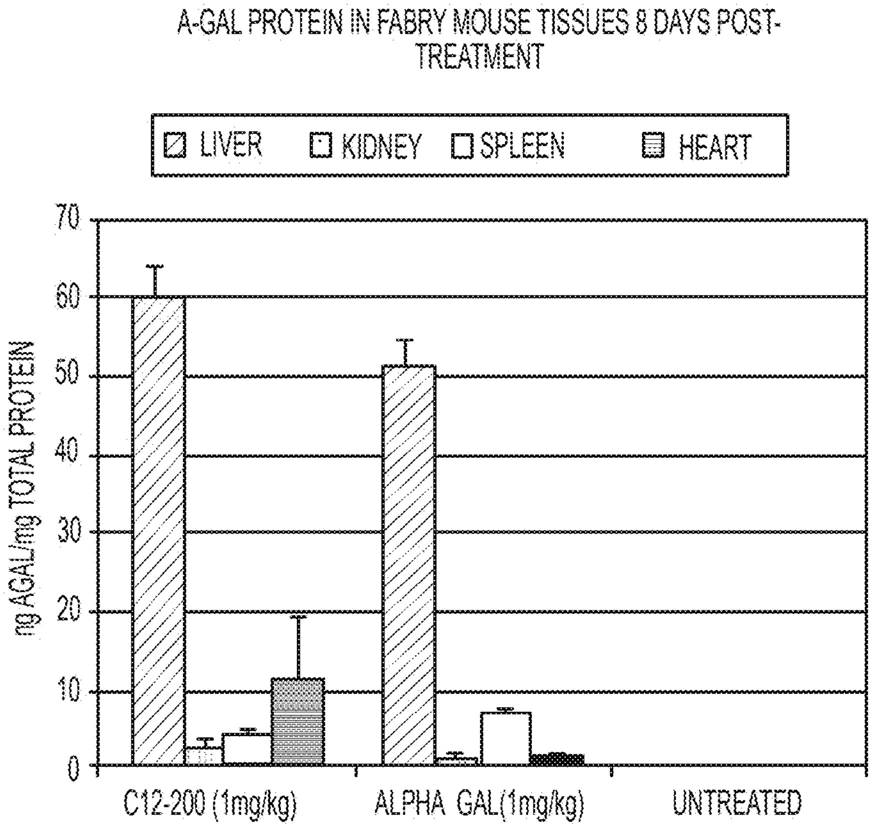
FIG. 19 shows the quantification of hGLA protein levels in liver, kidney, spleen, and heart of MRT and ERT (Alpha-galactosidase)-treated Fabry KO mice as measured via ELISA. Protein produced from hGLA mRNA delivered via lipid nanoparticles (Formulation 1; 1.0 mg/kg mRNA based on encapsulated mRNA, single IV dose).

The Fabry mice in this experiment were sacrificed one week after the initial injection and the organs were harvested and analyzed (liver, kidney, spleen, heart). FIG. 19 shows a comparison of human GLA protein found in each respective organ after either hGLA MRT or Alpha-galactosidase ERT treatment. Levels correspond to hGLA present one week post-administration. hGLA protein was detected in all organs analyzed. For example, MRT-treated mice resulted in hGLA protein accumulation in the kidney of 2.42 ng hGLA protein/mg protein, while Alpha-galactosidase-treated mice had only residual levels (0.37 ng/mg protein). This corresponds to a ~6.5-fold higher level of hGLA protein when treated via hGLA MRT. Upon analysis of the heart, 11.5 ng hGLA protein/mg protein was found for the MRT-treated cohort as compared to only 1.0 ng/mg protein Alpha-galactosidase. This corresponds to an ~11-fold higher accumulation in the heart for hGLA MRT-treated mice over ERT-based therapies.

Figure 20:
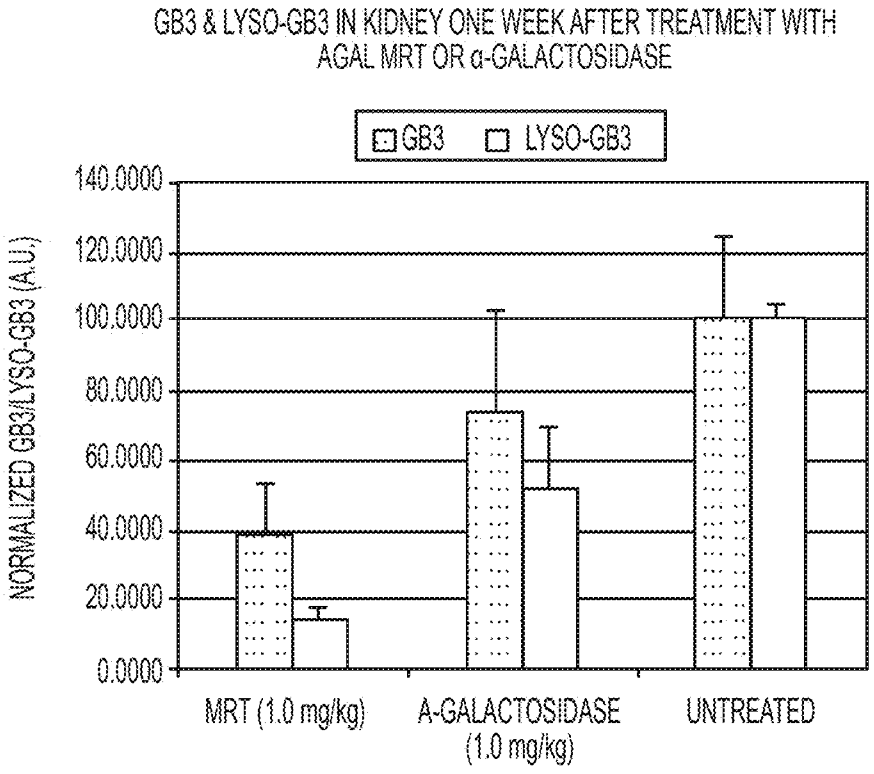
FIG. 20 shows the relative quantification of globotrioasylceramide (Gb3) and lyso-Gb3 in the kidneys of treated and untreated mice. Male Fabry KO mice were treated with a single dose either GLA mRNA-loaded lipid nanoparticles or Alpha-galactosidase at 1.0 mg/kg. Amounts reflect quantity of Gb3/lyso-Gb3 one week post-administration.
Figure 21:
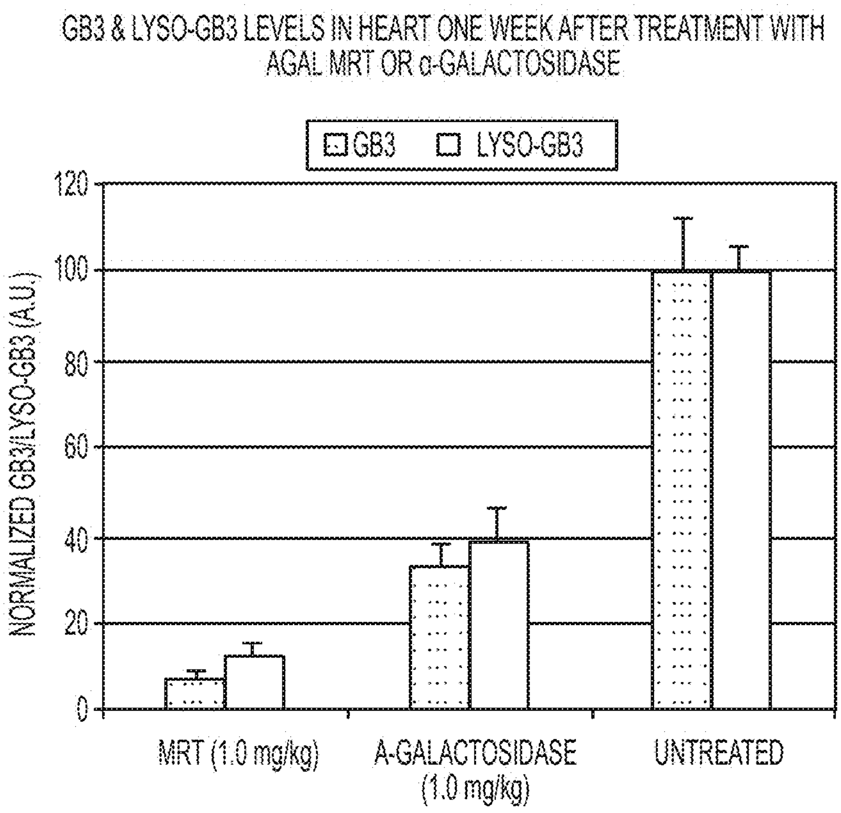
FIG. 21 shows the relative quantification of globotrioasylceramide (Gb3) and lyso-Gb3 in the heart of treated and untreated mice. Male Fabry KO mice were treated with a single dose either GLA mRNA-loaded lipid nanoparticles or Alpha-galactosidase at 1.0 mg/kg. Amounts reflect quantity of Gb3/lyso-Gb3 one week post-administration.

In addition to the biodistribution analyses conducted, evaluations of efficacy were determined via measurement of globotrioasylceramide (Gb3) and lyso-Gb3 levels in key organs. A direct comparison of Gb3 reduction after a single, intravenous 1.0 mg/kg GLA MRT treatment as compared to a Alpha-galactosidase ERT-based therapy of an equivalent dose yielded a sizeable difference in levels of Gb3 in the kidneys as well as heart. For example, Gb3 levels for GLA MRT versus Alpha-galactosidase yielded reductions of 60.2% vs 26.8%, respectively (FIG. 20). Further, Gb3 levels in the heart were reduced by 92.10% vs 66.9% for MRT and Alpha-galactosidase, respectively (FIG. 21).

A second relevant biomarker for measurement of efficacy is lyso-Gb3. GLA MRT reduced lyso-Gb3 more efficiently than Alpha-galactosidase as well in the kidneys and heart (FIG. 20 and FIG. 21, respectively). In particular, MRT-treated Fabry mice demonstrated reductions of lyso-Gb3 of 86.1% and 87.9% in the kidneys and heart as compared to Alpha-galactosidase-treated mice yielding a decrease of 47.8% and 61.3%, respectively.

Figure 22:
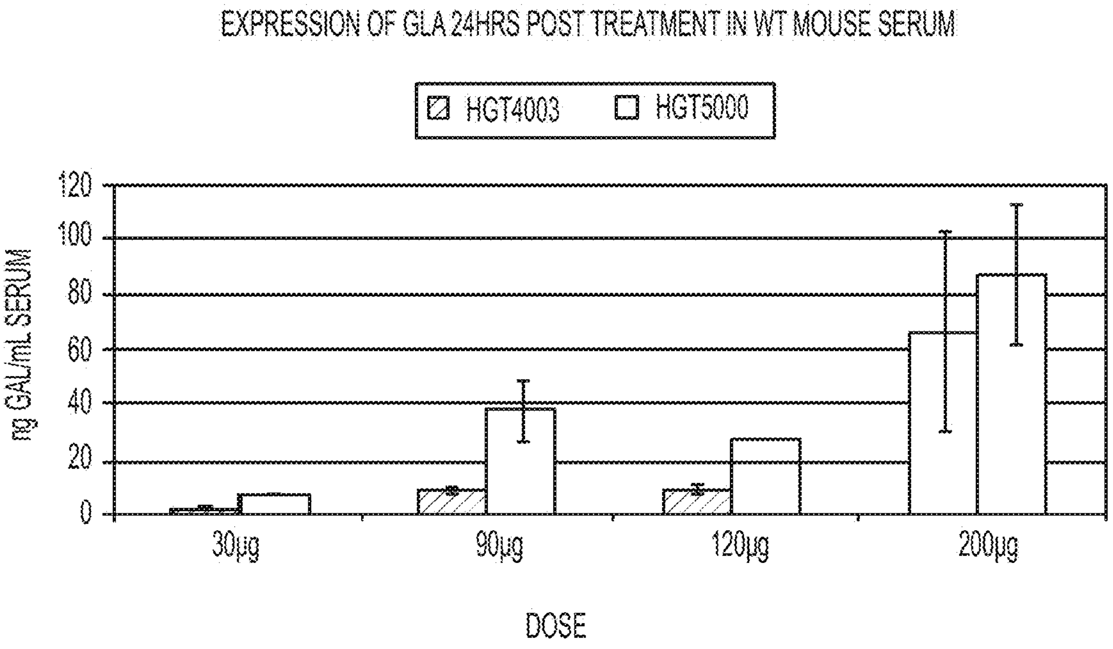
FIG. 22 shows a dose response study monitoring protein production of GLA as secreted MRT-derived human GLA protein in serum. Samples were measured 24 hours post-administration (single dose, IV, N=4 mice/group) of either HGT4003 (Formulation 3) or HGT5000-based lipid nanoparticles (Formulation 5) and quantified via ELISA.
Figure 23A:
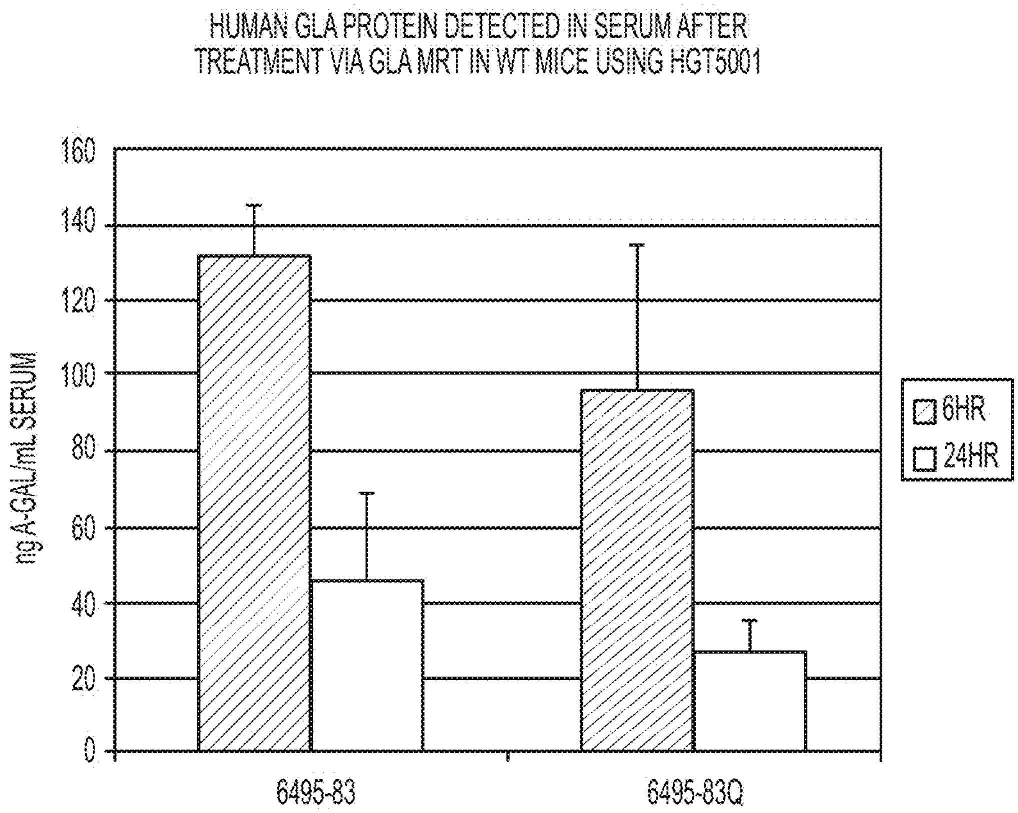
FIG. 23A shows hGLA protein production as measured in serum. Samples were measured 6 hours and 24 hours post-administration (single dose, IV, N=4 mice/group) of HGT5001-based lipid nanoparticles (Formulation 6) and quantified via ELISA.
Figure 23B:
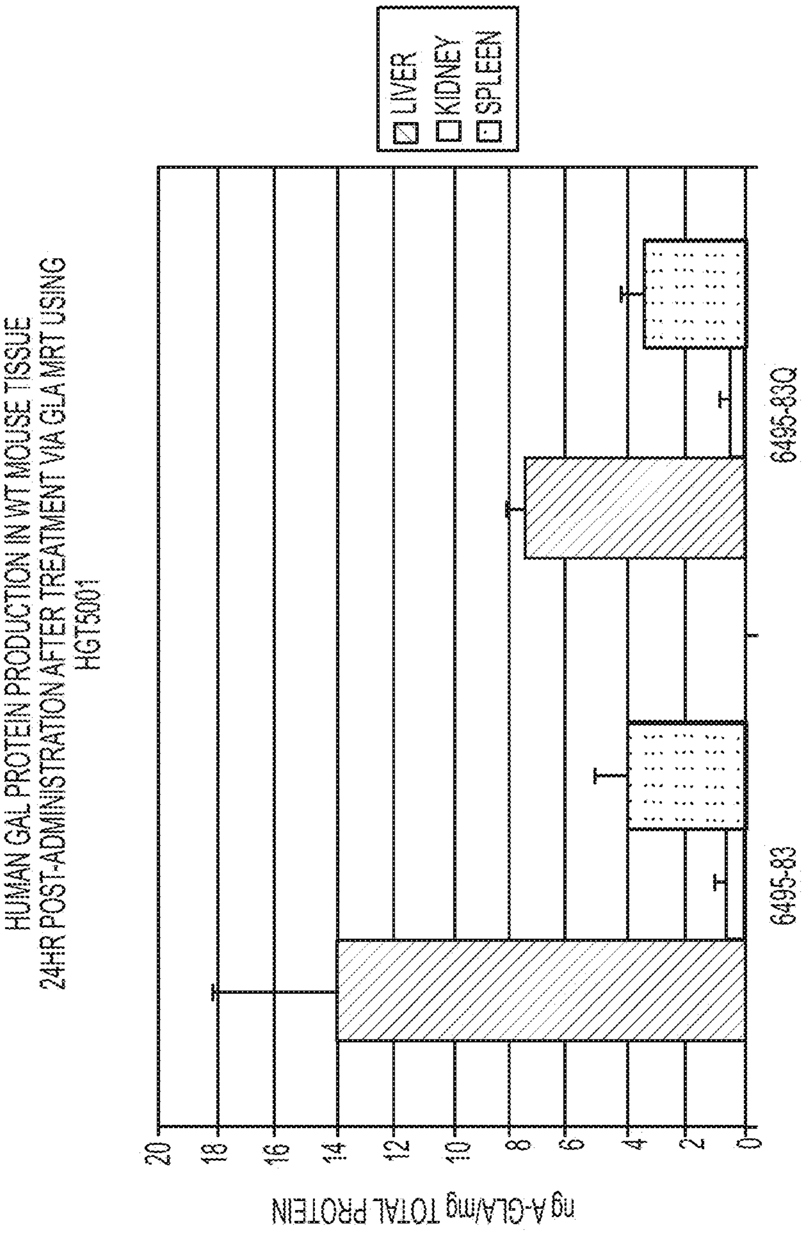
FIG. 23B shows hGLA protein production as measured in liver, kidney, and spleen (B). Samples were measured 6 hours and 24 hours post-administration (single dose, IV, N=4 mice/group) of HGT5001-based lipid nanoparticles (Formulation 6) and quantified via ELISA.

The results with for hGLA in C12-200 based lipid nanoparticles extend to other lipid nanoparticle formulations. For example, hGLA mRNA loaded into HGT4003 (Formulation 3) or HGT5000-based (Formulation 5) lipid nanoparticles administered as a single dose IV result in production of hGLA at 24 hours post administration (FIG. 22). The production of hGLA exhibited a dose response. Similarly, hGLA production was observed at 6 hours and 24 hours after administration of hGLA mRNA loaded into HGT5001-based (Formulation 6) lipid nanoparticles administered as a single dose IV. hGLA production was observed in the serum (FIG. 23A), as well as in organs (FIG. 23B).

Overall, mRNA replacement therapy applied as a depot for protein production produces large quantities of active, functionally therapeutic protein at supraphysiological levels. This method has been demonstrated to yield a sustained circulation half-life of the desired protein and this MRT-derived protein is highly efficacious for therapy as demonstrated with alpha-galactosidase enzyme in Fabry mice.

1C. In Vivo Human FIX Protein Production Results

Studies were performed administering Factor IX (FIX) mRNA-loaded lipid nanoparticles in wild type mice (CD-1) and determining FIX protein that is secreted into the bloodstream. Upon intravenous injection of a single dose of 30 ug C12-200-based (C12-200:DOPE:Chol:PEG at a ratio of 40:30:25:5) FIX mRNA-loaded lipid nanoparticles (dose based on encapsulated mRNA) (Formulation 1), a robust protein production was observed (FIG. 24).

Figure 24:
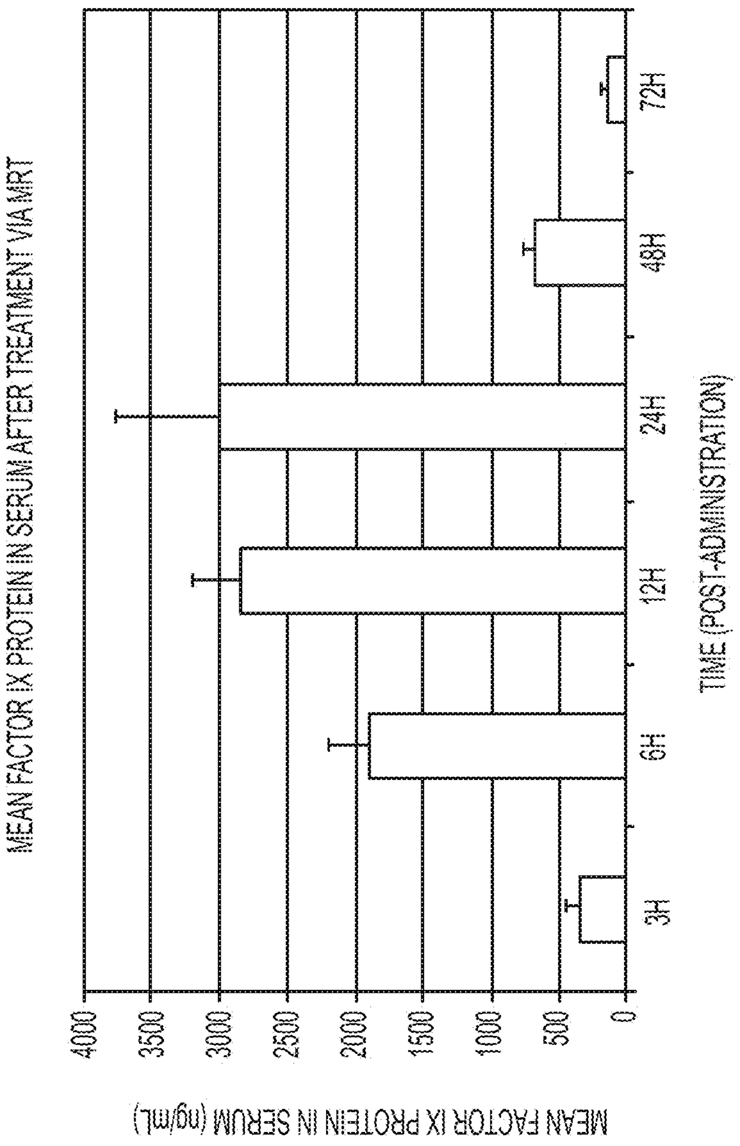
FIG. 24 shows the quantification of secreted human Factor IX protein levels measured using ELISA (mean ng/mL±standard deviation). FIX protein is produced from FIX mRNA delivered via C12-200-based lipid nanoparticles (C12-200:DOPE:Chol:DMGPEG2K, 40:30:25:5 (Formulation 1); 30 ug mRNA per single intravenous dose, based on encapsulated mRNA). FIX protein is monitored through 72 hours. (n=24 mice)

A pharmacokinetic analysis over 72 hours showed MRT-derived FIX protein could be detected at all timepoints tested (FIG. 24). The peak serum concentration was observed at 24 hr post-injection with a value of ~3 ug (2995±738 ng/mL) FIX protein/mL serum. This represents another successful example of the depot effect.

1D. In Vivo Human A1AT Protein Production Results

Studies were performed administering alpha-1-antitrypsin (A1AT) mRNA-loaded lipid nanoparticles in wild type mice (CD-1) and determining A1AT protein that is secreted into the bloodstream. Upon intravenous injection of a single dose of 30 ug C12-200-based AlAT mRNA-loaded lipid nanoparticles (dose based on encapsulated mRNA) (Formulation 1), a robust protein production was observed (FIG. 25).

Figure 25:
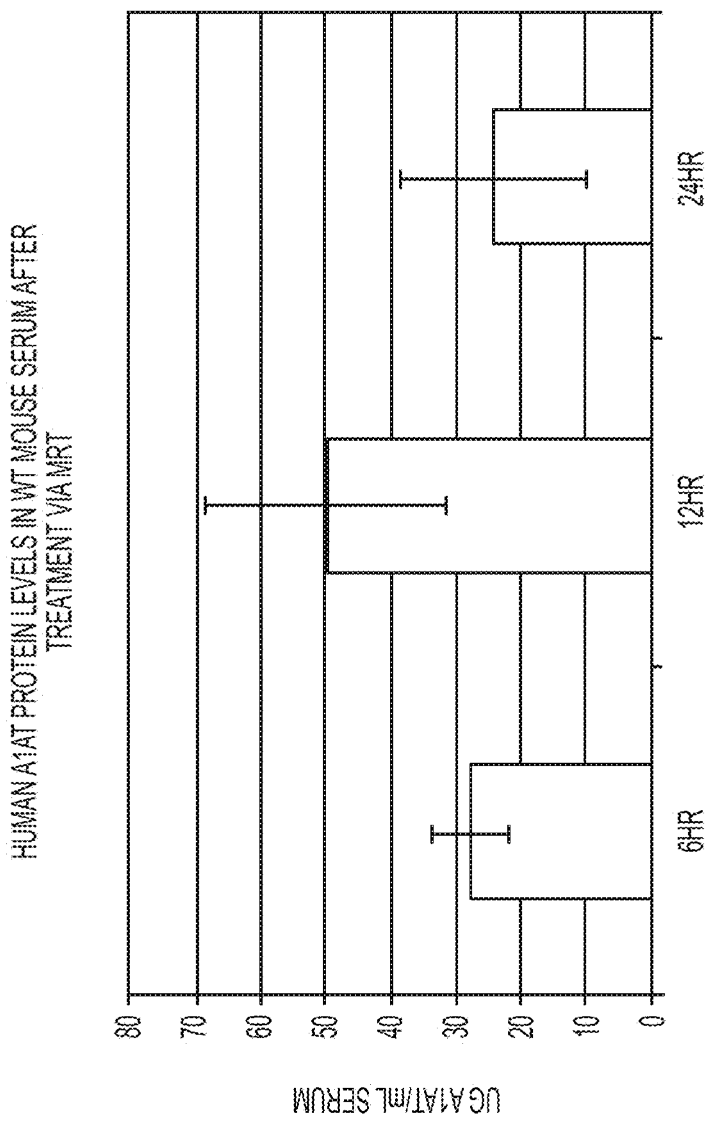
FIG. 25 shows the quantification of secreted human α-1-antitrypsin (A1AT) protein levels measured using ELISA. A1AT protein is produced from A1AT mRNA delivered via C12-200-based lipid nanoparticles (C12-200:DOPE:Chol: DMGPEG2K, 40:30:25:5 (Formulation 1); 30 ug mRNA per single intravenous dose, based on encapsulated mRNA). A1AT protein is monitored through 24 hours.

As depicted in FIG. 25, detectable levels of human A1AT protein derived from A1AT MRT could be observed over a 24 hour time period post-administration. A maximum serum level of ~48 ug AlAT protein/mL serum was detected 12 hours after injection.

Example 2: Protein Production Depot Via Pulmonary Delivery of Polynucleotide Compositions Injection Protocol All studies were performed using female CD-1 or BALB/C mice of approximately 7-10 weeks of age at the beginning of each experiment. Test articles were introduced via a single intratracheal aerosolized administration. Mice were sacrificed and perfused with saline at the designated time points. The lungs of each mouse were harvested, apportioned into two parts, and stored in either 10% neutral buffered formalin or snap-frozen and stored at −80° C. for analysis. Serum was isolated as described in Example 1. EPO ELISA: as described in Example 1.

Results

The depot effect can be achieved via pulmonary delivery (e.g. intranasal, intratracheal, nebulization). Measurement of the desired exogenous-based protein derived from messenger RNA delivered via nanoparticle systems was achieved and quantified.

The production of human EPO protein via hEPO mRNA-loaded lipid nanoparticles was tested in CD-1 mice via a single intratracheal administration (MicroSprayer®). Several formulations were tested using various cationic lipids (Formulations 1, 5, 6). All formulations resulted in high encapsulation of human EPO mRNA. Upon administration, animals were sacrificed six hours post-administration and the lungs as well as serum were harvested.

Figure 26:
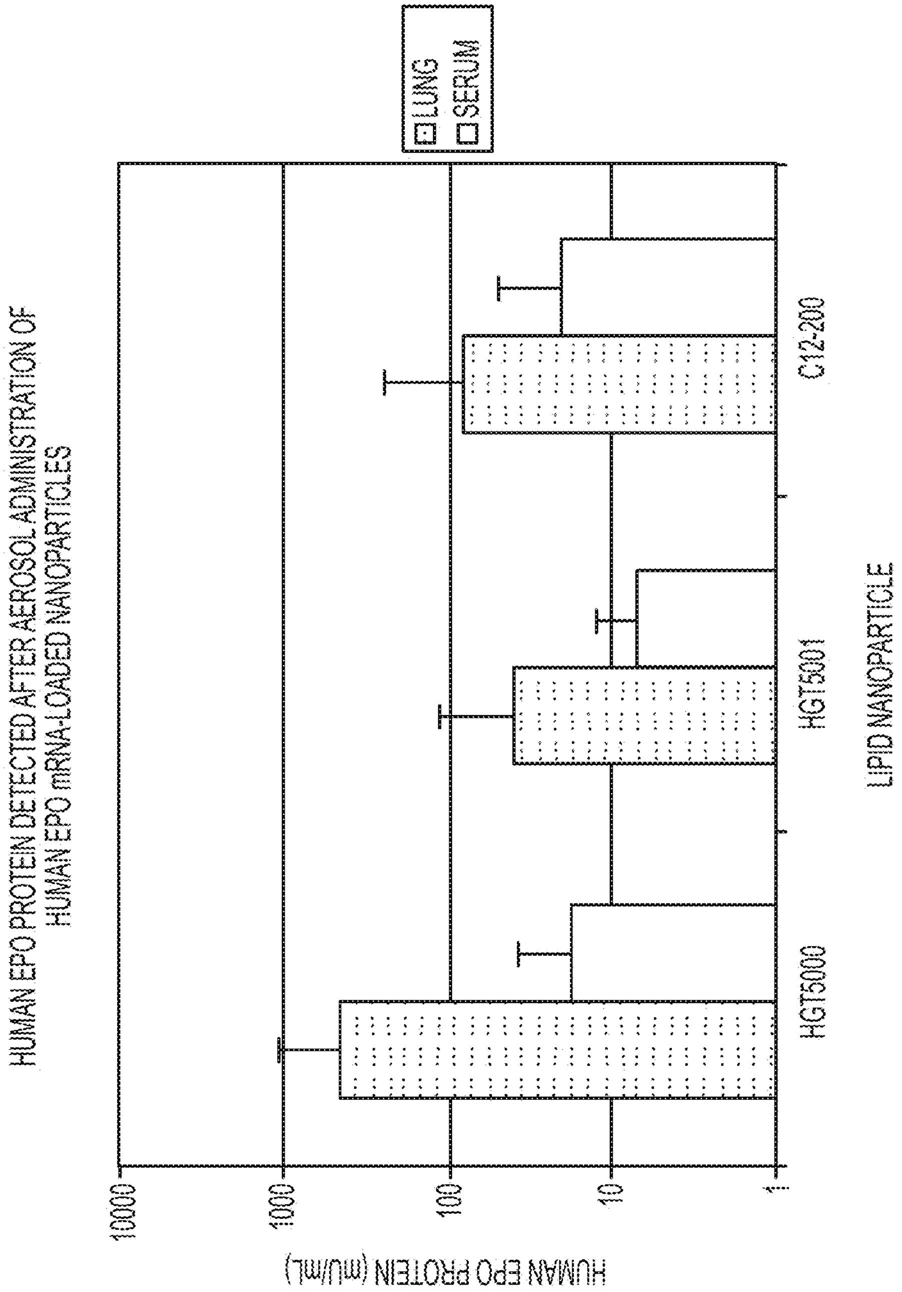
FIG. 26 shows an ELISA-based quantification of hEPO protein detected in the lungs and serum of treated mice after intratracheal administration of hEPO mRNA-loaded nanoparticles (measured mIU) (C12-200, HGT5000, or HGT5001-based lipid nanoparticles; Formulations 1, 5, 6 respectively). Animals were sacrificed 6 hours post-administration (n=4 mice per group).

Human EPO protein was detected at the site of administration (lungs) upon treatment via aerosol delivery. Analysis of the serum six hours post-administration showed detectable amounts of hEPO protein in circulation. These data (shown in FIG. 26) demonstrate the ability of the lung to act as a "depot" for the production (and secretion) of hEPO protein.

The invention claimed is:

1. A composition comprising an mRNA encoding a cytokine, encapsulated within a lipid nanoparticle, wherein the lipid nanoparticle has a size less than 150 nm and comprises (i) a PEG-modified lipid at a molar ratio of greater than 1% of the total lipids in the lipid nanoparticle, (ii) a cationic lipid at a molar ratio of greater than 10% of the total lipids in the lipid nanoparticle, (iii) a non-cationic lipid at a molar ratio of greater than 5% of total lipids in the lipid nanoparticle, and (iv) cholesterol at a molar ratio of greater than 10% of the total lipids in the lipid nanoparticle.

2. The composition of claim 1, wherein the lipid nanoparticle comprises cationic lipids at a molar ratio of 20% to 70% of the total lipids.

3. The composition of claim 2, wherein the lipid nanoparticle comprises PEG-modified lipids at a molar ratio of 1% to 15% of the total lipids.

4. The composition of claim 1, wherein one or more cationic lipids comprise DSPC.

5. The composition of claim 1, wherein one or more cationic lipids comprise DOPE.

6. The composition of claim 1, wherein one or more PEG-modified lipids comprise DMG-PEG-2000.

7. The composition of claim 1, wherein the mRNA comprises a poly A tail of at least 90 nucleotides.

8. The composition of claim 7, wherein the poly A tail comprises at least 200 nucleotides.

9. The composition of claim 1, wherein the lipid nanoparticle has a size less than 125 nm.

10. The composition of claim 9, wherein the lipid nanoparticle has a size less than 100 nm.

11. The composition of claim 1, wherein the mRNA is modified.

12. The composition of claim 11, wherein the mRNA comprises pseudouridines.

13. The composition of claim 1, wherein the mRNA comprises a 5' UTR.

14. The composition of claim 1, wherein the mRNA comprises a 3' UTR.

15. The composition of claim 1, wherein the mRNA comprises a cap structure.

16. The composition of claim 1, wherein the cytokine is an IL-12.

17. The composition of claim 1, wherein the cytokine is an IL-23.

18. A composition comprising an mRNA encoding a cytokine, encapsulated within a lipid nanoparticle, wherein the lipid nanoparticle has a size less than 150 nm and comprises (i) a PEG-modified lipid at a molar ratio of greater than 1% of the total lipids in the lipid nanoparticle, (ii) a cationic lipid at a molar ratio of greater than 10% of the total lipids in the lipid nanoparticle, (iii) a non-cationic lipid at a molar ratio of greater than 5% of total lipids in the lipid nanoparticle, and (iv) cholesterol at a molar ratio greater than 10% of the total lipids in the lipid nanoparticle, and wherein the mRNA comprises (i) a 5'-UTR, (ii) a 3'-UTR, (iii) a 5' cap structure, and (iv) a poly A tail.

19. A composition comprising an mRNA encoding a cytokine, encapsulated within a lipid nanoparticle, wherein the lipid nanoparticle has a size less than 150 nm and comprises (i) a PEG-modified lipid at a molar ratio of greater than 1% of the total lipids in the lipid nanoparticle, (ii) a cationic lipid at a molar ratio of greater than 10% of the total lipids in the lipid nanoparticle, (iii) a non-cationic lipid at a molar ratio of greater than 5% of total lipids in the lipid nanoparticle, and (iv) cholesterol at a molar ratio greater than 10% of the total lipids in the lipid nanoparticle, and wherein the mRNA is modified to comprise one or more pseudouridine and the mRNA comprises (i) a 5'-UTR, (ii) a 3 '-UTR, (iii) a 5' cap structure, and (iv) a poly A tail.

* * * * *

UNITED STATES PATENT AND TRADEMARK OFFICE
CERTIFICATE OF CORRECTION

| | | |
|---|---|---|
| PATENT NO. | : 11,951,179 B2 | Page 1 of 1 |
| APPLICATION NO. | : 18/295150 | |
| DATED | : April 9, 2024 | |
| INVENTOR(S) | : Frank DeRosa, Braydon Charles Guild and Michael Heartlein | |

It is certified that error appears in the above-identified patent and that said Letters Patent is hereby corrected as shown below:

In the Claims

Claim 4, Column 40, Line 61, "cationic lipids comprise DSPC." should be -- non-cationic lipids comprise DSPC. --

Claim 5, Column 40, Line 63, "cationic lipids comprise DOPE." should be -- non-cationic lipids comprise DOPE. --

Signed and Sealed this
Seventh Day of May, 2024

Katherine Kelly Vidal
*Director of the United States Patent and Trademark Office*